(12) United States Patent
Wachendorff-Neumann et al.

(10) Patent No.: US 9,844,220 B2
(45) Date of Patent: Dec. 19, 2017

(54) SYNERGISTIC FUNGICIDAL ACTIVE SUBSTANCE COMBINATIONS

(71) Applicant: FMC Corporation, Philadelphia, PA (US)

(72) Inventors: Ulrike Wachendorff-Neumann, Neuwied (DE); Peter Dahmen, Neuss (DE); Ralf Dunkel, Lyons (FR); Hans-Ludwig Elbe, Wuppertal (DE); Anne Suty-Heinze, Langenfeld (DE); Heiko Rieck, Ste. Foy les Lyon (FR)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/019,466

(22) Filed: Feb. 9, 2016

(65) Prior Publication Data

US 2016/0150785 A1 Jun. 2, 2016

Related U.S. Application Data

(60) Continuation of application No. 13/800,076, filed on Mar. 13, 2013, now Pat. No. 9,288,988, which is a (Continued)

(30) Foreign Application Priority Data

Oct. 10, 2003 (DE) .................... 103-47-090

(51) Int. Cl.
*A01N 37/24* (2006.01)
*A01N 37/34* (2006.01)
*A01N 37/50* (2006.01)
*A01N 41/10* (2006.01)
*A01N 43/30* (2006.01)
*A01N 43/707* (2006.01)
*A01N 43/653* (2006.01)
*A01N 43/78* (2006.01)
*A01N 43/88* (2006.01)
(Continued)

(52) U.S. Cl.
CPC ............ *A01N 43/56* (2013.01); *A01N 37/10* (2013.01); *A01N 37/24* (2013.01); *A01N 37/34* (2013.01); *A01N 37/50* (2013.01); *A01N 41/10* (2013.01); *A01N 43/28* (2013.01); *A01N 43/30* (2013.01); *A01N 43/40* (2013.01); *A01N 43/50* (2013.01); *A01N 43/54* (2013.01); *A01N 43/653* (2013.01); *A01N 43/707* (2013.01); *A01N 43/78* (2013.01); *A01N 43/80* (2013.01); *A01N 43/88* (2013.01); *A01N 43/90* (2013.01); *A01N 47/08* (2013.01); *A01N 47/18* (2013.01); *A01N 47/20* (2013.01); *A01N 47/30* (2013.01); *A01N 47/38* (2013.01); *A01N 55/02* (2013.01); *A01N 57/12* (2013.01); *C07D 213/64* (2013.01); *C07D 231/22* (2013.01); *C07D 239/52* (2013.01); *C07D 251/50* (2013.01); *C07D 273/01* (2013.01)

(58) Field of Classification Search
CPC ........ A01N 37/10; A01N 37/24; A01N 37/34; A01N 37/50; A01N 43/40; A01N 43/56; A01N 43/28; A01N 43/30; A01N 43/50; A01N 43/54; A01N 43/653; A01N 43/707; A01N 43/78; A01N 43/80; A01N 43/88; A01N 43/90; A01N 41/10; A01N 47/08; A01N 47/18; A01N 47/20; A01N 47/30; A01N 47/38; A01N 55/02; A01N 57/12; C07D 213/64; C07D 231/22; C07D 239/52; C07D 251/50; C07D 273/01

See application file for complete search history.

(56) References Cited

U.S. PATENT DOCUMENTS 1,972,961 A 9/1934 Tisdale et al.
2,504,404 A 4/1950 Flenner
(Continued)

FOREIGN PATENT DOCUMENTS

AU 7726387 A 2/1988
AU 610 079 B 5/1991
(Continued)

OTHER PUBLICATIONS

Colby, S.R., "Calculating Synergistic and Antagonistic Responses of Herbicide Combinations," *Weeds* 15:20-22, Weed Society of America (1967).
(Continued)

*Primary Examiner* — Sarah Pihonak
(74) *Attorney, Agent, or Firm* — Sterne, Kessler, Goldstein & Fox P.L.L.C.

(57) ABSTRACT

Novel active compound combinations comprising a carboxamide of the general formula (I) (group 1)

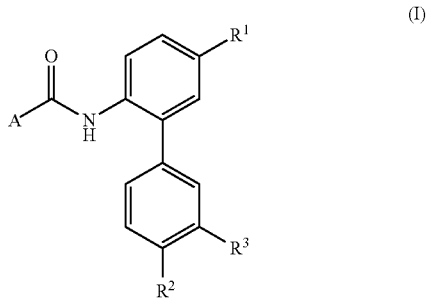

in which
A, $R^1$, $R^2$ and $R^3$ are as defined in the description,
and the active compound groups (2) to (23) listed in the description have very good fungicidal properties.

6 Claims, No Drawings

US 9,844,220 B2

Page 2

Related U.S. Application Data division of application No. 10/573,066, filed as application No. PCT/EP2004/010830 on Sep. 28, 2004, now Pat. No. 8,415,274.

(51) Int. Cl.

| | | |
|---|---|---|
| *A01N 43/80* | (2006.01) | |
| *A01N 43/90* | (2006.01) | |
| *A01N 47/08* | (2006.01) | |
| *A01N 47/18* | (2006.01) | |
| *A01N 47/20* | (2006.01) | |
| *A01N 47/30* | (2006.01) | |
| *A01N 47/38* | (2006.01) | |
| *A01N 55/02* | (2006.01) | |
| *A01N 57/12* | (2006.01) | |
| *C07D 251/50* | (2006.01) | |
| *C07D 273/01* | (2006.01) | |
| *C07D 213/64* | (2006.01) | |
| *C07D 231/22* | (2006.01) | |
| *C07D 239/52* | (2006.01) | |
| *A01N 37/10* | (2006.01) | |
| *A01N 43/28* | (2006.01) | |
| *A01N 43/40* | (2006.01) | |
| *A01N 43/50* | (2006.01) | |
| *A01N 43/54* | (2006.01) | |
| *A01N 43/56* | (2006.01) | |

(56) References Cited

U.S. PATENT DOCUMENTS

| | | |
|---|---|---|
| 2,553,770 A | 5/1951 | Kittleson et al. |
| 2,588,428 A | 3/1952 | Stewart et al. |
| 3,010,968 A | 11/1961 | Loux |
| 3,178,447 A | 4/1965 | Kohn |
| 3,206,468 A | 9/1965 | Grenda |
| 3,248,400 A | 4/1966 | Flieg et al. |
| 3,249,499 A | 5/1966 | von Schmeling et al. |
| 3,285,929 A | 11/1966 | Klauke et al. |
| 3,290,353 A | 12/1966 | Battershell et al. |
| 3,379,610 A | 4/1968 | Lyon et al. |
| 3,499,951 A | 3/1970 | Schrader et al. |
| 3,513,241 A | 5/1970 | Hoyer et al. |
| 3,546,813 A | 12/1970 | Frohberger et al. |
| 3,629,428 A | 12/1971 | Seki et al. |
| 3,631,176 A | 12/1971 | Klopping |
| 3,745,170 A | 7/1973 | Fujinami et al. |
| 3,745,187 A | 7/1973 | Noguchi et al. |
| 3,755,350 A | 8/1973 | Sauli |
| 3,856,814 A | 12/1974 | Taninaka et al. |
| 3,912,752 A | 10/1975 | Meiser et al. |
| 3,952,002 A | 4/1976 | Kramer et al. |
| 3,966,750 A | 6/1976 | Mangold et al. |
| 3,991,071 A | 11/1976 | Brookes et al. |
| 4,046,911 A | 9/1977 | Hubele |
| 4,064,261 A | 12/1977 | Paget |
| 4,068,077 A | 1/1978 | Goetz et al. |
| 4,079,062 A | 3/1978 | Van Reet et al. |
| 4,127,673 A | 11/1978 | Yamada et al. |
| 4,139,616 A | 2/1979 | Ducret et al. |
| 4,239,760 A | 12/1980 | Sasse et al. |
| 4,291,049 A | 9/1981 | Bosone et al. |
| 4,294,850 A | 10/1981 | Hubele |
| 4,432,989 A | 2/1984 | Spencer |
| 4,532,341 A | 7/1985 | Holmwood et al. |
| 4,598,085 A | 7/1986 | Heeres et al. |
| 4,664,696 A | 5/1987 | Schaub |
| 4,705,800 A | 11/1987 | Nyfeler et al. |
| 4,829,085 A | 5/1989 | Wenderoth et al. |
| 4,851,405 A | 7/1989 | Krámer et al. |
| 4,906,652 A | 3/1990 | Karbach et al. |
| 4,910,200 A | 3/1990 | Curtze et al. |
| 4,931,560 A | 6/1990 | Hubele |
| 4,931,581 A | 6/1990 | Schurter et al. |
| 4,988,734 A | 1/1991 | Kraatz et al. |
| 5,059,623 A | 10/1991 | Krüger et al. |
| 5,087,635 A | 2/1992 | Shaber |
| 5,112,849 A | 5/1992 | Staub et al. |
| 5,256,683 A | 10/1993 | Hutt et al. |
| 5,266,585 A | 11/1993 | Hubele et al. |
| 5,330,995 A | 7/1994 | Eicken et al. |
| 5,334,607 A | 8/1994 | Sauter et al. |
| 5,438,070 A | 8/1995 | Eicken et al. |
| 5,453,531 A | 9/1995 | Seitz et al. |
| 5,593,996 A | 1/1997 | Pees et al. |
| 5,599,828 A | 2/1997 | Zeun et al. |
| 5,650,519 A | 7/1997 | Lacroix et al. |
| 5,679,676 A | 10/1997 | Krüger et al. |
| 5,789,428 A | 8/1998 | Shibata et al. |
| 5,789,430 A | 8/1998 | Jautelat et al. |
| 5,859,039 A | 1/1999 | Jautelat et al. |
| 5,869,517 A | 2/1999 | Müller et al. |
| 5,948,932 A | 9/1999 | Grote et al. |
| 5,986,135 A | 11/1999 | Pfrengle et al. |
| 5,998,450 A | 12/1999 | Eicken et al. |
| 5,998,455 A | 12/1999 | Knauf-Beiter et al. |
| 6,020,354 A | 2/2000 | Assmann et al. |
| 6,103,717 A | 8/2000 | Heinemann et al. |
| 6,114,362 A | 9/2000 | Dutzmann et al. |
| 6,130,224 A | 10/2000 | Eicken et al. |
| 6,143,745 A | 11/2000 | Eicken et al. |
| 6,159,992 A | 12/2000 | Müller et al. |
| 6,169,056 B1 | 1/2001 | Bayer et al. |
| 6,191,128 B1 | 2/2001 | Stenzel et al. |
| 6,235,743 B1 | 5/2001 | Gayer et al. |
| 6,277,791 B1 | 8/2001 | Assmann et al. |
| 6,297,263 B1 | 10/2001 | Dutzmann et al. |
| 6,306,414 B1 | 10/2001 | Koike |
| 6,306,850 B1 | 10/2001 | Dutzmann et al. |
| 6,346,538 B1 | 2/2002 | Schelberger et al. |
| 6,350,765 B1 | 2/2002 | Schelberger et al. |
| 6,355,634 B1 | 3/2002 | Isenring et al. |
| 6,372,748 B1 | 4/2002 | Schelberger et al. |
| 6,407,100 B1 | 6/2002 | Isenring et al. |
| 6,423,726 B2 | 7/2002 | Dutzmann et al. |
| 6,479,542 B2 | 11/2002 | Sembo et al. |
| 6,559,136 B1 | 5/2003 | Mauler-Machnik et al. |
| 6,602,823 B1 | 8/2003 | Röchling et al. |
| 7,008,903 B2 | 3/2006 | Dutzmann et al. |
| 7,329,633 B2 | 2/2008 | Dunkel et al. |
| 7,358,214 B2 | 4/2008 | Dunkel et al. |
| 7,521,397 B2 | 4/2009 | Dunkel et al. |
| 7,538,073 B2 | 5/2009 | Elbe et al. |
| 7,655,599 B2 | 2/2010 | Röchling et al. |
| 7,799,739 B2 | 9/2010 | Dunkel et al. |
| 7,820,708 B2 | 10/2010 | Dunkel et al. |
| 7,879,760 B2 | 2/2011 | Dunkel et al. |
| 8,415,274 B2 | 4/2013 | Wachendorff-Neumann et al. |
| 8,486,858 B2 | 7/2013 | Seitz et al. |
| 8,652,997 B2 | 2/2014 | Assmann et al. |
| 2002/0156108 A1 | 10/2002 | Eicken et al. |
| 2002/0173529 A1 | 11/2002 | Dutzmann et al. |
| 2002/0198222 A1 | 12/2002 | Bruns et al. |
| 2004/0039043 A1 | 2/2004 | Elbe et al. |
| 2004/0110771 A1 | 6/2004 | Blasco et al. |
| 2005/0009703 A1 | 1/2005 | Wachendorff-Neumann et al. |
| 2005/0009883 A1 | 1/2005 | Uhr et al. |
| 2005/0101639 A1 | 5/2005 | Ammermann et al. |
| 2005/0124815 A1 | 6/2005 | Elbe et al. |
| 2005/0143428 A1 | 6/2005 | Dunkel et al. |
| 2005/0165076 A1 | 7/2005 | Ammermann et al. |
| 2006/0004070 A1 | 1/2006 | Wachendorff-Neumann et al. |
| 2006/0014738 A1 | 1/2006 | Wachendorff-Neumann et al. |
| 2006/0035942 A1 | 2/2006 | Wachendorff-Neumann et al. |
| 2006/0079401 A1 | 4/2006 | Dutzmann et al. |
| 2006/0116414 A1 | 6/2006 | Dunkel et al. |
| 2006/0276342 A1 | 12/2006 | Krahmer et al. |
| 2007/0004921 A1 | 1/2007 | Dunkel et al. |
| 2007/0010399 A1 | 1/2007 | Rosinger et al. |
| 2007/0037799 A1 | 2/2007 | Dahmen et al. |
| 2007/0054804 A1 | 3/2007 | Suty-Heinze |
| 2007/0078171 A1 | 4/2007 | Andersch et al. |

(56) References Cited

U.S. PATENT DOCUMENTS

| | | |
|---|---|---|
| 2007/0142327 A1 | 6/2007 | Funke et al. |
| 2007/0155797 A1 | 7/2007 | Andersch et al. |
| 2007/0196406 A1 | 8/2007 | Dunkel et al. |
| 2007/0203025 A1 | 8/2007 | Bickers et al. |
| 2007/0213396 A1 | 9/2007 | Thielert et al. |
| 2007/0232598 A1 | 10/2007 | Funke et al. |
| 2007/0270416 A1 | 11/2007 | Funke et al. |
| 2007/0293550 A1 | 12/2007 | Röchling et al. |
| 2007/0298966 A1 | 12/2007 | Fischer et al. |
| 2008/0027114 A1 | 1/2008 | Funke et al. |
| 2008/0070863 A1 | 3/2008 | Funke et al. |
| 2008/0255071 A1 | 10/2008 | Suty-Heinze et al. |
| 2008/0261811 A1 | 10/2008 | Krohn et al. |
| 2008/0269051 A1 | 10/2008 | Suty-Heinze et al. |
| 2008/0269263 A1 | 10/2008 | Dahmen et al. |
| 2008/0274882 A1 | 11/2008 | Krohn et al. |
| 2009/0018015 A1 | 1/2009 | Wachendorff-Neumann et al. |
| 2009/0069178 A1 | 3/2009 | Suty-Heinze et al. |
| 2009/0069398 A1 | 3/2009 | Dunkel et al. |
| 2009/0105311 A1 | 4/2009 | Dunkel et al. |
| 2009/0118346 A1 | 5/2009 | Dunkel et al. |
| 2009/0170912 A1 | 7/2009 | Erdelen et al. |
| 2009/0170918 A1 | 7/2009 | Wolf |
| 2009/0286681 A1 | 11/2009 | Dahmen et al. |
| 2009/0306109 A1 | 12/2009 | Dutzmann et al. |
| 2011/0033433 A1 | 2/2011 | Davies et al. |
| 2011/0034496 A1 | 2/2011 | Häuser-Hahn et al. |
| 2011/0110906 A1 | 5/2011 | Andersch et al. |
| 2011/0124501 A1 | 5/2011 | Cristau et al. |
| 2011/0152097 A1 | 6/2011 | Stenzel et al. |
| 2012/0015910 A1 | 1/2012 | Wachendorff-Neumann et al. |
| 2013/0197018 A1 | 8/2013 | Wachendorff-Neumann et al. |

FOREIGN PATENT DOCUMENTS

| | | |
|---|---|---|
| CA | 2 476 462 C | 4/2011 |
| DE | 1 076 434 | 2/1960 |
| DE | 1 081 446 | 5/1960 |
| DE | 1 193 498 | 5/1965 |
| DE | 1 209 799 | 1/1966 |
| DE | 1 234 704 | 2/1967 |
| DE | 1 493 736 | 4/1969 |
| DE | 1 806 123 | 6/1969 |
| DE | 2 012 656 | 9/1971 |
| DE | 2 149 923 | 4/1972 |
| DE | 2 250 077 | 4/1973 |
| DE | 2 201 063 | 7/1973 |
| DE | 2 207 576 | 8/1973 |
| DE | 2 312 956 | 9/1973 |
| DE | 23 24 010 A1 | 1/1975 |
| DE | 24 29 523 A1 | 1/1975 |
| DE | 24 56 627 A1 | 6/1975 |
| DE | 25 13 732 A1 | 10/1975 |
| DE | 25 15 091 A1 | 10/1975 |
| DE | 25 51 560 A1 | 5/1976 |
| DE | 25 43 279 A1 | 4/1977 |
| DE | 27 32 257 A1 | 1/1978 |
| DE | 27 35 872 A1 | 2/1978 |
| DE | 26 56 747 A1 | 6/1978 |
| DE | 28 02 488 A1 | 7/1979 |
| DE | 29 03 612 A1 | 8/1979 |
| DE | 140 041 | 2/1980 |
| DE | 30 30 026 A1 | 3/1981 |
| DE | 30 42 303 A1 | 8/1981 |
| DE | 151 404 | 10/1981 |
| DE | 34 06 993 A1 | 9/1984 |
| DE | 37 21 786 A1 | 1/1988 |
| DE | 37 35 555 A1 | 9/1988 |
| DE | 40 26 966 A1 | 2/1992 |
| DE | 44 23 612 A1 | 1/1996 |
| DE | 195 31 813 A1 | 3/1997 |
| DE | 195 39 324 A1 | 4/1997 |
| DE | 196 02 095 A1 | 7/1997 |
| DE | 196 46 407 A1 | 5/1998 |
| DE | 101 24 208 A1 | 11/2002 |
| DE | 102 15 292 A1 | 8/2003 |
| EP | 0 015 756 A1 | 9/1980 |
| EP | 0 019 450 A1 | 11/1980 |
| EP | 0 031 257 A2 | 7/1981 |
| EP | 0 040 345 A1 | 11/1981 |
| EP | 0 040 345 B1 | 11/1981 |
| EP | 0 068 813 A2 | 1/1983 |
| EP | 0 078 663 A2 | 5/1983 |
| EP | 0 112 284 A2 | 6/1984 |
| EP | 0 145 294 A2 | 6/1985 |
| EP | 0 155 509 A1 | 9/1985 |
| EP | 0 183 458 A1 | 6/1986 |
| EP | 0 196 038 A2 | 10/1986 |
| EP | 0 206 999 A2 | 12/1986 |
| EP | 0 219 756 A1 | 4/1987 |
| EP | 0 234 242 A2 | 9/1987 |
| EP | 0 236 272 A1 | 9/1987 |
| EP | 0 248 086 A1 | 12/1987 |
| EP | 0 253 213 A1 | 1/1988 |
| EP | 0 256 503 A2 | 2/1988 |
| EP | 0 258 161 A2 | 3/1988 |
| EP | 0 262 393 A1 | 4/1988 |
| EP | 0 270 111 A1 | 6/1988 |
| EP | 0 278 595 A2 | 8/1988 |
| EP | 0 298 196 A1 | 1/1989 |
| EP | 0 310 550 A1 | 4/1989 |
| EP | 0 313 512 A2 | 4/1989 |
| EP | 0 315 502 A1 | 5/1989 |
| EP | 0 329 397 A1 | 8/1989 |
| EP | 0 339 418 A2 | 11/1989 |
| EP | 0 341 475 A2 | 11/1989 |
| EP | 0 378 953 A1 | 7/1990 |
| EP | 0 382 375 A2 | 8/1990 |
| EP | 0 393 911 A1 | 10/1990 |
| EP | 0 398 692 A2 | 11/1990 |
| EP | 0 460 575 A1 | 12/1991 |
| EP | 0 515 901 A1 | 12/1992 |
| EP | 0 537 957 A1 | 4/1993 |
| EP | 0 545 099 A2 | 6/1993 |
| EP | 0 589 301 A1 | 3/1994 |
| EP | 0 596 254 A1 | 5/1994 |
| EP | 0 600 629 A1 | 6/1994 |
| EP | 0 604 019 A1 | 6/1994 |
| EP | 0 629 616 A2 | 12/1994 |
| EP | 0 639 574 A1 | 2/1995 |
| EP | 0 737 682 A1 | 10/1996 |
| EP | 0 897 904 A1 | 2/1999 |
| EP | 1 214 881 A1 | 6/2002 |
| GB | 935981 | 9/1963 |
| GB | 988630 | 4/1965 |
| GB | 1094567 | 12/1967 |
| GB | 1103989 | 2/1968 |
| GB | 1114155 | 5/1968 |
| GB | 1 425 621 | 2/1976 |
| GB | 1 591 267 | 6/1981 |
| GB | 2 262 037 A | 6/1993 |
| JP | 07-206608 | 8/1995 |
| WO | WO 92/13830 A1 | 8/1992 |
| WO | WO 95/04728 A1 | 2/1995 |
| WO | WO 96/01559 A1 | 1/1996 |
| WO | WO 96/04252 A1 | 2/1996 |
| WO | WO 96/16048 A1 | 5/1996 |
| WO | WO 96/18631 A1 | 6/1996 |
| WO | WO 96/23793 A1 | 8/1996 |
| WO | WO 97/06171 A1 | 2/1997 |
| WO | WO 97/08952 A1 | 3/1997 |
| WO | WO 97/10716 A1 | 3/1997 |
| WO | WO 97/39630 A1 | 10/1997 |
| WO | WO 98/08385 A1 | 3/1998 |
| WO | WO 98/23155 A1 | 6/1998 |
| WO | WO 99/14202 A2 | 3/1999 |
| WO | WO 99/24413 A2 | 5/1999 |
| WO | WO 99/31980 A2 | 7/1999 |
| WO | WO 99/31985 A1 | 7/1999 |
| WO | WO 99/42447 A1 | 8/1999 |
| WO | WO 99/63813 A2 | 12/1999 |
| WO | WO 01/87822 A1 | 11/2001 |
| WO | WO 02/08197 A1 | 1/2002 |
| WO | WO 02/38542 A1 | 5/2002 |

(56) References Cited

FOREIGN PATENT DOCUMENTS

| WO | WO 02/38565 A2  | 5/2002 |
| --- | --- | --- |
| WO | WO 03/014103 A1 | 2/2003 |
| WO | WO 03/066609 A1 | 8/2003 |
| WO | WO 03/066610 A1 | 8/2003 |
| WO | WO 03/070705 A1 | 8/2003 |

OTHER PUBLICATIONS

"Dicholofluanid," in *The Pesticide Manual: A World Compendium*, 9th edition, Worthing, C.E., ed., Hampshire, UK, p. 249(1991).
"Tolylfluanid," in *The Pesticide Manual: A World Compendium*, 9th edition, Worthing, C.E., ed., Hampshire, UK, p. 827(1991).
Patent Abstracts of Japan, English language abstract for JP 07-206608 (listed on accompanying PTO/SB/08A as FP88), 1995.
STNEasy Database, Accession No. 1962:12696, English language abstract for DE 1 081 446 (listed on accompanying PTO/SB/08A as FP2).
STNEasy Database, Accession No. 1980:586371, English language abstract for DD 140 041 (listed on accompanying PTO/SB/08A as FP32).
STNEasy Database, Accession No. 1981:401897, English language abstract for DE 30 30 026 (listed on accompanying PTO/SB/08A as FP35).
STNEasy Database, Accession No. 1982:157395, English language abstract for DD 151 404 (listed on accompanying PTO/SB/08A as FP39).
STNEasy Database, Accession No. 1988:510440, English language abstract for EP 0 258 161 (listed on accompanying PTO/SB/08A as FP58).
International Search Report for International Application No. PCT/EP2004/010830, European Patent Office, Netherlands, completed Nov. 22, 2004.
Bauer, T.A., et al., "Response of Selected Weed Species to Postemergence Imazethapyr and Bentazon," *Weed Tech.* 9:236-242, The Weed Science Society of America, United States (1995).
Blackshaw, R.E., "HOE-39866 Use in Chemical Fallow Systems," *Weed Tech.* 3:420-428, The Weed Science Society of America, United States (1989).
Blackshaw, R.E., "Synergistic Mixes of DPX-A7881 and Clopyralid in Canola (*Brassica napus*)," *Weed Tech.* 3:690-695, The Weed Science Society of America, United States (1989).
Blackshaw, R.E., et al., "Herbicide Combinations for Postemergent Weed Control in Safflower (*Carthamus tinctorius*)," *Weed Tech.* 4:97-104, The Weed Science Society of America, United States (1990).
Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).
Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).
Burke, I.C., et al., "CGA-362622 Antagonizes Annual Grass Control with Clethodim," *Weed Tech.* 16:749-754, The Weed Science Society of America, United States (2002).
Flint, J.L., et al., "Analyzing Herbicide Interactions, A Statistical Treatment of Colby's Method," *Weed Tech.* 2:304-309, The Weed Science Society of America, United States (1988).
Gillespie, G.R., and Nalewaja, J.D., "Wheat (*Triticum aestivum*) Response to Triallate Plus Chlorsulfuron," *Weed Tech.* 3:20-23, The Weed Science Society of America, United States (1989).
Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Harker, N.K., and O'Sullivan, P.A., "Synergistic Mixtures of Sethoxydim and Fluazifop on Annual Grass Weeds," *Weed Tech.* 5:310-316, The Weed Science Society of America, United States (1991).
Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).
Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).
Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).
Norris, J.L., et al., "Weed Control from Herbicide Combinations with Three Formulations of Glyphosate," *Weed Tech.* 15:552-558, The Weed Science Society of America, United States (2001).
Novosel, K.M., et al., "Metolachlor Efficacy as Influenced by Three Acetolactate Synthase-Inhibiting Herbicides," *Weed Tech.* 12:248-253, The Weed Science Society of America, United States (1998).
Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).
Salzman, F.P., and Renner, K.A., "Response of Soybean to Combinations of Clomazone, Metribuzin, Linuron, Alachlor, and Atrazine," *Weed Tech.* 6:922-929, The Weed Science Society of America, United States (1992).
Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).
Shaw, D.R. and Arnold, J.C., "Weed Control from Herbicide Combinations with Glyphosate," *Weed Tech.* 16:1-6, The Weed Science Society of America, United States (2002).
Snipes, C.E., and Allen, R.L., "Interaction of Graminicides Applied in Combination with Pyrithiobac," *Weed Tech.* 10:889-892, The Weed Science Society of America, United States (1996).
Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).
Zhang, W., et al., "Fenoxaprop Interactions for Barnyardgrass (*Echinochloa crus-galli*) Control in Rice," *Weed Tech.* 19:293-297, The Weed Science Society of America, United States (2005).
Rummens, F.H.A., "An Improved Definition of Synergistic and Antagonistic Effects," *Weed Science* 23(1):4-6, The Weed Science Society of America, United States (1975).
Prosecution History of European Patent Appl. No. 03735610.2 (European Counterpart of U.S. Appl. No. 10/518,742), Jul. 13, 2006-Sep. 25, 2009.
Partial English language translation of Prosecution History of European Patent Appl. No. 03735610.2, Jul. 13, 2006-Sep. 25, 2009.
Opposition Proceeding in European Patent No. EP-B-1482798, Mar. 5, 2007-Nov. 9, 2009.
Partial English language translation of Opposition Proceeding in European Patent No. EP-B-1482798, Feb. 26, 2007-Nov. 9, 2009.
Tomlin, C., ed, *The Pesticide Manual*, 1242-1245, British Crop Protection Council, Farnham, UK (1997).
"Metominostrobin data sheet," Compendium of Pesticide Common Names, accessed at http://www.alanwood.net/pesticides/metominostrobin.html, accessed on Apr. 8, 2009, 1 page.
"Azoxystrobin data sheet," Compendium of Pesticide Common Names, accessed at http://www.alanwood.net/pesticides/azoxystrobin.html, accessed on Apr. 8, 2009, 1 page.
NPL43 "Kresoxim-methyl data sheet," Compendium of Pesticide Common Names, accessed at http://www.alanwood.net/pesticides/kresoxim-methyl.html, accessed on Apr. 8, 2009, 1 page.
Office Action dated Jan. 4, 2011, in U.S. Appl. No. 11/997,079, inventor Dahmen, P., filed Jul. 28, 2008.

(56) References Cited

OTHER PUBLICATIONS

Hirt, E.E., Office Action for U.S. Appl. No. 11/916,436, inventors: Dunkel et al., § 371(c) Date: Nov. 7, 2008, U.S. Patent and Trademark Office, Alexandria, Virginia, dated Jul. 18, 2011.
European Search Report and Written Opinion for European Patent Application No. 10 163 282.6, European Patent Office, Munich, Germany, dated Feb. 2, 2011.
Unverified English translation of text portion of European Search Report and Written Opinion for European Patent Application No. 10 163 282.6, European Patent Office, Munich, Germany, dated Feb. 2, 2011.
Unverified English translation of claims of corresponding European Patent Application No. 10 163 282.6, filed Sep. 28, 2004, European Patent Office, Munich, Germany.
Hirt, E.E., Office Action for U.S. Appl. No. 11/916,436, Inventors: Dunkel et al., § 371(c) Date: Nov. 7, 2008, U.S. Patent and Trademark Office, Alexandria, Virginia, dated Jan. 30, 2012.
Holt, A.M., Office Action for U.S. Appl. No. 13/100,464, Inventors: Dahmen et al., filed May 4, 2011, U.S. Patent and Trademark Office, Alexandria, Virginia, dated May 4, 2012.
Dekeyser, M. and Davis, R.A., "Synthesis and Antifungal Activity of 5,6 Dihydro-3-methyl-1, 4-dioxin-2-carboxamides" *J. Agric. Food. Chem.* 46:287-2829 (1998).

SYNERGISTIC FUNGICIDAL ACTIVE SUBSTANCE COMBINATIONS

The present invention relates to novel active compound combinations comprising firstly known carboxamides and secondly further known fungicidally active compounds, which novel active compound combinations are highly suitable for controlling unwanted phytopathogenic fungi.

It is already known that certain carboxamides have fungicidal properties. Thus, for example, N-(3',4'-dichloro-5-fluoro-1,1'-biphenyl-2-yl)-3-(difluoromethyl)-1-methyl-1H-pyrazole-4-carboxamide is known from DE-A 102 15 292, 3-(trifluoromethyl)-N-{3'-fluoro-4'-[(E)-(methoxyimino)methyl]-1,1'-biphenyl-2-yl}-1-methyl-1H-pyrazole-4-carboxamide is known from WO 02/08197 and N-(3',4'-dichloro-1,1'-biphenyl-2-yl)-5-fluoro-1,3-dimethyl-1H-pyrazole-4-carboxamide is known WO 00/14701. The activity of these compounds is good; however, at low application rates it is sometimes unsatisfactory. Furthermore, it is already known that numerous triazole derivatives, aniline derivatives, dicarboximides and other heterocycles can be used for controlling fungi (cf. EP-A 0 040 345, DE-A 22 01 063, DE-A 23 24 010, Pesticide Manual, 9th Edition (1991), pages 249 and 827, EP-A 0 382 375 and EP-A 0 515 901). However, the action of these compounds is likewise not always sufficient at low application rates. Furthermore, it is already known that 1-(3,5-dimethylisoxazole-4-sulphonyl)-2-chloro-6,6-difluoro-[1,3]-dioxolo-[4,5f]-benzimidazole has fungicidal properties (cf. WO 97/06171). Finally, it is also known that substituted halopyrimidines have fungicidal properties (cf. DE-A1-196 46 407, EP-B 0 712 396).

The present invention now provides novel active compound combinations having very good fungicidal properties and comprising a carboxamide of the general formula (I) (group 1)

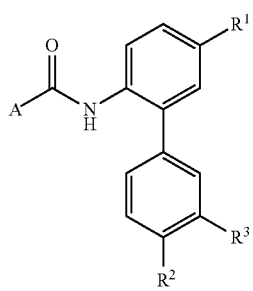

(I)

in which

R¹ represents hydrogen or fluorine,

R² represents halogen, $C_1$-$C_3$-alkyl, $C_1$-$C_3$-haloalkyl having 1 to 7 fluorine, chlorine and/or bromine atoms, $C_1$-$C_3$-alkoxy, $C_1$-$C_3$-haloalkoxy having 1 to 7 fluorine, chlorine and/or bromine atoms or represents —C(R⁴)=N—OR⁵, R³ represents hydrogen, halogen, $C_1$-$C_3$-alkyl or $C_1$-$C_3$-haloalkyl having 1 to 7 fluorine, chlorine and/or bromine atoms, R⁴ represents hydrogen or methyl, R⁵ represents $C_1$-$C_5$-alkyl, $C_1$-$C_5$-alkenyl or $C_1$-$C_5$-alkynyl, A represents one of the radicals A1 to A7 below:

A1

A2

A3

A4

A5

A6

A7

R⁶ represents $C_1$-$C_3$-alkyl,

R⁷ represents hydrogen, halogen, $C_1$-$C_3$-alkyl or $C_1$-$C_3$-haloalkyl having 1 to 7 fluorine, chlorine and/or bromine atoms, R⁸ represents hydrogen, halogen or $C_1$-$C_3$-alkyl, R⁹ represents hydrogen, halogen, $C_1$-$C_3$-alkyl, amino, mono- or di($C_1$-$C_3$-alkyl)amino, R¹⁰ represents hydrogen, halogen, $C_1$-$C_3$-alkyl or $C_1$-$C_3$-haloalkyl having 1 to 7 fluorine, chlorine and/or bromine atoms, R¹¹ represents halogen, $C_1$-$C_3$-alkyl or $C_1$-$C_3$-haloalkyl having 1 to 7 fluorine, chlorine and/or bromine atoms, R¹² represents halogen, $C_1$-$C_3$-alkyl or $C_1$-$C_3$-haloalkyl having 1 to 7 fluorine, chlorine and/or bromine atoms, R¹³ represents hydrogen, halogen, $C_1$-$C_3$-alkyl or $C_1$-$C_3$-haloalkyl having 1 to 7 fluorine, chlorine and/or bromine atoms, and at least one active compound selected from groups (2) to (23) below:

Group (2) Strobilurins of the General Formula (II)

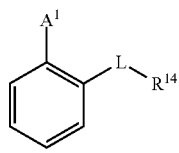

in which
A¹ represents one of the groups

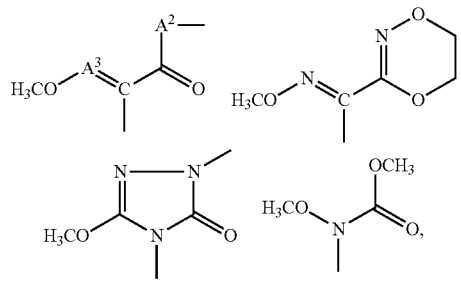

A² represents NH or O,
A³ represents N or CH,
L represents one of the groups

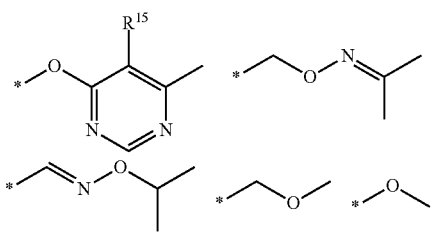

where the bond marked with an asterisk (*) is attached to the phenyl ring,
R¹⁴ represents phenyl, phenoxy or pyridinyl, each of which is optionally mono- or disubstituted by identical or different substituents from the group consisting of chlorine, cyano, methyl and trifluoromethyl, or represents 1-(4-chlorophenyl)-pyrazol-3-yl or represents 1,2-propane-dione-bis(O-methyloxime)-1-yl,
R¹⁵ represents hydrogen or fluorine;
Group (3) Triazoles of the General Formula (III)

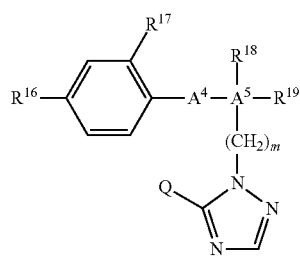

in which
Q represents hydrogen or SH,
m represents 0 or 1,
R¹⁶ represents hydrogen, fluorine, chlorine, phenyl or 4-chlorophenoxy,
R¹⁷ represents hydrogen or chlorine,
A⁴ represents a direct bond, —CH₂—, —(CH₂)₂— or —O—,
A⁴ furthermore represents *—CH₂—CHR²⁰— or *—CH=CR²⁰— where the bond marked with * is attached to the phenyl ring, and
R¹⁸ and R²⁰ furthermore together represent —CH₂—CH₂—CH[CH(CH₃)₂]— or —CH₂—CH₂—C(CH₃)₂—,
A⁵ represents C or Si (silicon),
A⁴ further represents —N(R²⁰)— and A⁵ furthermore together with R¹⁸ and R¹⁹ represents the group C=N—R²¹, in which case R²⁰ and R²¹ together represent the group

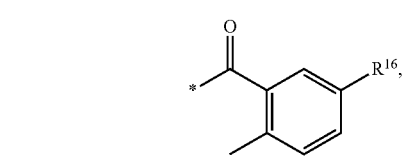

where the bond marked with * is attached to R²⁰,
R¹⁸ represents hydrogen, hydroxyl or cyano,
R¹⁹ represents 1-cyclopropylethyl, 1-chlorocyclopropyl, C₁-C₄-alkyl, C₁-C₆-hydroxyalkyl, C₁-C₄-alkylcarbonyl, C₁-C₂-haloalkoxy-C₁-C₂-alkyl, trimethylsilyl-C₁-C₂-alkyl, monofluorophenyl or phenyl,
R¹⁸ and R¹⁹ furthermore together represent —O—CH₂—CH(R²¹)—O—, —O—CH₂—CH(R²¹)—CH₂—, or —O—CH(2-chlorophenyl)-,
R²¹ represents hydrogen, C₁-C₄-alkyl or bromine;
Group (4) Sulphenamides of the General Formula (IV)

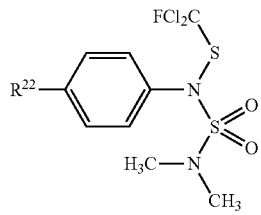

in which R²² represents hydrogen or methyl;
Group (5) Valinamides Selected from
(5-1) iprovalicarb
(5-2) N-[2-(4-{[3-(4-chlorophenyl)-2-propynyl]oxy}-3-methoxyphenyl)ethyl]-N²-(methylsulphonyl)-D-valinamide
(5-3) benthiavalicarb
Group (6) Carboxamides of the General Formula

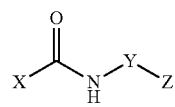

in which
X represents 2-chloro-3-pyridinyl, represents 1-methylpyrazol-4-yl which is substituted in the 3-position by methyl or trifluoromethyl and in the 5-position by hydrogen or chlorine, represents 4-ethyl-2-ethylamino-1,3-thiazol-5- yl, represents 1-methylcyclohexyl, represents 2,2-dichloro-1-ethyl-3-methylcyclopropyl, represents 2-fluoro-2-propyl or represents phenyl which is mono- to trisubstituted by identical or different substituents from the group consisting of chlorine and methyl, X furthermore represents 3,4-dichloroisothiazol-5-yl, 5,6-dihydro-2-methyl-1,4-oxathiin-3-yl, 4-methyl-1,2,3-thiadiazol-5-yl, 4,5-dimethyl-2-trimethylsilylthiophen-3-yl, 1-methylpyrrol-3-yl which is substituted in the 4-position by methyl or trifluoromethyl and in the 5-position by hydrogen or chlorine, Y represents a direct bond, $C_1$-$C_6$-alkanediyl (alkylene) which is optionally substituted by chlorine, cyano or oxo or represents thiophenediyl, Y furthermore represents $C_2$-$C_6$-alkenediyl (alkenylene), Z represents hydrogen or the group

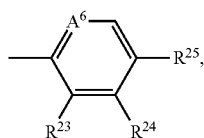

Z furthermore represents $C_1$-$C_6$-alkyl, $A^6$ represents CH or N, $R^{23}$ represents hydrogen, chlorine, phenyl which is optionally mono- or disubstituted by identical or different substituents from the group consisting of chlorine and di($C_1$-$C_3$-alkyl)aminocarbonyl, $R^{23}$ furthermore represents cyano or $C_1$-$C_6$-alkyl, $R^{24}$ represents hydrogen or chlorine, $R^{25}$ represents hydrogen, chlorine, hydroxyl, methyl or trifluoromethyl, $R^{25}$ furthermore represents di($C_1$-$C_3$-alkyl)aminocarbonyl, $R^{23}$ and $R^{24}$ furthermore together represent *—CH(CH$_3$)—CH$_2$—C(CH$_3$)$_2$— or *—CH(CH$_3$)—O—C(CH$_3$)$_2$— where the bond marked with * is attached to $R^{23}$;

Group (7) Dithiocarbamates Selected from
(7-1) mancozeb
(7-2) maneb
(7-3) metiram
(7-4) propineb
(7-5) thiram
(7-6) zineb
(7-7) ziram Group (8) Acylalanines of the General Formula (VI)

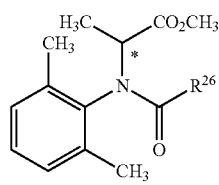

in which
* marks a carbon atom in the R or the S configuration, preferably in the S configuration,
$R^{26}$ represents benzyl, furyl or methoxymethyl;

Group (9): Anilinopyrimidines of the General Formula (VII)

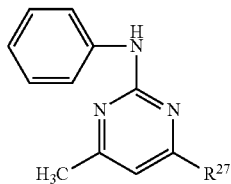

in which
$R^{27}$ represents methyl, cyclopropyl or 1-propynyl;

Group (10): Benzimidazoles of the General Formula (VIII)

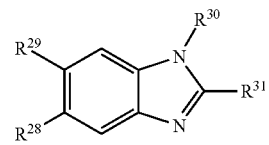

in which
$R^{28}$ and $R^{29}$ each represent hydrogen or together represent —O—CF$_2$—O—,
$R^{30}$ represents hydrogen, $C_1$-$C_4$-alkylaminocarbonyl or represents 3,5-dimethylisoxazol-4-ylsulphonyl,
$R^{31}$ represents chloro, methoxycarbonylamino, chlorophenyl, furyl or thiazolyl;

Group (11): Carbamates of the General Formula (IX)

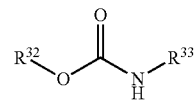

in which
$R^{32}$ represents n- or isopropyl,
$R^{33}$ represents di($C_1$-$C_2$-alkyl)amino-$C_2$-$C_4$-alkyl or diethoxyphenyl,
salts of these compounds also being included;

Group (12): Dicarboximides Selected from
(12-1) captafol
(12-2) captan
(12-3) folpet
(12-4) iprodione
(12-5) procymidone
(12-6) vinclozolin Group (13): Guanidines Selected from
(13-1) dodine
(13-2) guazatine
(13-3) iminoctadine triacetate
(13-4) iminoctadine tris(albesilate)

Group (14): Imidazoles Selected from
(14-1) cyazofamid
(14-2) prochloraz
(14-3) triazoxide
(14-4) pefurazoate Group (15): Morpholines of the General Formula (X)

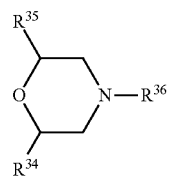

in which
$R^{34}$ and $R^{35}$ independently of one another represent hydrogen or methyl,
$R^{36}$ represents $C_1$-$C_{14}$-alkyl (preferably $C_{12}$-$C_{14}$-alkyl), $C_5$-$C_{12}$-cycloalkyl (preferably $C_{10}$-$C_{12}$-cycloalkyl), phenyl-$C_1$-$C_4$-alkyl, which may be substituted in the phenyl moiety by halogen or
$C_1$-$C_4$-alkyl or represents acrylyl which is substituted by chlorophenyl and dimethoxyphenyl;

Group (16): Pyrroles of the General Formula (XI)

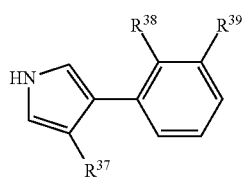

in which
$R^{37}$ represents chlorine or cyano,
$R^{38}$ represents chlorine or nitro,
$R^{39}$ represents chlorine,
$R^{38}$ and $R^{39}$ furthermore together represent —O—$CF_2$—O—;

Group (17): Phosphonates Selected from
(17-1) fosetyl-Al
(17-2) phosphonic acid;

Group (18): Phenylethanamides of the General Formula (XII)

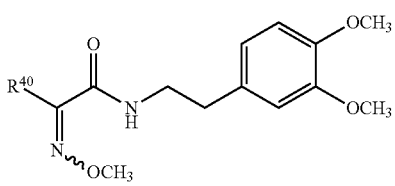

in which
$R^{40}$ represents unsubstituted or fluorine-, chlorine-, bromine-, methyl- or ethyl-substituted phenyl, 2-naphthyl, 1,2,3,4-tetrahydronaphthyl or indanyl;

Group (19): Fungicides Selected from
(19-1) acibenzolar-S-methyl
(19-2) chlorothalonil
(19-3) cymoxanil
(19-4) edifenphos
(19-5) famoxadone
(19-6) fluazinam
(19-7) copper oxychloride
(19-8) copper hydroxide
(19-9) oxadixyl
(19-10) spiroxamine
(19-11) dithianon
(19-12) metrafenone
(19-13) fenamidone
(19-14) 2,3-dibutyl-6-chlorothieno[2,3-d]pyrimidin-4(3H)-one
(19-15) probenazole
(19-16) isoprothiolane
(19-17) kasugamycin
(19-18) phthalide
(19-19) ferimzone
(19-20) tricyclazole
(19-21) N-({4-[(cyclopropylamino)carbonyl]phenyl}sulphonyl)-2-methoxybenzamide
(19-22) 2-(4-chlorophenyl)-N-{2-[3-methoxy-4-(prop-2-yn-1-yloxy)phenyl]ethyl}-2-(prop-2-yn-1-yloxy)acetamide Group (20): (Thio)Urea Derivatives Selected from
(20-1) pencycuron
(20-2) thiophanate-methyl
(20-3) thiophanate-ethyl Group (21): Amides of the General Formula (XIII)

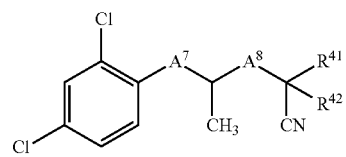

in which
$A^7$ represents a direct bond or —O—,
$A^8$ represents —C(=O)NH— or —NHC(=O)—,
$R^{41}$ represents hydrogen or $C_1$-$C_4$-alkyl,
$R^{42}$ represents $C_1$-$C_6$-alkyl;

Group (22): Triazolopyrimidines of the General Formula (XIV)

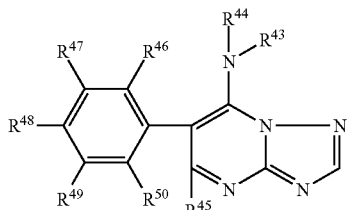

in which
$R^{43}$ represents $C_1$-$C_6$-alkyl or $C_2$-$C_6$-alkenyl,
$R^{44}$ represents $C_1$-$C_6$-alkyl,
$R^{43}$ and $R^{44}$ furthermore together represent $C_4$-$C_5$-alkanediyl (alkylene) which is mono- or disubstituted by $C_1$-$C_6$-alkyl,
$R^{45}$ represents bromine or chlorine,
$R^{46}$ and $R^{50}$ independently of one another represent hydrogen, fluorine, chlorine or methyl,
$R^{47}$ and $R^{49}$ independently of one another represent hydrogen or fluorine,
$R^{48}$ represents hydrogen, fluorine or methyl, Group (23): Iodochromones of the General Formula (XV)

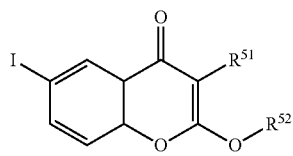

(XV)

in which
$R^{51}$ represents $C_1$-$C_6$-alkyl,
$R^{52}$ represents $C_1$-$C_6$-alkyl, $C_2$-$C_6$-alkenyl or $C_2$-$C_6$-alkynyl.

Surprisingly, the fungicidal action of the active compound combinations according to the invention is considerably better than the sum of the activities of the individual active compounds. Thus, an unforeseeable true synergistic effect is present, and not just an addition of actions.

The formula (I) provides a general definition of the compounds of group (1).

Preference is given to carboxamides of the formula (I) in which
$R^1$ represents hydrogen or fluorine,
$R^2$ represents fluorine, chlorine, bromine, iodine, methyl, trifluoromethyl, trifluoromethoxy or represents —C($R^4$)=N—O$R^5$,
$R^3$ represents hydrogen, fluorine, chlorine, bromine, methyl or trifluoromethyl,
$R^4$ represents hydrogen or methyl,
$R^5$ represents $C_1$-$C_5$-alkyl,
A represents one of the radicals A1 to A7 below:

$R^6$ represents methyl,
$R^7$ represents iodine, methyl, difluoromethyl or trifluoromethyl,
$R^8$ represents hydrogen, fluorine, chlorine or methyl,
$R^9$ represents hydrogen, chlorine, methyl, amino or dimethylamino,
$R^{10}$ represents methyl, difluoromethyl or trifluoromethyl,
$R^{11}$ represents chlorine, bromine, iodine, methyl, difluoromethyl or trifluoromethyl,
$R^{12}$ represents bromine or methyl,
$R^{13}$ represents methyl or trifluoromethyl.

Particular preference is given to carboxamides of the formula (I) in which
$R^1$ represents hydrogen or fluorine,
$R^2$ represents fluorine, chlorine, bromine, trifluoromethyl or represents —CH=N—OCH$_3$,
$R^3$ represents hydrogen, fluorine or chlorine,
A represents one of the radicals A1 to A5 below:

$R^6$ represents methyl,
$R^7$ represents methyl, difluoromethyl or trifluoromethyl,
$R^8$ represents hydrogen or fluorine,
$R^9$ represents methyl,
$R^{10}$ represents methyl, difluoromethyl or trifluoromethyl,
$R^{11}$ represents iodine, difluoromethyl or trifluoromethyl,
$R^{12}$ represents methyl,
$R^{13}$ represents methyl or trifluoromethyl.

Very particular preference is given to carboxamides of the formula (I) in which
$R^1$ represents hydrogen or fluorine,
$R^2$ represents fluorine, chlorine, bromine, trifluoromethyl or represents —CH=N—OCH$_3$,
$R^3$ represents hydrogen, fluorine or chlorine,
A represents one of the radicals A1 or A2 below:

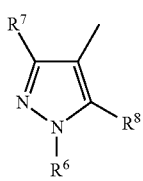
A1

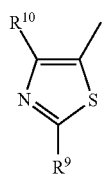
A2

$R^6$ represents methyl,
$R^7$ represents methyl, difluoromethyl or trifluoromethyl,
$R^8$ represents hydrogen or fluorine,
$R^9$ represents methyl,
$R^{10}$ represents methyl, difluoromethyl or trifluoromethyl.

Very particular preference is given to using, in mixtures, compounds of the formula (Ia)

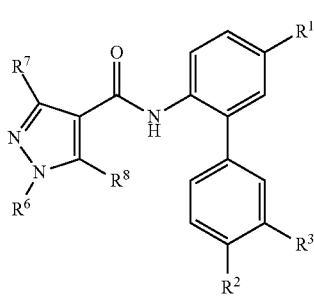
(Ia)

in which $R^1$, $R^2$, $R^3$, $R^6$, $R^7$ and $R^8$ are as defined above.

Very particular preference is given to using, in mixtures, compounds of the formula (Ib)

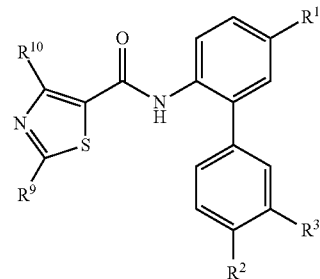
(Ib)

in which $R^1$, $R^2$, $R^3$, $R^9$ and $R^{10}$ are as defined above.

The formula (I) embraces in particular the following preferred mixing partners of group (1):
(1-1) N-(3',4'-dichloro-5-fluoro-1,1'-biphenyl-2-yl)-3-(difluoromethyl)-1-methyl-1H-pyrazole-4-carboxamide (known from WO 03/070705)
(1-2) 3-(difluoromethyl)-N-{3'-fluoro-4'-[(E)-(methoxyimino)methyl]-1,1'-biphenyl-2-yl}-1-methyl-1H-pyrazole-4-carboxamide (known from WO 02/08197)
(1-3) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197)
(1-4) N-(3',4'-dichloro-1,1'-biphenyl-2-yl)-5-fluoro-1,3-dimethyl-1H-pyrazole-4-carboxamide (known from WO 00/14701)
(1-5) N-(4'-chloro-3'-fluoro-1,1'-biphenyl-2-yl)-2-methyl-4-(trifluoromethyl)-1,3-thiazole-5-carboxamide (known from WO 03/066609)
(1-6) N-(4'-chloro-1,1'-biphenyl-2-yl)-4-(difluoromethyl)-2-methyl-1,3-thiazole-5-carboxamide (known from WO 03/066610)
(1-7) N-(4'-bromo-1,1'-biphenyl-2-yl)-4-(difluoromethyl)-2-methyl-1,3-thiazole-5-carboxamide (known from WO 03/066610)
(1-8) 4-(difluoromethyl)-2-methyl-N-[4'-(trifluoromethyl)-1,1'-biphenyl-2-yl]-1,3-thiazole-5-carboxamide (known from WO 03/066610)
(1-9) N-(4'-chloro-3'-fluoro-1,1'-biphenyl-2-yl)-4-(difluoromethyl)-2-methyl-1,3-thiazole-5-carboxamide (known from WO 03/066610)

Emphasis is given to active compound combinations according to the invention which, in addition to carboxamide (1-1) N-(3',4'-dichloro-5-fluoro-1,1'-biphenyl-2-yl)-3-(difluoromethyl)-1-methyl-1H-pyrazole-4-carboxamide (group 1) comprise one or more, preferably one, mixing partner of groups (2) to (23).

Emphasis is given to active compound combinations according to the invention which, in addition to carboxamide (1-7) N-(4'-bromo-1,1'-biphenyl-2-yl)-4-(difluoromethyl)-2-methyl-1,3-thiazole-5-carboxamide (group 1) comprise one or more, preferably one, mixing partner of groups (2) to (23).

Emphasis is given to active compound combinations according to the invention which, in addition to carboxamide (1-8) 4-(difluoromethyl)-2-methyl-N-[4'-(trifluoromethyl)-1,1'-biphenyl-2-yl]-1,3-thiazole-5-carboxamide (group 1) comprise one or more, preferably one, mixing partner of groups (2) to (23).

Emphasis is given to active compound combinations according to the invention which, in addition to carboxamide (1-9) N-(4'-chloro-3'-fluoro-1,1'-biphenyl-2-yl)-4-(difluoromethyl)-2-methyl-1,3-thiazole-5-carboxamide (group 1) comprise one or more, preferably one, mixing partner of groups (2) to (23).

The formula (II) embraces the following preferred mixing partners of group (2):

(2-1) azoxystrobin (known from EP-A 0 382 375) of the formula

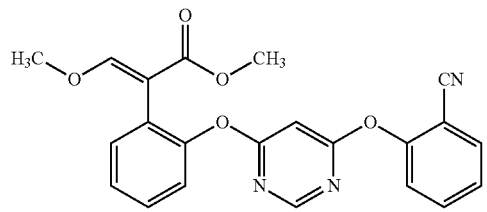 [SMILES: CO/C=C(/C(=O)OC)c1ccccc1Oc1cc(Oc2ccccc2C#N)ncn1]

(2-2) fluoxastrobin (known from DE-A 196 02 095) of the formula

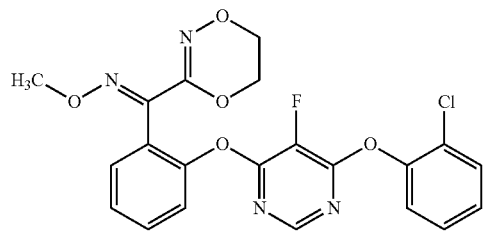 [SMILES: CO/N=C(/C1=NOCCO1)c1ccccc1Oc1ncnc(Oc2ccccc2Cl)c1F]

(2-3) (2E)-2-(2-{[6-(3-chloro-2-methylphenoxy)-5-fluoro-4-pyrimidinyl]oxy}phenyl)-2-(methoxy-imino)-N-methylethanamide (known from DE-A 196 46 407, EP-B 0 712 396) of the formula

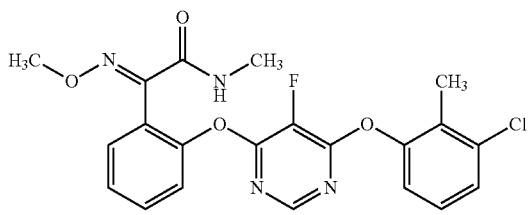 [SMILES: CNC(=O)/C(=N/OC)c1ccccc1Oc1ncnc(Oc2cccc(Cl)c2C)c1F]

(2-4) trifloxystrobin (known from EP-A 0 460 575) of the formula

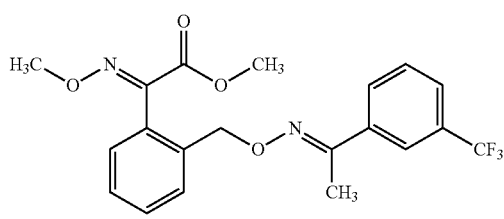 [SMILES: CO/N=C(/C(=O)OC)c1ccccc1CO/N=C(\C)c1cccc(C(F)(F)F)c1]

(2-5) (2E)-2-(methoxyimino)-N-methyl-2-(2-{[({(1E)-1-[3-(trifluoromethyl)phenyl]ethylidene}-amino)oxy]methyl}phenyl)ethanamide (known from EP-A 0 569 384) of the formula

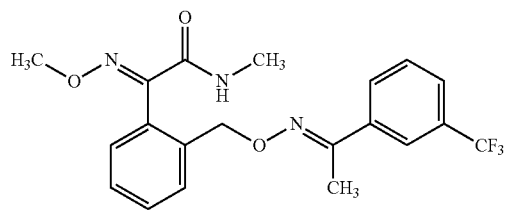 [SMILES: CNC(=O)/C(=N/OC)c1ccccc1CO/N=C(\C)c1cccc(C(F)(F)F)c1]

(2-6) (2E)-2-(methoxyimino)-N-methyl-2-{2-[(E)-({1-[3-(trifluoromethyl)phenyl]ethoxy}imino)-methyl]phenyl}ethanamide (known from EP-A 0 596 254) of the formula

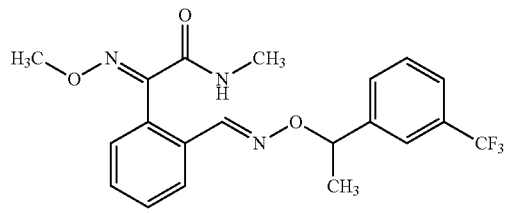 [SMILES: CNC(=O)/C(=N/OC)c1ccccc1/C=N/OC(C)c1cccc(C(F)(F)F)c1]

(2-7) orysastrobin (known from DE-A 195 39 324) of the formula

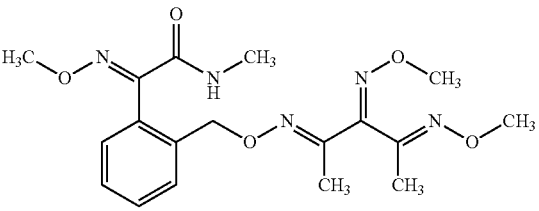

(2-8) 5-methoxy-2-methyl-4-(2-{[({(1E)-1-[3-(trifluoromethyl)phenyl]ethylidene}amino)oxy]-methyl}phenyl)-2,4-dihydro-3H-1,2,4-triazol-3-one (known from WO 98/23155) of the formula

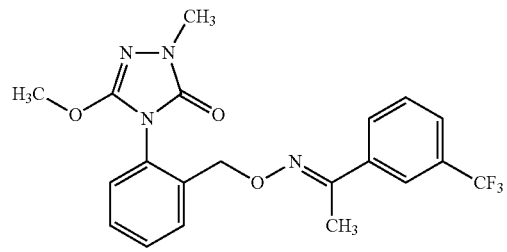 [SMILES: COc1nn(C)c(=O)n1-c1ccccc1CO/N=C(\C)c1cccc(C(F)(F)F)c1]

(2-9) kresoxim-methyl (known from EP-A 0 253 213) of the formula

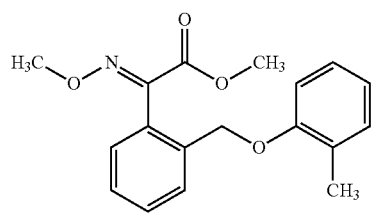 [SMILES: CO/N=C(/C(=O)OC)c1ccccc1COc1ccccc1C]

(2-10) dimoxystrobin (known from EP-A 0 398 692) of the formula

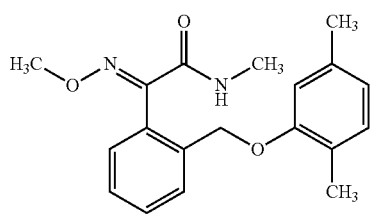 [SMILES: CNC(=O)/C(=N/OC)c1ccccc1COc1cc(C)ccc1C]

(2-11) picoxystrobin (known from EP-A 0 278 595) of the formula

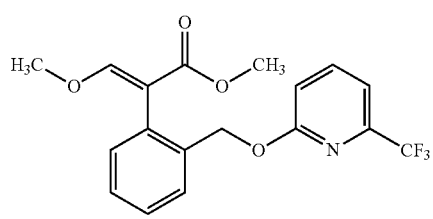 [SMILES: CO/C=C(/C(=O)OC)c1ccccc1COc1cccc(C(F)(F)F)n1]

(2-12) pyraclostrobin (known from DE-A 44 23 612) of the formula

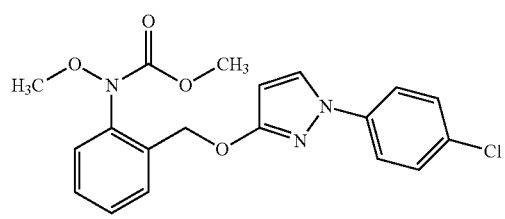 [SMILES: COC(=O)N(OC)c1ccccc1COc1ccn(-c2ccc(Cl)cc2)n1]

(2-13) metominostrobin (known from EP-A 0 398 692) of the formula

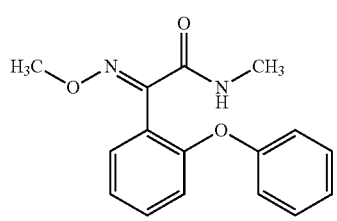 [SMILES: CNC(=O)/C(=N/OC)c1ccccc1Oc1ccccc1]

The formula (III) embraces the following preferred mixing partners of group (3):
(3-1) azaconazole (known from DE-A 25 51 560) of the formula

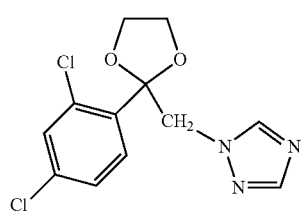 [SMILES: Clc1ccc(C2(Cn3cncn3)OCCO2)c(Cl)c1]

(3-2) etaconazole (known from DE-A 25 51 560) of the formula

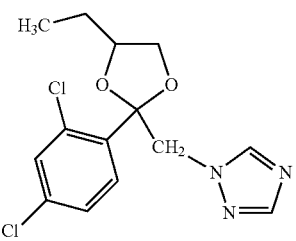 [SMILES: CCC1COC(Cn2cncn2)(c2ccc(Cl)cc2Cl)O1]

(3-3) propiconazole (known from DE-A 25 51 560) of the formula

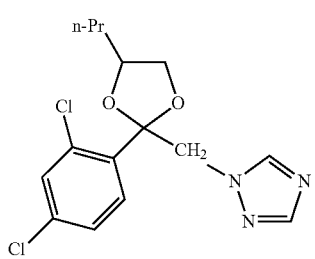

(3-4) difenoconazole (known from EP-A 0 112 284) of the formula

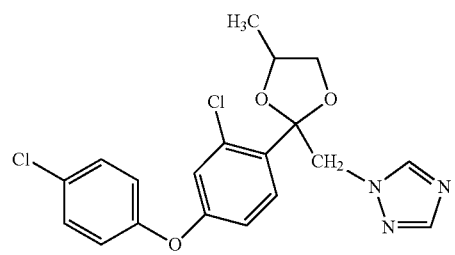 [SMILES: CC1COC(Cn2cncn2)(c2ccc(Oc3ccc(Cl)cc3)cc2Cl)O1]

(3-5) bromuconazole (known from EP-A 0 258 161) of the formula

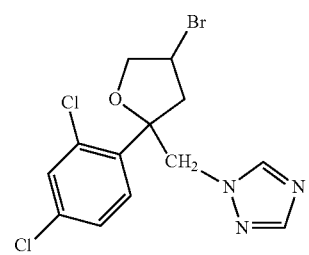 [SMILES: Clc1ccc(C2(Cn3cncn3)CC(Br)CO2)c(Cl)c1]

(3-6) cyproconazole (known from DE-A 34 06 993) of the formula

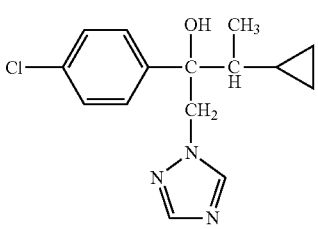 [SMILES: CC(C1CC1)C(O)(Cn1cncn1)c1ccc(Cl)cc1]

(3-7) hexaconazole (known from DE-A 30 42 303) of the formula

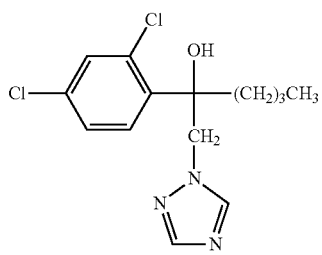

(3-8) penconazole (known from DE-A 27 35 872) of the formula

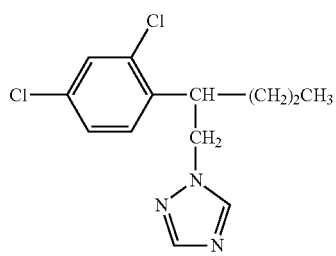

(3-9) myclobutanil (known from EP-A 0 145 294) of the formula

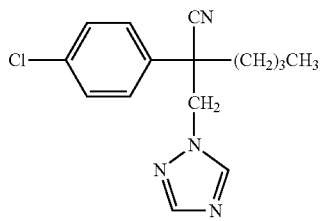

(3-10) tetraconazole (known from EP-A 0 234 242) of the formula

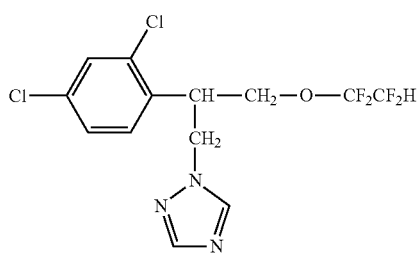

(3-11) flutriafol (known from EP-A 0 015 756) of the formula

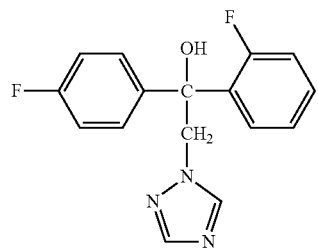 [SMILES: OC(Cn1cncn1)(c1ccc(F)cc1)c1ccccc1F]

(3-12) epoxiconazole (known from EP-A 0 196 038) of the formula

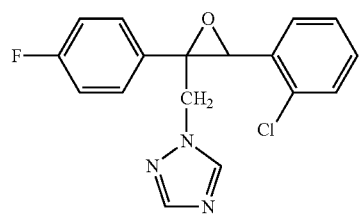 [SMILES: Fc1ccc(C2(Cn3cncn3)OC2c2ccccc2Cl)cc1]

(3-13) flusilazole (known from EP-A 0 068 813) of the formula

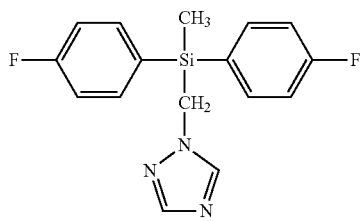 [SMILES: C[Si](Cn1cncn1)(c1ccc(F)cc1)c1ccc(F)cc1]

(3-14) simeconazole (known from EP-A 0 537 957) of the formula

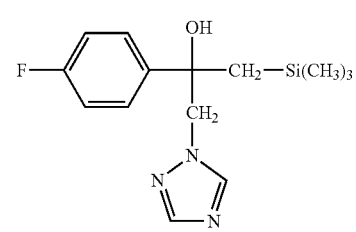

(3-15) prothioconazole (known from WO 96/16048) of the formula

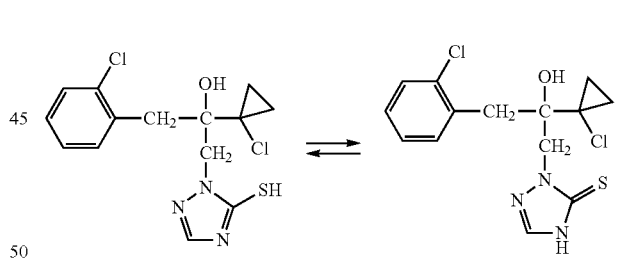

(3-16) fenbuconazole (known from DE-A 37 21 786) of the formula

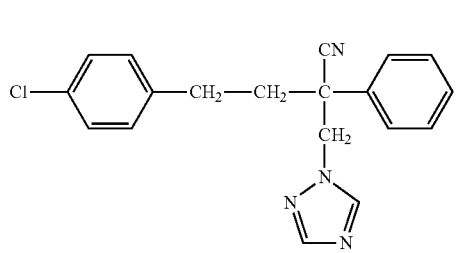 [SMILES: N#CC(CCc1ccc(Cl)cc1)(Cn1cncn1)c1ccccc1]

(3-17) tebuconazole (known from EP-A 0 040 345) of the formula

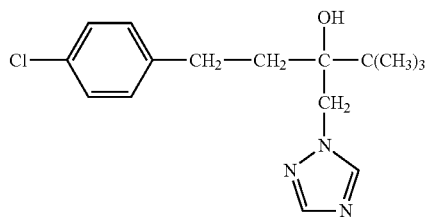 [SMILES: CC(C)(C)C(O)(CCc1ccc(Cl)cc1)Cn1cncn1]

(3-18) ipconazole (known from EP-A 0 329 397) of the formula

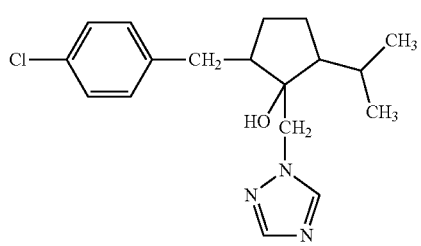 [SMILES: CC(C)C1CCC(Cc2ccc(Cl)cc2)C1(O)Cn1cncn1]

(3-19) metconazole (known from EP-A 0 329 397) of the formula

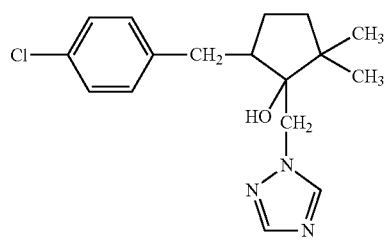 [SMILES: CC1(C)CCC(Cc2ccc(Cl)cc2)C1(O)Cn1cncn1]

(3-20) triticonazole (known from EP-A 0 378 953) of the formula

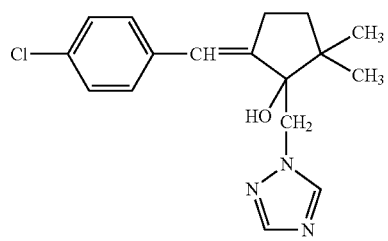 [SMILES: CC1(C)CCC(=Cc2ccc(Cl)cc2)C1(O)Cn1cncn1]

(3-21) bitertanol (known from DE-A 23 24 010) of the formula

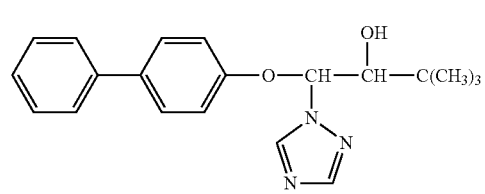 [SMILES: CC(C)(C)C(O)C(Oc1ccc(-c2ccccc2)cc1)n1cncn1]

(3-22) triadimenol (known from DE-A 23 24 010) of the formula

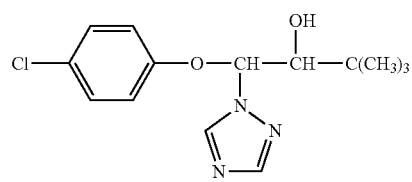 [SMILES: CC(C)(C)C(O)C(Oc1ccc(Cl)cc1)n1cncn1]

(3-23) triadimefon (known from DE-A 22 01 063) of the formula

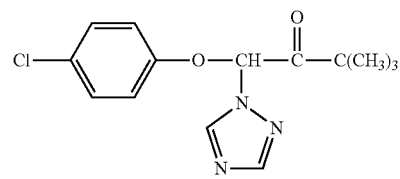 [SMILES: CC(C)(C)C(=O)C(Oc1ccc(Cl)cc1)n1cncn1]

(3-24) fluquinconazole (known from EP-A 0 183 458) of the formula

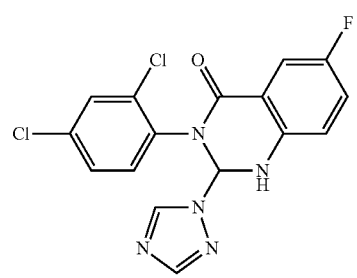 [SMILES: O=C1c2cc(F)ccc2NC(n2cncn2)N1c1ccc(Cl)cc1Cl]

(3-25) quinconazole (known from EP-A 0 183 458) of the formula

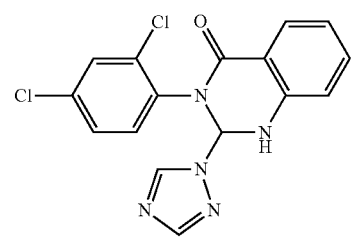 [SMILES: O=C1c2ccccc2NC(n2cncn2)N1c1ccc(Cl)cc1Cl]

The formula (IV) embraces the following preferred mixing partners of group (4):

(4-1) dichlofluanid (known from DE-A 11 93 498) of the formula

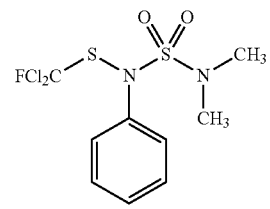

(4-2) tolylfluanid (known from DE-A 11 93 498) of the formula

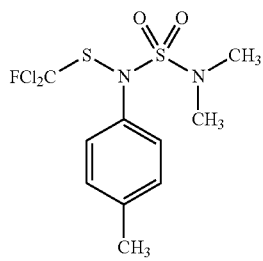

Preferred mixing partners of group (5) are
(5-1) iprovalicarb (known from DE-A 40 26 966) of the formula

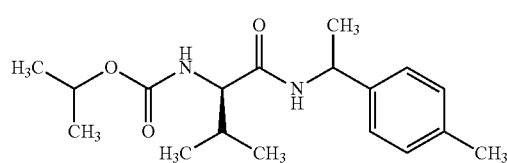 [SMILES: Cc1ccc(C(C)NC(=O)[C@H](NC(=O)OC(C)C)C(C)C)cc1]

(5-3) benthiavalicarb (known from WO 96/04252) of the formula

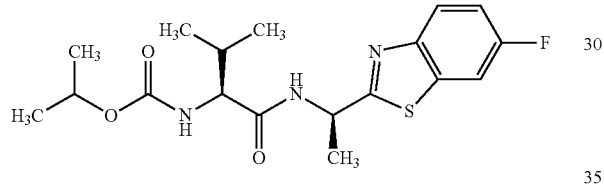

The formula (V) embraces the following preferred mixing partners of group (6):
(6-1) 2-chloro-N-(1,1,3-trimethylindan-4-yl)nicotinamide (known from EP-A 0 256 503) of the formula

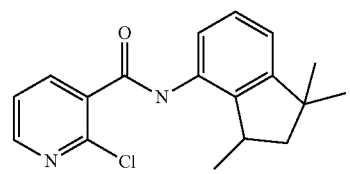 [SMILES: CC1CC(C)(C)c2cccc(NC(=O)c3cccnc3Cl)c21]

(6-2) boscalid (known from DE-A 195 31 813) of the formula

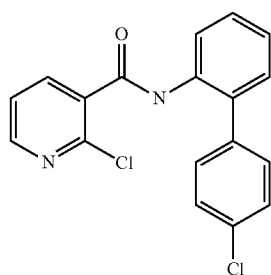 [SMILES: O=C(Nc1ccccc1-c1ccc(Cl)cc1)c1cccnc1Cl]

(6-3) furametpyr (known from EP-A 0 315 502) of the formula (6-4) N-(3-p-tolylthiophen-2-yl)-1-methyl-3-trifluoromethyl-1H-pyrazole-4-carboxamide (known from EP-A 0 737 682) of the formula

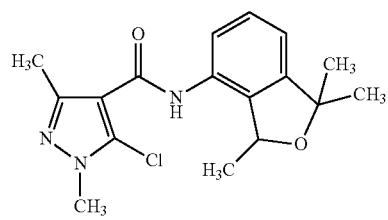

(6-5) ethaboxam (known from EP-A 0 639 574) of the formula

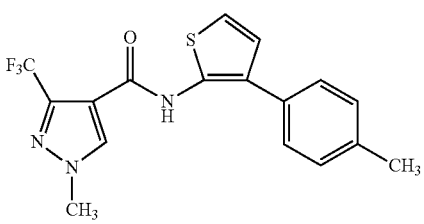 [SMILES: Cc1ccc(-c2ccsc2NC(=O)c2cn(C)nc2C(F)(F)F)cc1]

(6-6) fenhexamid (known from EP-A 0 339 418) of the formula

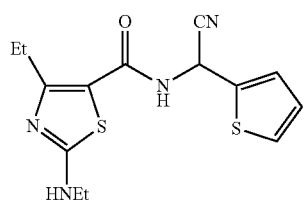

(6-7) carpropamid (known from EP-A 0 341 475) of the formula

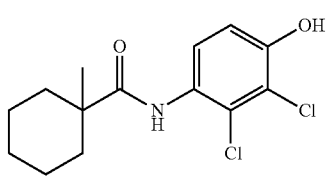 [SMILES: CC1(C(=O)Nc2ccc(O)c(Cl)c2Cl)CCCCC1]

(6-8) 2-chloro-4-(2-fluoro-2-methylpropionylamino)-N,N-dimethylbenzamide (known from EP-A 0 600 629) of the formula

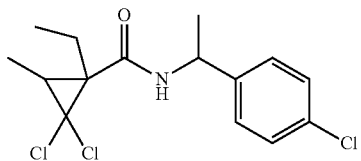 [SMILES: CCC1(C(=O)NC(C)c2ccc(Cl)cc2)C(C)C1(Cl)Cl]

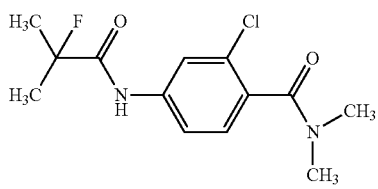 [SMILES: CN(C)C(=O)c1ccc(NC(=O)C(C)(C)F)cc1Cl]

(6-9) picobenzamid (known from WO 99/42447) of the formula

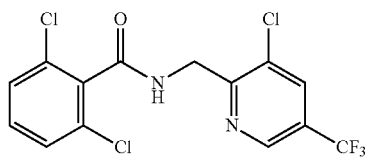 [SMILES: O=C(NCc1ncc(C(F)(F)F)cc1Cl)c1c(Cl)cccc1Cl]

(6-10) zoxamide (known from EP-A 0 604 019) of the formula

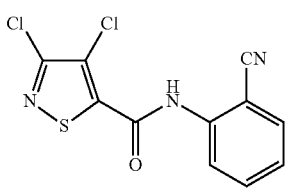 [SMILES: N#Cc1ccccc1NC(=O)c1snc(Cl)c1Cl]

(6-11) 3,4-dichloro-N-(2-cyanophenyl)isothiazole-5-carboxamide (known from WO 99/24413) of the formula

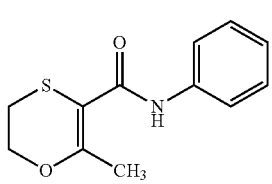 [SMILES: CC1=C(C(=O)Nc2ccccc2)SCCO1]

(6-12) carboxin (known from U.S. Pat. No. 3,249,499) of the formula (6-13) tiadinil (known from U.S. Pat. No. 6,616,054) of the formula

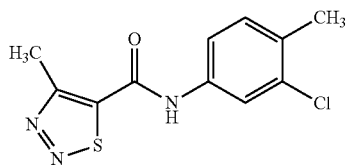 [SMILES: Cc1ccc(NC(=O)c2snnc2C)cc1Cl]

(6-14) penthiopyrad (known from EP-A 0 737 682) of the formula (6-15) silthiofam (known from WO 96/18631) of the formula

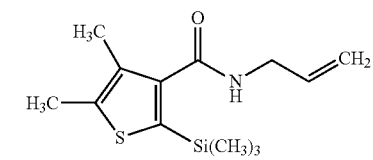

(6-16) N-[2-(1,3-dimethylbutyl)phenyl]-1-methyl-4-(trifluoromethyl)-1H-pyrrole-3-carboxamide (known from WO 02/38542) of the formula Preferred mixing partners of group (7) are (7-1) mancozeb (known from DE-A 12 34 704) having the IUPAC name manganese ethylenebis(dithiocarbamate) (polymeric) complex with zinc salt (7-2) maneb (known from U.S. Pat. No. 2,504,404) of the formula

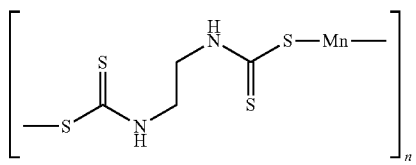

(7-3) metiram (known from DE-A 10 76 434) having the IUPAC name zinc ammoniate ethylenebis(dithiocarbamate)-poly(ethylenethiuram disulphide)

(7-4) propineb (known from GB 935 981) of the formula

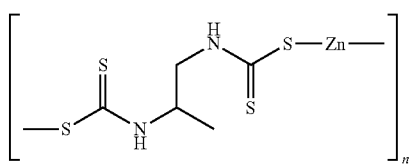

(7-5) thiram (known from U.S. Pat. No. 1,972,961) of the formula

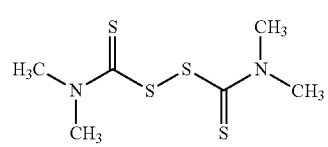

(7-6) zineb (known from DE-A 10 81 446) of the formula

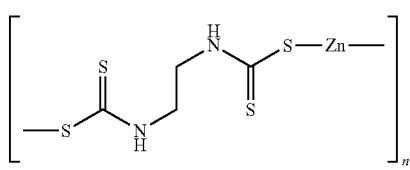

(7-7) ziram (known from U.S. Pat. No. 2,588,428) of the formula

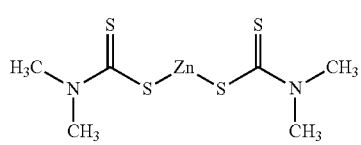

The formula (VI) embraces the following preferred mixing partners of group (8):

(8-1) benalaxyl (known from DE-A 29 03 612) of the formula

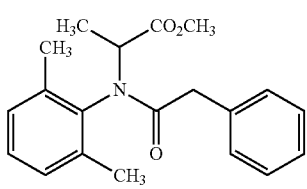

(8-2) furalaxyl (known from DE-A 25 13 732) of the formula

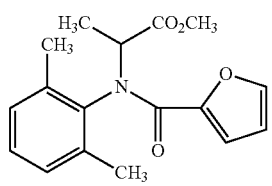

(8-3) metalaxyl (known from DE-A 25 15 091) of the formula

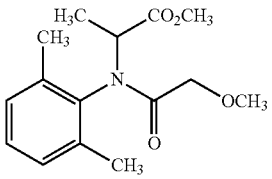 [SMILES: COCC(=O)N(c1c(C)cccc1C)C(C)C(=O)OC]

(8-4) metalaxyl-M (known from WO 96/01559) of the formula

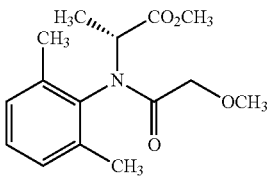

(8-5) benalaxyl-M of the formula

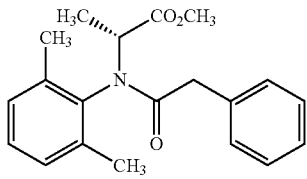

The formula (VII) embraces the following preferred mixing partners of group (9):

(9-1) cyprodinil (known from EP-A 0 310 550) of the formula

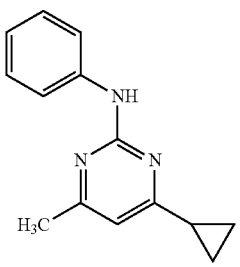 [SMILES: Cc1cc(C2CC2)nc(Nc2ccccc2)n1]

(9-2) mepanipyrim (known from EP-A 0 270 111) of the formula

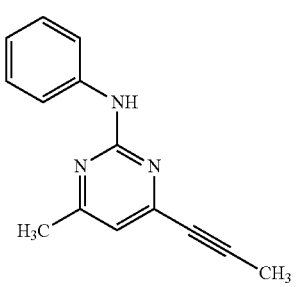 [SMILES: CC#Cc1cc(C)nc(Nc2ccccc2)n1]

(9-3) pyrimethanil (known from DD 151 404) of the formula

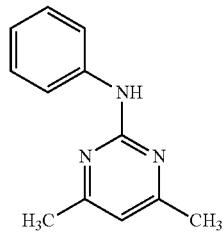

The formula (VIII) embraces the following preferred mixing partners of group (10):

(10-1) 6-chloro-5-[(3,5-dimethylisoxazol-4-yl)sulphonyl]-2,2-difluoro-5H-[1,3]dioxolo[4,5-f]-benzimidazole (known from WO 97/06171) of the formula

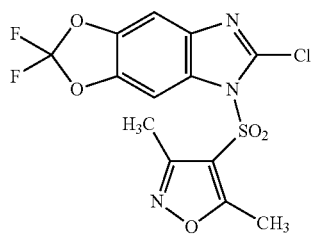 [SMILES: Cc1noc(C)c1S(=O)(=O)n1c(Cl)nc2cc3c(cc21)OC(F)(F)O3]

(10-2) benomyl (known from U.S. Pat. No. 3,631,176) of the formula

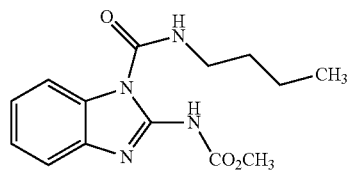 [SMILES: CCCCNC(=O)n1c(NC(=O)OC)nc2ccccc21]

(10-3) carbendazim (known from U.S. Pat. No. 3,010,968) of the formula

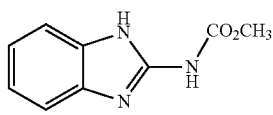

(10-4) chlorfenazole of the formula

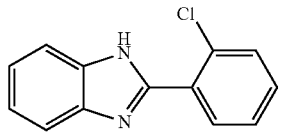 [SMILES: Clc1ccccc1-c1nc2ccccc2[nH]1]

(10-5 fuberidazole (known from DE-A 12 09 799) of the formula

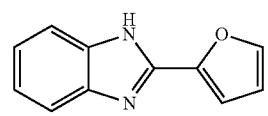 [SMILES: c1coc(-c2nc3ccccc3[nH]2)c1]

(10-6) thiabendazole (known from U.S. Pat. No. 3,206,468) of the formula

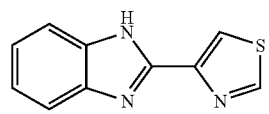 [SMILES: c1ccc2[nH]c(-c3cscn3)nc2c1]

The formula (IX) embraces the following preferred mixing partners of group (11):

(11-1) diethofencarb (known from EP-A 0 078 663) of the formula

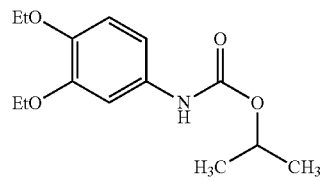

(11-2) propamocarb (known from U.S. Pat. No. 3,513,241) of the formula

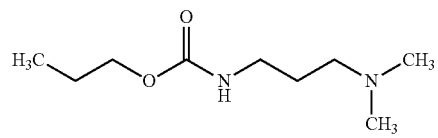

(11-3) propamocarb-hydrochloride (known from U.S. Pat. No. 3,513,241) of the formula

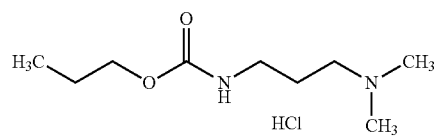

(11-4) propamocarb-fosetyl of the formula

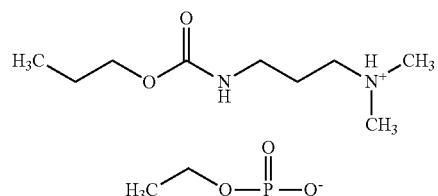

Preferred mixing partners of group (12) are
(12-1) captafol (known from U.S. Pat. No. 3,178,447) of the formula (12-2) captan (known from U.S. Pat. No. 2,553,770) of the formula

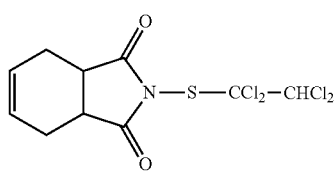

(12-3) folpet (known from U.S. Pat. No. 2,553,770) of the formula

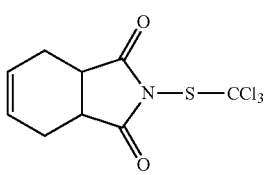

(12-4) iprodione (known from DE-A 21 49 923) of the formula

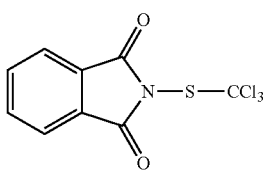

(12-5) procymidone (known from DE-A 20 12 656) of the formula

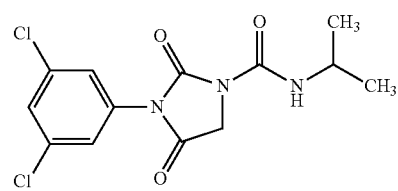 [SMILES: CC(C)NC(=O)N1CC(=O)N(c2cc(Cl)cc(Cl)c2)C1=O]

(12-6) vinclozolin (known from DE-A 22 07 576) of the formula

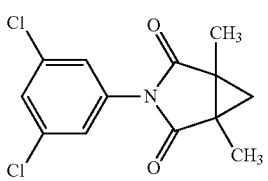 [SMILES: CC12CC1(C)C(=O)N(c1cc(Cl)cc(Cl)c1)C2=O]

Preferred mixing partners of group (13) are
(13-1) dodine (known from GB 11 03 989) of the formula

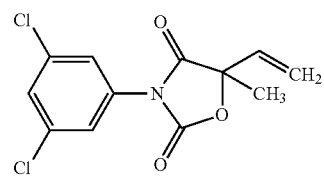 [SMILES: C=CC1(C)OC(=O)N(c2cc(Cl)cc(Cl)c2)C1=O]

(13-2) guazatine (known from GB 11 14 155)
(13-3) iminoctadine triacetate (known from EP-A 0 155 509) of the formula

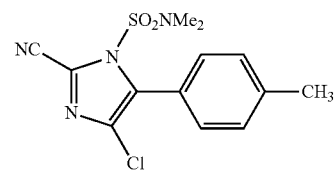

Preferred mixing partners of the group (14) are
(14-1) cyazofamid (known from EP-A 0 298 196) of the formula

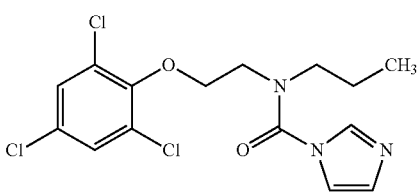 [SMILES: CCCN(CCOc1c(Cl)cc(Cl)cc1Cl)C(=O)n1ccnc1]

(14-2) prochloraz (known from DE-A 24 29 523) of the formula

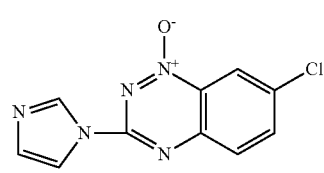 [SMILES: [O-][n+]1nc(-n2ccnc2)nc2ccc(Cl)cc21]

(14-3) triazoxide (known from DE-A 28 02 488) of the formula (14-4) pefurazoate (known from EP-A 0 248 086) of the formula

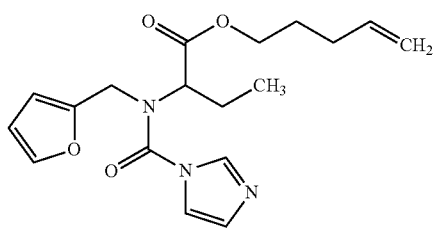 [SMILES: C=CCCCOC(=O)C(CC)N(Cc1ccco1)C(=O)n1ccnc1]

The formula (X) embraces the following preferred mixing partners of group (15):
(15-1) aldimorph (known from DD 140 041) of the formula

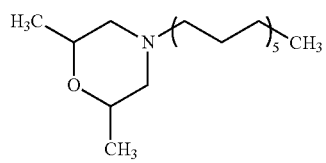

(15-2) tridemorph (known from GB 988 630) of the formula

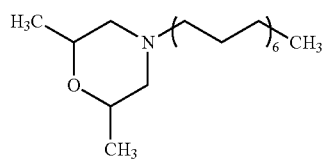

(15-3) dodemorph (known from DE-A 25 432 79) of the formula

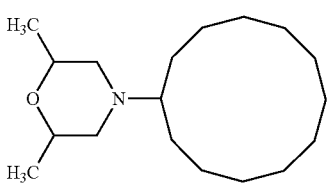 [SMILES: CC1CN(C2CCCCCCCCCCC2)CC(C)O1]

(15-4) fenpropimorph (known from DE-A 26 56 747) of the formula

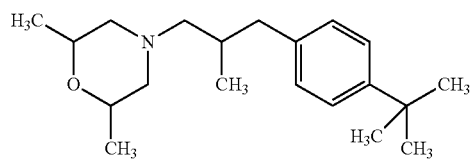 [SMILES: CC(Cc1ccc(C(C)(C)C)cc1)CN1CC(C)OC(C)C1]

(15-5) dimethomorph (known from EP-A 0 219 756) of the formula

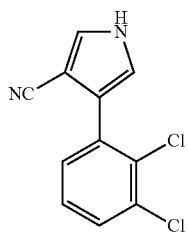 [SMILES: N#Cc1c[nH]cc1-c1cccc(Cl)c1Cl]

The formula (XI) embraces the following preferred mixing partners of group (16):
(16-1) fenpiclonil (known from EP-A 0 236 272) of the formula

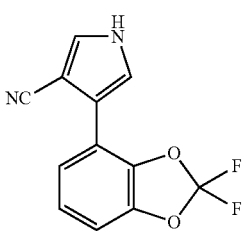 [SMILES: N#Cc1c[nH]cc1-c1cccc2c1OC(F)(F)O2]

(16-2) fludioxonil (known from EP-A 0 206 999) of the formula

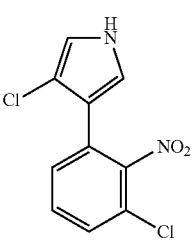 [SMILES: O=[N+]([O-])c1c(Cl)cccc1-c1c[nH]cc1Cl]

(16-3) pyrrolnitrin (known from JP 65-25876) of the formula

Preferred mixing partners of group (17) are
(17-1) fosetyl-Al (known from DE-A 24 56 627) of the formula

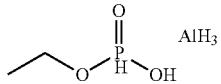

(17-2) phosphonic acid (known chemical) of the formula

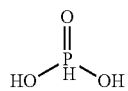

The formula (XII) embraces the following preferred mixing partners of group (18) which are known from WO 96/23793 and can in each case be present as E or Z isomers. Accordingly, compounds of the formula (XII) can be present as a mixture of different isomers or else in the form of a single isomer. Preference is given to compounds of the formula (XII) in the form of their E isomers:

(18-1)   2-(2,3-dihydro-1H-inden-5-yl)-N-[2-(3,4-dimethoxyphenyl)ethyl]-2-(methoxy-imino)acetamide of the formula

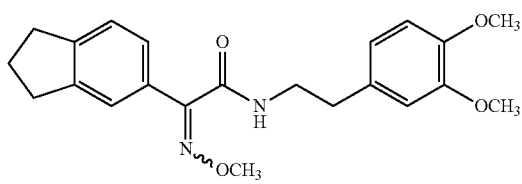 [SMILES: CON=C(C(=O)NCCc1ccc(OC)c(OC)c1)c1ccc2c(c1)CCC2]

(18-2)   N-[2-(3,4-dimethoxyphenyl)ethyl]-2-(methoxyimino)-2-(5,6,7,8-tetrahydronaphthalen-2-yl)acetamide of the formula

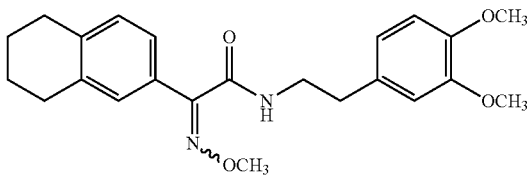 [SMILES: CON=C(C(=O)NCCc1ccc(OC)c(OC)c1)c1ccc2c(c1)CCCC2]

(18-3)   2-(4-chlorophenyl)-N-[2-(3,4-dimethoxyphenyl)ethyl]-2-(methoxyimino)acetamide of the formula

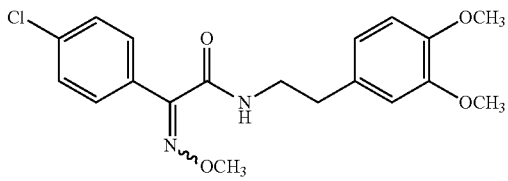 [SMILES: CON=C(C(=O)NCCc1ccc(OC)c(OC)c1)c1ccc(Cl)cc1]

(18-4)   2-(4-bromophenyl)-N-[2-(3,4-dimethoxyphenyl)ethyl]-2-(methoxyimino)acetamide of the formula

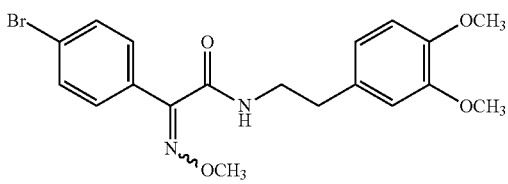 [SMILES: CON=C(C(=O)NCCc1ccc(OC)c(OC)c1)c1ccc(Br)cc1]

(18-5)   2-(4-methylphenyl)-N-[2-(3,4-dimethoxyphenyl)ethyl]-2-(methoxyimino)acetamide of the formula

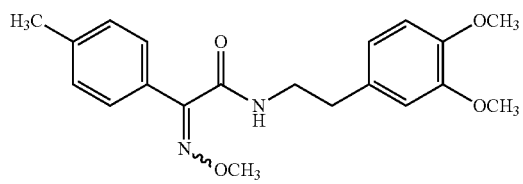 [SMILES: CON=C(C(=O)NCCc1ccc(OC)c(OC)c1)c1ccc(C)cc1]

(18-6)   2-(4-ethylphenyl)-N-[2-(3,4-dimethoxyphenyl)ethyl]-2-(methoxyimino)acetamide of the formula

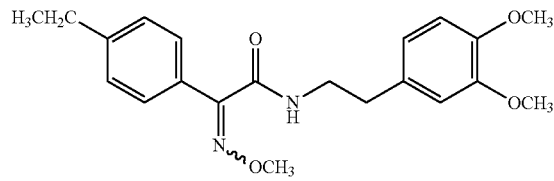

Preferred mixing partners of group (19) are
(19-1) acibenzolar-S-methyl (known from EP-A 0 313 512) of the formula

(19-2) chlorothalonil (known from U.S. Pat. No. 3,290,353) of the formula

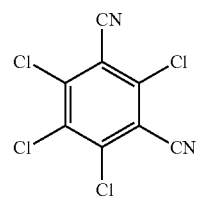 [SMILES: N#Cc1c(Cl)c(Cl)c(Cl)c(C#N)c1Cl]

(19-3) cymoxanil (known from DE-A 23 12 956) of the formula

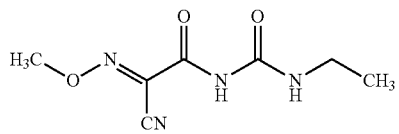

(19-4) edifenphos (known from DE-A 14 93 736) of the formula

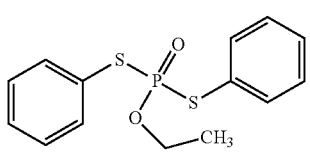 [SMILES: CCOP(=O)(Sc1ccccc1)Sc1ccccc1]

(19-5) famoxadone (known from EP-A 0 393 911) of the formula

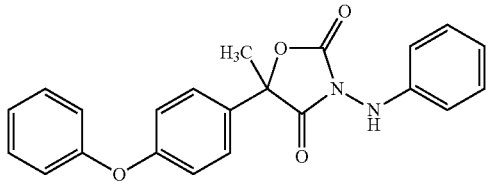 [SMILES: CC1(c2ccc(Oc3ccccc3)cc2)OC(=O)N(Nc2ccccc2)C1=O]

(19-6) fluazinam (known from EP-A 0 031 257) of the formula

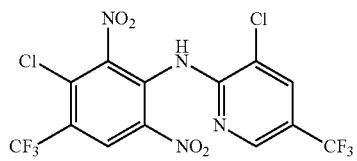 [SMILES: O=[N+]([O-])c1cc(C(F)(F)F)c(Cl)c([N+](=O)[O-])c1Nc1ncc(C(F)(F)F)cc1Cl]

(19-7) copper oxychloride (19-9) oxadixyl (known from DE-A 30 30 026) of the formula

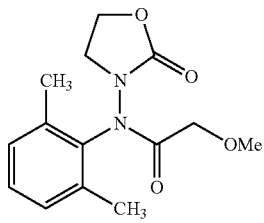 [SMILES: COCC(=O)N(c1c(C)cccc1C)N1CCOC1=O]

(19-10) spiroxamine (known from DE-A 37 35 555) of the formula

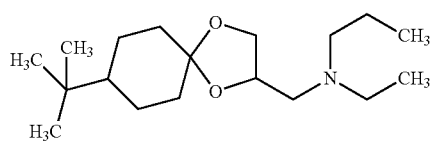 [SMILES: CCCN(CC)CC1COC2(CCC(C(C)(C)C)CC2)O1]

(19-11) dithianon (known from JP-A 44-29464) of the formula

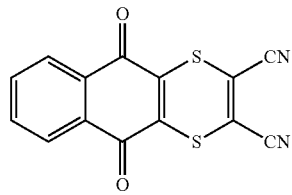 [SMILES: N#Cc1sc2c(=O)c3ccccc3c(=O)c=2sc1C#N]

(19-12) metrafenone (known from EP-A 0 897 904) of the formula

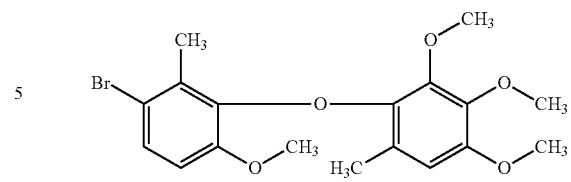

(19-13) fenamidone (known from EP-A 0 629 616) of the formula

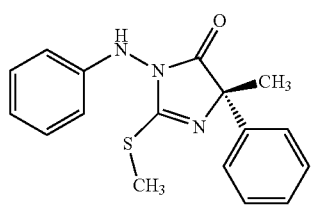 [SMILES: CSC1=N[C@@](C)(c2ccccc2)C(=O)N1Nc1ccccc1]

(19-14) 2,3-dibutyl-6-chlorothieno[2,3-d]pyrimidin-4(3H) one (known from WO 99/14202) of the formula

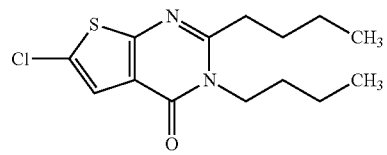 [SMILES: CCCCc1nc2sc(Cl)cc2c(=O)n1CCCC]

(19-15) probenazole (known from U.S. Pat. No. 3,629,428) of the formula

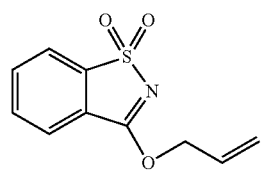

(19-16) isoprothiolane (known from U.S. Pat. No. 3,856,814) of the formula

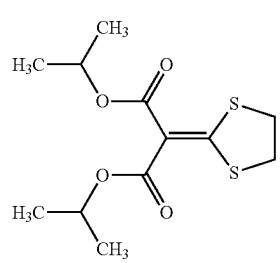 [SMILES: CC(C)OC(=O)C(C(=O)OC(C)C)=C1SCCS1]

(19-17) kasugamycin (known from GB 1 094 567) of the formula

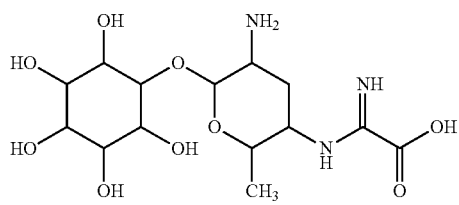 [SMILES: CC1OC(OC2C(O)C(O)C(O)C(O)C2O)C(N)CC1NC(=N)C(=O)O]

(19-18) phthalide (known from JP-A 57-55844) of the formula

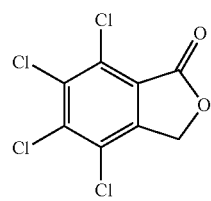 [SMILES: O=C1OCc2c(Cl)c(Cl)c(Cl)c(Cl)c21]

(19-19) ferimzone (known from EP-A 0 019 450) of the formula

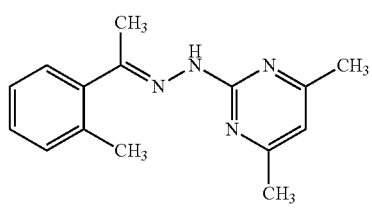 [SMILES: C/C(=N\Nc1nc(C)cc(C)n1)c1ccccc1C]

(19-20) tricyclazole (known from DE-A 22 50 077) of the formula

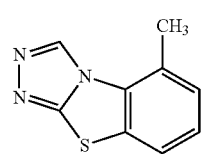

(19-21) N-({4-[(cyclopropylamino)carbonyl]phenyl}sulphonyl)-2-methoxybenzamide of the formula

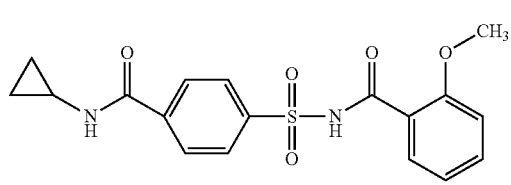 [SMILES: COc1ccccc1C(=O)NS(=O)(=O)c1ccc(C(=O)NC2CC2)cc1]

(19-22) 2-(4-chlorophenyl)-N-{2-[3-methoxy-4-(prop-2-yn-1-yloxy)phenyl]ethyl}-2-(prop-2-yn-1-yloxy)acetamide (known from WO 01/87822) of the formula

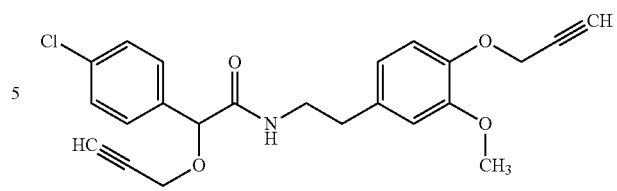

Preferred mixing partners of group (20) are (20-1) pencycuron (known from DE-A 27 32 257) of the formula

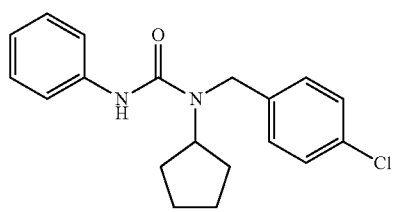 [SMILES: O=C(Nc1ccccc1)N(Cc1ccc(Cl)cc1)C1CCCC1]

(20-2) thiophanate-methyl (known from DE-A 18 06 123) of the formula

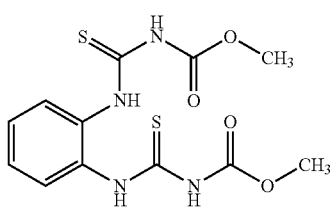 [SMILES: COC(=O)NC(=S)Nc1ccccc1NC(=S)NC(=O)OC]

(20-3) thiophanate-ethyl (known from DE-A 18 06 123) of the formula

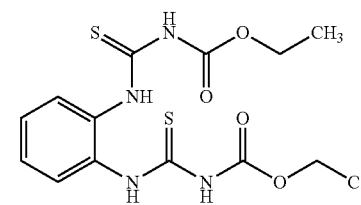

Preferred mixing partners of group (21) are (21-1) fenoxanil (known from EP-A 0 262 393) of the formula

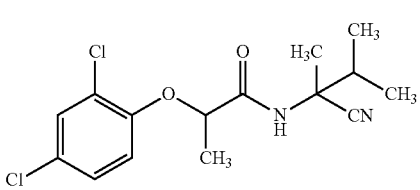 [SMILES: CC(Oc1ccc(Cl)cc1Cl)C(=O)NC(C)(C#N)C(C)C]

(21-2) diclocymet (known from JP-A 7-206608) of the formula

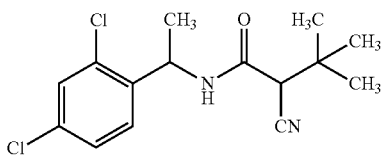 [SMILES: CC(NC(=O)C(C#N)C(C)(C)C)c1ccc(Cl)cc1Cl]

Preferred mixing partners of group (22) are (22-1) 5-chloro-N-[(1S)-2,2,2-trifluoro-1-methylethyl]-6-(2,4,6-trifluorophenyl)[1,2,4]triazolo-[1,5-a]pyrimidine-7-amine (known from U.S. Pat. No. 5,986,135) of the formula

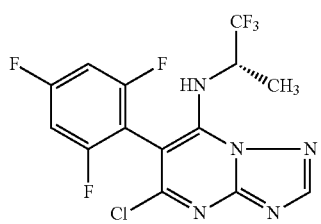 [SMILES: C[C@H](Nc1c(-c2c(F)cc(F)cc2F)c(Cl)nc2ncnn12)C(F)(F)F]

(22-2) 5-chloro-N-[(1R)-1,2-dimethylpropyl]-6-(2,4,6-trifluorophenyl)[1,2,4]triazolo[1,5-a]-pyrimidine-7-amine (known from WO 02/38565) of the formula

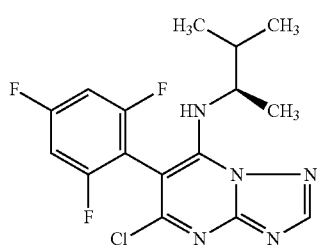 [SMILES: CC(C)[C@@H](C)Nc1c(-c2c(F)cc(F)cc2F)c(Cl)nc2ncnn12]

(22-3) 5-chloro-6-(2-chloro-6-fluorophenyl)-7-(4-methylpiperidin-1-yl)[1,2,4]triazolo[1,5-a]-pyrimidine (known from U.S. Pat. No. 5,593,996) of the formula

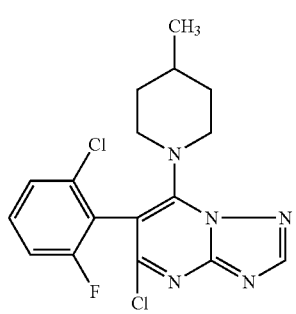 [SMILES: CC1CCN(c2c(-c3c(F)cccc3Cl)c(Cl)nc3ncnn23)CC1]

(22-4) 5-chloro-6-(2,4,6-trifluorophenyl)-7-(4-methylpiperidin-1-yl)[1,2,4]triazolo[1,5-a]pyrimidine (known from DE-A 101 24 208) of the formula

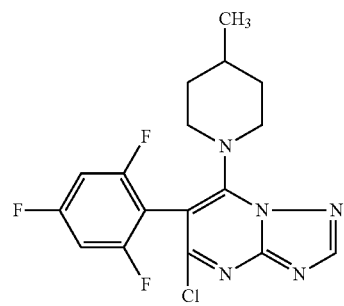 [SMILES: CC1CCN(c2c(-c3c(F)cc(F)cc3F)c(Cl)nc3ncnn23)CC1]

Preferred mixing partners of group (23) are (23-1) 2-butoxy-6-iodo-3-propylbenzopyran-4-one (known from WO 03/014103) of the formula

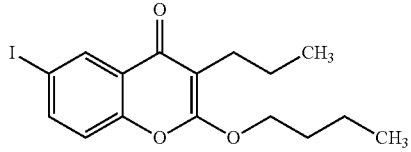 [SMILES: CCCCOc1oc2ccc(I)cc2c(=O)c1CCC]

(23-2) 2-ethoxy-6-iodo-3-propylbenzopyran-4-one (known from WO 03/014103) of the formula

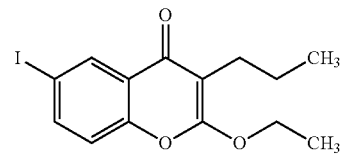 [SMILES: CCCc1c(OCC)oc2ccc(I)cc2c1=O]

(23-3) 6-iodo-2-propoxy-3-propylbenzopyran-4-one (known from WO 03/014103) of the formula

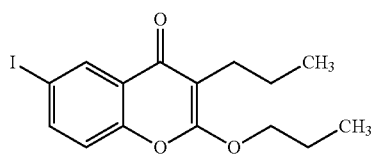 [SMILES: CCCOc1oc2ccc(I)cc2c(=O)c1CCC]

(23-4) 2-but-2-ynyloxy-6-iodo-3-propylbenzopyran-4-one (known from WO 03/014103) of the formula

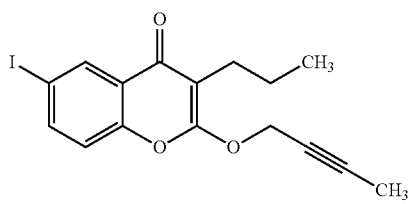 [SMILES: CC#CCOc1oc2ccc(I)cc2c(=O)c1CCC]

(23-5) 6-iodo-2-(1-methylbutoxy)-3-propylbenzopyran-4-one (known from WO 03/014103) of the formula

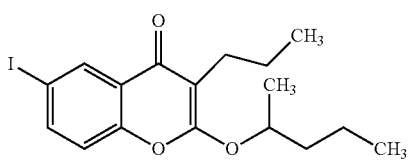 [SMILES: CCCc1c(OC(C)CCC)oc2ccc(I)cc2c1=O]

(23-6) 2-but-3-enyloxy-6-iodobenzopyran-4-one (known from WO 03/014103) of the formula

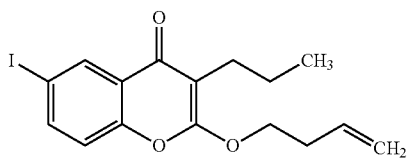 [SMILES: C=CCCOc1oc2ccc(I)cc2c(=O)c1CCC]

(23-7) 3-butyl-6-iodo-2-isopropoxybenzopyran-4-one (known from WO 03/014103) of the formula

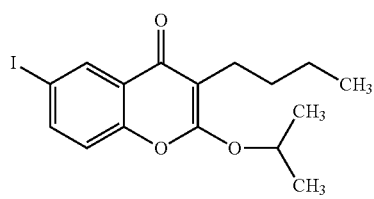 [SMILES: CCCCc1c(OC(C)C)oc2ccc(I)cc2c1=O]

Compound (6-7), carpropamid, has three asymmetrically substituted carbon atoms. Accordingly, compound (6-7) can be present as a mixture of different isomers or else in the form of a single component. Particular preference is given to the compounds
(1S,3R)-2,2-dichloro-N-[(1R)-1-(4-chlorophenyl)ethyl]-1-ethyl-3-methylcyclopropanecarboxamide of the formula

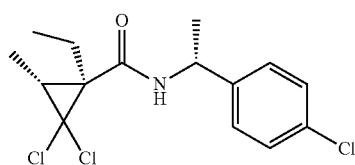 [SMILES: CC[C@@]1(C(=O)N[C@H](C)c2ccc(Cl)cc2)[C@@H](C)C1(Cl)Cl]

(1R,3S)-2,2-dichloro-N-[(1R)-1-(4-chlorophenyl)ethyl]-1-ethyl-3-methylcyclopropanecarboxamide of the formula

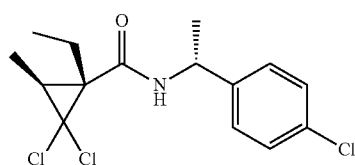 [SMILES: CC[C@]1(C(=O)N[C@H](C)c2ccc(Cl)cc2)[C@H](C)C1(Cl)Cl]

Particularly preferred mixing partners are the following active compounds:
(2-1) azoxystrobin
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(2-5) (2E)-2-(methoxyimino)-N-methyl-2-(2-{[({(1E)-1-[3-(trifluoromethyl)-phenyl]ethylidene}amino)oxy]methyl}phenyl)ethanamide
(2-6) (2E)-2-(methoxyimino)-N-methyl-2-{2-[(E)-({1-[3-(trifluoromethyl)phenyl]-ethoxy}imino)methyl]phenyl}ethanamide
(2-8) 5-methoxy-2-methyl-4-(2-{[({(1E)-1-[3-(trifluoromethyl)phenyl]ethylidene}-amino)oxy]methyl}phenyl)-2,4-dihydro-3H-1,2,4-triazol-3-one
(2-11) picoxystrobin
(2-9) kresoxim-methyl
(2-10) dimoxystrobin
(2-12) pyraclostrobin
(2-13) metominostrobin
(3-3) propiconazole
(3-4) difenoconazole
(3-6) cyproconazole
(3-7) hexaconazole
(3-8) penconazole
(3-9) myclobutanil
(3-10) tetraconazole
(3-13) flusilazole
(3-15) prothioconazole
(3-16) fenbuconazole
(3-17) tebuconazole
(3-21) bitertanol
(3-22) triadimenol
(3-23) triadimefon
(3-12) epoxiconazole
(3-19) metconazole
(3-24) fluquinconazole
(4-1) dichlofluanid
(4-2) tolylfluanid
(5-1) iprovalicarb
(5-3) benthiavalicarb
(6-2) boscalid
(6-5) ethaboxam
(6-6) fenhexamid
(6-7) carpropamid
(6-8) 2-chloro-4-[(2-fluoro-2-methylpropanoyl)amino]-N,N-dimethylbenzamide
(6-9) picobenzamid
(6-10) zoxamide
(6-11) 3,4-dichloro-N-(2-cyanophenyl)isothiazole-5-carboxamide
(6-14) penthiopyrad
(6-16) N-[2-(1,3-dimethylbutyl)phenyl]-1-methyl-4-(trifluoromethyl)-1H-pyrrole-3-carboxamide
(7-1) mancozeb
(7-2) maneb
(7-4) propineb
(7-5) thiram
(7-6) zineb
(8-1) benalaxyl
(8-2) furalaxyl
(8-3) metalaxyl
(8-4) metalaxyl-M
(8-5) benalaxyl-M
(9-1) cyprodinil
(9-2) mepanipyrim
(9-3) pyrimethanil
(10-1) 6-chloro-5-[(3,5-dimethylisoxazol-4-yl)sulphonyl]-2,2-difluoro-5H-[1,3]dioxolo[4,5-f]-benzimidazole
(10-3) carbendazim
(11-1) diethofencarb
(11-2) propamocarb (11-3) propamocarb-hydrochloride
(11-4) propamocarb-fosetyl
(12-2) captan
(12-3) folpet
(12-4) iprodione
(12-5) procymidone
(13-1) dodine
(13-2) guazatine
(13-3) iminoctadine triacetate
(14-1) cyazofamid
(14-2) prochloraz
(14-3) triazoxide
(15-5) dimethomorph
(15-4) fenpropimorph
(16-2) fludioxonil
(17-1) fosetyl-Al
(17-2) phosphonic acid
(19-1) acibenzolar-S-methyl
(19-2) chlorothalonil
(19-3) cymoxanil
(19-5) famoxadone
(19-7) copper oxychloride
(19-6) fluazinam
(19-9) oxadixyl
(19-10) spiroxamine
(19-13) fenamidone
(19-22) 2-(4-chlorophenyl)-N-{2-[3-methoxy-4-(prop-2-yn-1-yloxy)phenyl]ethyl}-2-(prop-2-yn-1-yloxy)acetamide
(20-1) pencycuron
(20-2) thiophanate-methyl
(22-1) 5-chloro-N-[(1S)-2,2,2-trifluoro-1-methylethyl]-6-(2,4,6-trifluorophenyl)[1,2,4]-triazolo[1,5-a]pyrimidine-7-amine
(22-2) 5-chloro-N-[(1R)-1,2-dimethylpropyl]-6-(2,4,6-trifluorophenyl)[1,2,4]triazolo[1,5-a]-pyrimidine-7-amine
(22-4) 5-chloro-6-(2,4,6-trifluorophenyl)-7-(4-methylpiperidin-1-yl)[1,2,4]triazolo[1,5-a]pyrimidine
(23-1) 2-butoxy-6-iodo-3-propylbenzopyran-4-one
(23-2) 2-ethoxy-6-iodo-3-propylbenzopyran-4-one
(23-3) 6-iodo-2-propoxy-3-propylbenzopyran-4-one Very particularly preferred mixing partners are the following active compounds:
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(3-15) prothioconazole
(3-17) tebuconazole
(3-21) bitertanol
(3-22) triadimenol
(3-24) fluquinconazole
(4-1) dichlofluanid
(4-2) tolylfluanid
(5-1) iprovalicarb
(6-6) fenhexamid
(6-7) carpropamid
(6-9) picobenzamid
(6-14) penthiopyrad
(7-4) propineb
(8-4) metalaxyl-M
(8-5) benalaxyl-M
(9-3) pyrimethanil
(10-3) carbendazim
(11-4) propamocarb-fosetyl
(12-4) iprodione
(14-2) prochloraz
(14-3) triazoxide
(16-2) fludioxonil
(19-10) spiroxamine
(19-22) 2-(4-chlorophenyl)-N-{2-[3-methoxy-4-(prop-2-yn-1-yloxy)phenyl]ethyl}-2-(prop-2-yn-1-yloxy)acetamide
(22-4) 5-chloro-6-(2,4,6-trifluorophenyl)-7-(4-methylpiperidin-1-yl)[1,2,4]triazolo[1,5-a]pyrimidine Preferred active compound combinations consisting of two groups of active compounds and comprising in each case at least one carboxamide of the formula (I) (group 1) and at least one active compound from the stated group (2) to (23) are described below. These combinations are the active compound combinations A to T.

Among the preferred active compound combinations A to T, emphasis is given to those comprising a carboxamide of the formula (I) (group 1)

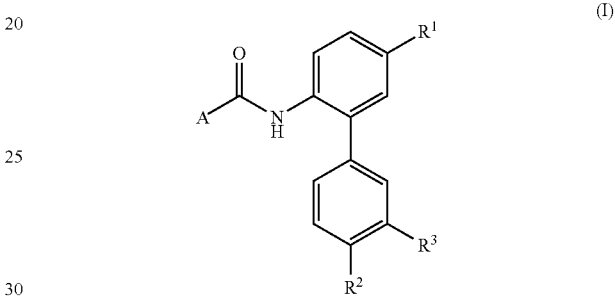

in which $R^1$, $R^2$, $R^3$ and A are as defined above.

Particular preference is given to active compound combinations A to T comprising a carboxamide of the formula (I) (group 1)

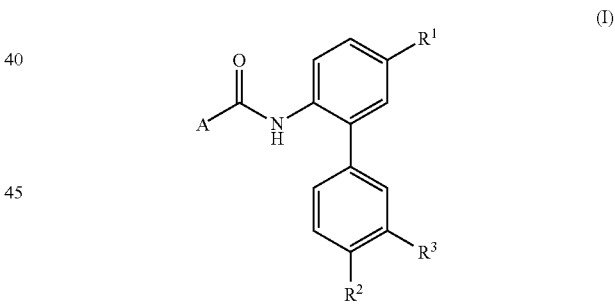

in which
$R^1$ represents hydrogen or fluorine,
$R^2$ represents fluorine, chlorine, bromine, trifluoromethyl or represents —CH=N—OCH$_3$,
$R^3$ represents hydrogen, fluorine or chlorine,
A represents one of the radicals A1 or A2 below:

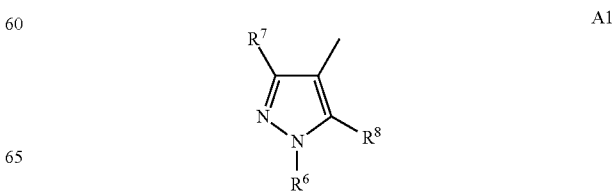

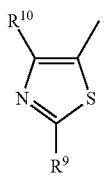

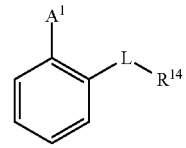

in which $A^1$, L and $R^{14}$ are as defined above.

$R^6$ represents methyl,
$R^7$ represents methyl, difluoromethyl or trifluoromethyl,
$R^8$ represents hydrogen or fluorine,
$R^9$ represents methyl,
$R^{10}$ represents methyl, difluoromethyl or trifluoromethyl.

Very particular preference is given to active compound combinations A to T in which the carboxamide of the formula (I) (group 1) is selected from the list below:
(1-1) N-(3',4'-dichloro-5-fluoro-1,1'-biphenyl-2-yl)-3-(difluoromethyl)-1-methyl-1H-pyrazole-4-carboxamide
(1-2) 3-(difluoromethyl)-N-{3'-fluoro-4'-[(E)-(methoxyimino)methyl]-1,1'-biphenyl-2-yl}-1-methyl-1H-pyrazole-4-carboxamide
(1-3) 3-(trifluoromethyl)-N-{3'-fluoro-4'-[(E)-(methoxyimino)methyl]-1,1'-biphenyl-2-yl}-1-methyl-1H-pyrazole-4-carboxamide
(1-4) N-(3',4'-dichloro-1,1'-biphenyl-2-yl)-5-fluoro-1,3-dimethyl-1H-pyrazole-4-carboxamide
(1-5) N-(4'-chloro-3'-fluoro-1,1'-biphenyl-2-yl)-2-methyl-4-(trifluoromethyl)-1,3-thiazole-5-carboxamide
(1-6) N-(4'-chloro-1,1'-biphenyl-2-yl)-4-(difluoromethyl)-2-methyl-1,3-thiazole-5-carboxamide
(1-7) N-(4'-bromo-1,1'-biphenyl-2-yl)-4-(difluoromethyl)-2-methyl-1,3-thiazole-5-carboxamide
(1-8) 4-(difluoromethyl)-2-methyl-N-[4'-(trifluoromethyl)-1,1'-biphenyl-2-yl]-1,3-thiazole-5-carboxamide
(1-9) N-(4'-chloro-3'-fluoro-1,1'-biphenyl-2-yl)-4-(difluoromethyl)-2-methyl-1,3-thiazole-5-carboxamide Especially preferred are active compound combinations A to T in which the carboxamide of the formula (I) (group 1) is selected from the list below:
(1-1) N-(3',4'-dichloro-5-fluoro-1,1'-biphenyl-2-yl)-3-(difluoromethyl)-1-methyl-1H-pyrazole-4-carboxamide
(1-7) N-(4'-bromo-1,1'-biphenyl-2-yl)-4-(difluoromethyl)-2-methyl-1,3-thiazole-5-carboxamide
(1-8) 4-(difluoromethyl)-2-methyl-N-[4'-(trifluoromethyl)-1,1'-biphenyl-2-yl]-1,3-thiazole-5-carboxamide
(1-9) N-(4'-chloro-3'-fluoro-1,1'-biphenyl-2-yl)-4-(difluoromethyl)-2-methyl-1,3-thiazole-5-carboxamide.

In addition to a carboxamide of the formula (I) (group 1), the active compound combinations A also comprise a strobilurin of the formula (II) (group 2)

Particular preference is given to active compound combinations A in which the strobilurin of the formula (II) (group 2) is selected from the list below:
(2-1) azoxystrobin
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(2-5) (2E)-2-(methoxyimino)-N-methyl-2-(2-{[({(1E)-1-[3-(trifluoromethyl)phenyl]ethylidene}-amino)oxy]methyl}phenyl)ethanamide
(2-6) (2E)-2-(methoxyimino)-N-methyl-2-{2-[(E)-({1-[3-(trifluoromethyl)phenyl]ethoxy}imino)-methyl]phenyl}ethanamide
(2-7) orysastrobin
(2-8) 5-methoxy-2-methyl-4-(2-{[({(1E)-1-[3-(trifluoromethyl)phenyl]ethylidene}amino)oxy]-methyl}phenyl)-2,4-dihydro-3H-1,2,4-triazol-3-one
(2-9) kresoxim-methyl
(2-10) dimoxystrobin
(2-11) picoxystrobin
(2-12) pyraclostrobin
(2-13) metominostrobin Very particular preference is given to active compound combinations A in which the strobilurin of the formula (II) (group 2) is selected from the list below:
(2-1) azoxystrobin
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(2-12) pyraclostrobin
(2-9) kresoxim-methyl
(2-10) dimoxystrobin
(2-11) picoxystrobin
(2-13) metominostrobin Emphasis is given to the active compound combinations A listed in Table 1 below:

TABLE 1

| | Active compound combinations A | |
|---|---|---|
| No. | Carboxamide of the formula (I) | Strobilurin of the formula (II) |
| A-1 | (1-1) N-(3',4'-dichloro-5-fluoro-1,1'-biphenyl-2-yl)-3-(difluoromethyl)-1-methyl-1H-pyrazole-4-carboxamide | (2-1) azoxystrobin |
| A-2 | (1-1) N-(3',4'-dichloro-5-fluoro-1,1'-biphenyl-2-yl)-3-(difluoromethyl)-1-methyl-1H-pyrazole-4-carboxamide | (2-2) fluoxastrobin |
| A-3 | (1-1) N-(3',4'-dichloro-5-fluoro-1,1'-biphenyl-2-yl)-3-(difluoromethyl)-1-methyl-1H-pyrazole-4-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-4 | (1-1) N-(3',4'-dichloro-5-fluoro-1,1'-biphenyl-2-yl)-3-(difluoromethyl)-1-methyl-1H-pyrazole-4-carboxamide | (2-4) trifloxystrobin |

TABLE 1-continued

Active compound combinations A

| No. | Carboxamide of the formula (I) | Strobilurin of the formula (II) |
|---|---|---|
| A-5 | (1-1) N-(3',4'-dichloro-5-fluoro-1,1'-biphenyl-2-yl)-3-(difluoromethyl)-1-methyl-1H-pyrazole-4-carboxamide | (2-12) pyraclostrobin |
| A-6 | (1-2) 3-(difluoromethyl)-N-{3'-fluoro-4'-[(E)-(methoxyimino)methyl]-1,1'-biphenyl-2-yl}-1-methyl-1H-pyrazole-4-carboxamide | (2-1) azoxystrobin |
| A-7 | (1-2) 3-(difluoromethyl)-N-{3'-fluoro-4'-[(E)-(methoxyimino)methyl]-1,1'-biphenyl-2-yl}-1-methyl-1H-pyrazole-4-carboxamide | (2-2) fluoxastrobin |
| A-8 | (1-2) 3-(difluoromethyl)-N-{3'-fluoro-4'-[(E)-(methoxyimino)methyl]-1,1'-biphenyl-2-yl}-1-methyl-1H-pyrazole-4-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-9 | (1-2) 3-(difluoromethyl)-N-{3'-fluoro-4'-[(E)-(methoxyimino)methyl]-1,1'-biphenyl-2-yl}-1-methyl-1H-pyrazole-4-carboxamide | (2-4) trifloxystrobin |
| A-10 | (1-2) 3-(difluoromethyl)-N-{3'-fluoro-4'-[(E)-(methoxyimino)methyl]-1,1'-biphenyl-2-yl}-1-methyl-1H-pyrazole-4-carboxamide | (2-12) pyraclostrobin |
| A-11 | (1-3) 3-(trifluoromethyl)-N-{3'-fluoro-4'-[(E)-(methoxyimino)methyl]-1,1'-biphenyl-2-yl}-1-methyl-1H-pyrazole-4-carboxamide | (2-1) azoxystrobin |
| A-12 | (1-3) 3-(trifluoromethyl)-N-{3'-fluoro-4'-[(E)-(methoxyimino)methyl]-1,1'-biphenyl-2-yl}-1-methyl-1H-pyrazole-4-carboxamide | (2-2) fluoxastrobin |
| A-13 | (1-3) 3-(trifluoromethyl)-N-{3'-fluoro-4'-[(E)-(methoxyimino)methyl]-1,1'-biphenyl-2-yl}-methyl-1H-pyrazole-4-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-14 | (1-3) 3-(trifluoromethyl)-N-{3'-fluoro-4'-[(E)-(methoxyimino)methyl]-1,1'-biphenyl-2-yl}-methyl-1H-pyrazole-4-carboxamide | (2-4) trifloxystrobin |
| A-15 | (1-3) 3-(trifluoromethyl)-N-{3'-fluoro-4'-[(E)-(methoxyimino)methyl]-1,1'-biphenyl-2-yl}-methyl-1H-pyrazole-4-carboxamide | (2-12) pyraclostrobin |
| A-16 | (1-4) N-(3',4'-dichloro-1,1'-biphenyl-2-yl)-5-fluoro-1,3-dimethyl-1H-pyrazole-4-carboxamide | (2-1) azoxystrobin |
| A-17 | (1-4) N-(3',4'-dichloro-1,1'-biphenyl-2-yl)-5-fluoro-1,3-dimethyl-1H-pyrazole-4-carboxamide | (2-2) fluoxastrobin |
| A-18 | (1-4) N-(3',4'-dichloro-1,1'-biphenyl-2-yl)-5-fluoro-1,3-dimethyl-1H-pyrazole-4-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-19 | (1-4) N-(3',4'-dichloro-1,1'-biphenyl-2-yl)-5-fluoro-1,3-dimethyl-1H-pyrazole-4-carboxamide | (2-4) trifloxystrobin |
| A-20 | (1-4) N-(3',4'-dichloro-1,1'-biphenyl-2-yl)-5-fluoro-1,3-dimethyl-1H-pyrazole-4-carboxamide | (2-12) pyraclostrobin |
| A-21 | (1-5) N-(4'-chloro-3'-fluoro-1,1'-biphenyl-2-yl)-2-methyl-4-(trifluoromethyl)-1,3-thiazole-5-carboxamide | (2-1) azoxystrobin |
| A-22 | (1-5) N-(4'-chloro-3'-fluoro-1,1'-biphenyl-2-yl)-2-methyl-4-(trifluoromethyl)-1,3-thiazole-5-carboxamide | (2-2) fluoxastrobin |
| A-23 | (1-5) N-(4'-chloro-3'-fluoro-1,1'-biphenyl-2-yl)-2-methyl-4-(trifluoromethyl)-1,3-thiazole-5-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-24 | (1-5) N-(4'-chloro-3'-fluoro-1,1'-biphenyl-2-yl)-2-methyl-4-(trifluoromethyl)-1,3-thiazole-5-carboxamide | (2-4) trifloxystrobin |
| A-25 | (1-5) N-(4'-chloro-3'-fluoro-1,1'-biphenyl-2-yl)-2-methyl-4-(trifluoromethyl)-1,3-thiazole-5-carboxamide | (2-12) pyraclostrobin |
| A-26 | (1-6) N-(4'-chloro-1,1'-biphenyl-2-yl)-4-(difluoromethyl)-2-methyl-1,3-thiazole-5-carboxamide | (2-1) azoxystrobin |
| A-27 | (1-6) N-(4'-chloro-1,1'-biphenyl-2-yl)-4-(difluoromethyl)-2-methyl-1,3-thiazole-5-carboxamide | (2-2) fluoxastrobin |
| A-28 | (1-6) N-(4'-chloro-1,1'-biphenyl-2-yl)-4-(difluoro-methyl)-2-methyl-1,3-thiazole-5-carboxamide | (2-3) (2E)-2-(2-{[6-(3-chloro-2-methylphenoxy)-5-fluoro-4-pyrimidinyl]oxy}phenyl)-2-o(methxyimino)-N-methylethanamide |
| A-29 | (1-6) N-(4'-chloro-1,1'-biphenyl-2-yl)-4-(difluoromethyl)-2-methyl-1,3-thiazole-5-carboxamide | (2-4) trifloxystrobin |
| A-30 | (1-6) N-(4'-chloro-1,1'-biphenyl-2-yl)-4-(difluoromethyl)-2-methyl-1,3-thiazole-5-carboxamide | (2-12) pyraclostrobin |
| A-31 | (1-7) N-(4'-bromo-1,1'-biphenyl-2-yl)-4-(difluoromethyl)-2-methyl-1,3-thiazole-5-carboxamide | (2-1) azoxystrobin |
| A-32 | (1-7) N-(4'-bromo-1,1'-biphenyl-2-yl)-4-(difluoromethyl)-2-methyl-1,3-thiazole-5-carboxamide | (2-2) fluoxastrobin |

TABLE 1-continued

Active compound combinations A

| No. | Carboxamide of the formula (I) | Strobilurin of the formula (II) |
| --- | --- | --- |
| A-33 | (1-7) N-(4'-bromo-1,1'-biphenyl-2-yl)-4-(difluoromethyl)-2-methyl-1,3-thiazole-5-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-34 | (1-7) N-(4'-bromo-1,1'-biphenyl-2-yl)-4-(difluoromethyl)-2-methyl-1,3-thiazole-5-carboxamide | (2-4) trifloxystrobin |
| A-35 | (1-7) N-(4'-bromo-1,1'-biphenyl-2-yl)-4-(difluoromethyl)-2-methyl-1,3-thiazole-5-carboxamide | (2-12) pyraclostrobin |
| A-36 | (1-8) 4-(difluoromethyl)-2-methyl-N-[4'-(trifluoromethyl)-1,1'-biphenyl-2-yl]-1,3-thiazole-5-carboxamide | (2-1) azoxystrobin |
| A-37 | (1-8) 4-(difluoromethyl)-2-methyl-N-[4'-(trifluoromethyl)-1,1'-biphenyl-2-yl]-1,3-thiazole-5-carboxamide | (2-2) fluoxastrobin |
| A-38 | (1-8) 4-(difluoromethyl)-2-methyl-N-[4'-(trifluoromethyl)-1,1'-biphenyl-2-yl]-1,3-thiazole-5-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-39 | (1-8) 4-(difluoromethyl)-2-methyl-N-[4'-(trifluoromethyl)-1,1'-biphenyl-2-yl]-1,3-thiazole-5-carboxamide | (2-4) trifloxystrobin |
| A-40 | (1-8) 4-(difluoromethyl)-2-methyl-N-[4'-(trifluoromethyl)-1,1'-biphenyl-2-yl]-1,3-thiazole-5-carboxamide | (2-12) pyraclostrobin |
| A-41 | (1-1) N-(3',4'-dichloro-5-fluoro-1,1'-biphenyl-2-yl)-3-(difluoromethyl)-1-methyl-1H-pyrazole-4-carboxamide | (2-9) kresoxim-methyl |
| A-42 | (1-1) N-(3',4'-dichloro-5-fluoro-1,1'-biphenyl-2-yl)-3-(difluoromethyl)-1-methyl-1H-pyrazole-4-carboxamide | (2-10) dimoxystrobin |
| A-43 | (1-1) N-(3',4'-dichloro-5-fluoro-1,1'-biphenyl-2-yl)-3-(difluoromethyl)-1-methyl-1H-pyrazole-4-carboxamide | (2-11) picoxystrobin |
| A-44 | (1-1) N-(3',4'-dichloro-5-fluoro-1,1'-biphenyl-2-yl)-3-(difluoromethyl)-1-methyl-1H-pyrazole-4-carboxamide | (2-13) metominostrobin |
| A-45 | (1-7) N-(4'-bromo-1,1'-biphenyl-2-yl)-4-(difluoromethyl)-2-methyl-1,3-thiazole-5-carboxamide | (2-9) kresoxim-methyl |
| A-46 | (1-7) N-(4'-bromo-1,1'-biphenyl-2-yl)-4-(difluoromethyl)-2-methyl-1,3-thiazole-5-carboxamide | (2-10) dimoxystrobin |
| A-47 | (1-7) N-(4'-bromo-1,1'-biphenyl-2-yl)-4-(difluoromethyl)-2-methyl-1,3-thiazole-5-carboxamide | (2-11) picoxystrobin |
| A-48 | (1-7) N-(4'-bromo-1,1'-biphenyl-2-yl)-4-(difluoromethyl)-2-methyl-1,3-thiazole-5-carboxamide | (2-13) metominostrobin |
| A-49 | (1-8) 4-(difluoromethyl)-2-methyl-N-[4'-(trifluoromethyl)-1,1'-biphenyl-2-yl]-1,3-thiazole-5-carboxamide | (2-9) kresoxim-methyl |
| A-50 | (1-8) 4-(difluoromethyl)-2-methyl-N-[4'-(trifluoromethyl)-1,1'-biphenyl-2-yl]-1,3-thiazole-5-carboxamide | (2-10) dimoxystrobin |
| A-51 | (1-8) 4-(difluoromethyl)-2-methyl-N-[4'-(trifluoromethyl)-1,1'-biphenyl-2-yl]-1,3-thiazole-5-carboxamide | (2-11) picoxystrobin |
| A-52 | (1-8) 4-(difluoromethyl)-2-methyl-N-[4'-(trifluoromethyl)-1,1'-biphenyl-2-yl]-1,3-thiazole-5-carboxamide | (2-13) metominostrobin |
| A-53 | (1-9) N-(4'-chloro-3'-fluoro-1,1'-biphenyl-2-yl)-4-(difluoromethyl)-2-methyl-1,3-thiazole-5-carboxamide | (2-9) kresoxim-methyl |
| A-54 | (1-9) N-(4'-chloro-3'-fluoro-1,1'-biphenyl-2-yl)-4-(difluoromethyl)-2-methyl-1,3-thiazole-5-carboxamide | (2-10) dimoxystrobin |
| A-55 | (1-9) N-(4'-chloro-3'-fluoro-1,1'-biphenyl-2-yl)-4-(difluoromethyl)-2-methyl-1,3-thiazole-5-carboxamide | (2-11) picoxystrobin |
| A-56 | (1-9) N-(4'-chloro-3'-fluoro-1,1'-biphenyl-2-yl)-4-(difluoromethyl)-2-methyl-1,3-thiazole-5-carboxamide | (2-13) metominostrobin |
| A-57 | (1-9) N-(4'-chloro-3'-fluoro-1,1'-biphenyl-2-yl)-4-(difluoromethyl)-2-methyl-1,3-thiazole-5-carboxamide | (2-1) azoxystrobin |
| A-58 | (1-9) N-(4'-chloro-3'-fluoro-1,1'-biphenyl-2-yl)-4-(difluoromethyl)-2-methyl-1,3-thiazole-5-carboxamide | (2-2) fluoxastrobin |
| A-59 | (1-9) N-(4'-chloro-3'-fluoro-1,1'-biphenyl-2-yl)-4-(difluoromethyl)-2-methyl-1,3-thiazole-5-carboxamide | (2-3) (2E)-2-(2-{[6-(3-chloro-2-methylphenoxy)-5-fluoro-4-pyrimidinyl]oxy{phenyl)-2-(methoxyimino)-N-methylethanamide |
| A-60 | (1-9) N-(4'-chloro-3'-fluoro-1,1'-biphenyl-2-yl)-4-(difluoromethyl)-2-methyl-1,3-thiazole-5-carboxamide | (2-4) trifloxystrobin |
| A-61 | (1-9) N-(4'-chloro-3'-fluoro-1,1'-biphenyl-2-yl)-4-(difluoromethyl)-2-methyl-1,3-thiazole-5-carboxamide | (2-12) pyraclostrobin |

In addition to a carboxamide of the formula (I) (group 1), the active compound combinations B also comprise a triazole of the formula (III) (group 3)

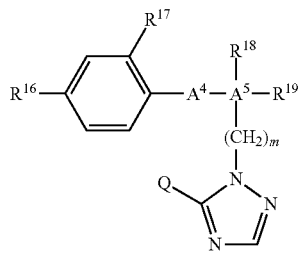

in which Q, m, $R^{16}$, $R^{17}$, $A^4$, $A^5$, $R^{18}$ and $R^{19}$ are as defined above.

Preference is given to active compound combinations B in which the triazole of the formula (III) (group 3) is selected from the list below:
(3-1) azaconazole
(3-2) etaconazole
(3-3) propiconazole
(3-4) difenoconazole
(3-5) bromuconazole
(3-6) cyproconazole
(3-7) hexaconazole
(3-8) penconazole
(3-9) myclobutanil
(3-10) tetraconazole
(3-11) flutriafol
(3-12) epoxiconazole
(3-13) flusilazole
(3-14) simeconazole
(3-15) prothioconazole
(3-16) fenbuconazole
(3-17) tebuconazole
(3-18) ipconazole
(3-19) metconazole
(3-20) triticonazole
(3-21) bitertanol
(3-22) triadimenol
(3-23) triadimefon
(3-24) fluquinconazole
(3-25) quinconazole Particular preference is given to active compound combinations B in which the triazole of the formula (III) (group 3) is selected from the list below:
(3-3) propiconazole
(3-4) difenoconazole
(3-6) cyproconazole
(3-7) hexaconazole
(3-15) prothioconazole
(3-17) tebuconazole
(3-21) bitertanol
(3-19) metconazole
(3-22) triadimenol
(3-24) fluquinconazole Emphasis is given to the active compound combinations B listed in Table 2 below:

TABLE 2

Active compound combinations B

| No. | Carboxamide of the formula (I) | Triazole of the formula (III) |
|---|---|---|
| B-1 | (1-1) N-(3',4'-dichloro-5-fluoro-1,1'-biphenyl-2-yl)-3-(difluoromethyl)-1-methyl-1H-pyrazole-4-carboxamide | (3-3) propiconazole |
| B-2 | (1-1) N-(3',4'-dichloro-5-fluoro-1,1'-biphenyl-2-yl)-3-(difluoromethyl)-1-methyl-1H-pyrazole-4-carboxamide | (3-6) cyproconazole |
| B-3 | (1-1) N-(3',4'-dichloro-5-fluoro-1,1'-biphenyl-2-yl)-3-(difluoromethyl)-1-methyl-1H-pyrazole-4-carboxamide | (3-15) prothioconazole |
| B-4 | (1-1) N-(3',4'-dichloro-5-fluoro-1,1'-biphenyl-2-yl)-3-(difluoromethyl)-1-methyl-1H-pyrazole-4-carboxamide | (3-17) tebuconazole |
| B-5 | (1-1) N-(3',4'-dichloro-5-fluoro-1,1'-biphenyl-2-yl)-3-(difluoromethyl)-1-methyl-1H-pyrazole-4-carboxamide | (3-21) bitertanol |
| B-6 | (1-2) 3-(difluoromethyl)-N-{3'-fluoro-4'-[(E)-(methoxyimino)-methyl]-1,1'-biphenyl-2-yl}-1-methyl-1H-pyrazole-4-carboxamide | (3-3) propiconazole |
| B-7 | (1-2) 3-(difluoromethyl)-N-{3'-fluoro-4'-[(E)-(methoxyimino)-methyl]-1,1'-biphenyl-2-yl}-1-methyl-1H-pyrazole-4-carboxamide | (3-6) cyproconazole |
| B-8 | (1-2) 3-(difluoromethyl)-N-{3'-fluoro-4'-[(E)-(methoxyimino)-methyl]-1,1'-biphenyl-2-yl}-1-methyl-1H-pyrazole-4-carboxamide | (3-15) prothioconazole |
| B-9 | (1-2) 3-(difluoromethyl)-N-{3'-fluoro-4'-[(E)-(methoxyimino)-methyl]-1,1'-bipheny1-2-yl}-1-methyl-1H-pyrazole-4-carboxamide | (3-17) tebuconazole |
| B-10 | (1-2) 3-(difluoromethyl)-N-{3'-fluoro-4'-[(E)-(methoxyimino)-methyl]-1,1'-biphenyl-2-yl}-1-methyl-1H-pyrazole-4-carboxamide | (3-21) bitertanol |
| B-11 | (1-3) 3-(trifluoromethyl)-N-{3'-fluoro-4'-[(E)-(methoxyimino)-methyl]-1,1'-biphenyl-2-yl}-1-methyl-1H-pyrazole-4-carboxamide | (3-3) propiconazole |
| B-12 | (1-3) 3-(trifluoromethyl)-N-{3'-fluoro-4'-[(E)-(methoxyimino)-methyl]-1,1'-biphenyl-2-yl}-1-methyl-1H-pyrazole-4-carboxamide | (3-6) cyproconazole |
| B-13 | (1-3) 3-(trifluoromethyl)-N-{3'-fluoro-4'-[(E)-(methoxyimino)-methyl]-1,1'-biphenyl-2-yl}-1-methyl-1H-pyrazole-4-carboxamide | (3-15) prothioconazole |

TABLE 2-continued

Active compound combinations B

| No. | Carboxamide of the formula (I) | Triazole of the formula (III) |
|---|---|---|
| B-14 | (1-3) 3-(trifluoromethyl)-N-{3'-fluoro-4'-[(E)-(methoxyimino)-methyl]-1,1'-biphenyl-2-yl}-1-methyl-1H-pyrazole-4-carboxamide | (3-17) tebuconazole |
| B-15 | (1-3) 3-(trifluoromethyl)-N-{3'-fluoro-4'-[(E)-(methoxyimino)-methyl]-1,1'-biphenyl-2-yl}-1-methyl-1H-pyrazole-4-carboxamide | (3-21) bitertanol |
| B-16 | (1-4) N-(3',4'-dichloro-1,1'-biphenyl-2-yl)-5-fluoro-1,3-dimethyl-1H-pyrazole-4-carboxamide | (3-3) propiconazole |
| B-17 | (1-4) N-(3',4'-dichloro-1,1'-biphenyl-2-yl)-5-fluoro-1,3-dimethyl-1H-pyrazole-4-carboxamide | (3-6) cyproconazole |
| B-18 | (1-4) N-(3',4'-dichloro-1,1'-biphenyl-2-yl)-5-fluoro-1,3-dimethyl-1H-pyrazole-4-carboxamide | (3-15) prothioconazole |
| B-19 | (1-4) N-(3',4'-dichloro-1,1'-biphenyl-2-yl)-5-fluoro-1,3-dimethyl-1H-pyrazole-4-carboxamide | (3-17) tebuconazole |
| B-20 | (1-4) N-(3',4'-dichloro-1,1'-biphenyl-2-yl)-5-fluoro-1,3-dimethyl-1H-pyrazole-4-carboxamide | (3-21) bitertanol |
| B-21 | (1-5) N-(4'-chloro-3'-fluoro-1,1'-biphenyl-2-yl)-2-methyl-4-(trifluoromethyl)-1,3-thiazole-5-carboxamide | (3-3) propiconazole |
| B-22 | (1-5) N-(4'-chloro-3'-fluoro-1,1'-biphenyl-2-yl)-2-methyl-4-(trifluoromethyl)-1,3-thiazole-5-carboxamide | (3-6) cyproconazole |
| B-23 | (1-5) N-(4'-chloro-3'-fluoro-1,1'-biphenyl-2-yl)-2-methyl-4-(trifluoromethyl)-1,3-thiazole-5-carboxamide | (3-15) prothioconazole |
| B-24 | (1-5) N-(4'-chloro-3'-fluoro-1,1'-biphenyl-2-yl)-2-methyl-4-(trifluoromethyl)-1,3-thiazole-5-carboxamide | (3-17) tebuconazole |
| B-25 | (1-5) N-(4'-chloro-3'-fluoro-1,1'-biphenyl-2-yl)-2-methyl-4-(trifluoromethyl)-1,3-thiazole-5-carboxamide | (3-21) bitertanol |
| B-26 | (1-6) N-(4'-chloro-1,1'-biphenyl-2-yl)-4-(difluoromethyl)-2-methyl-1,3-thiazole-5-carboxamide | (3-3) propiconazole |
| B-27 | (1-6) N-(4'-chloro-1,1'-biphenyl-2-yl)-4-(difluoromethyl)-2-methyl-1,3-thiazole-5-carboxamide | (3-6) cyproconazole |
| B-28 | (1-6) N-(4'-chloro-1,1'-biphenyl-2-yl)-4-(difluoromethyl)-2-methyl-1,3-thiazole-5-carboxamide | (3-15) prothioconazole |
| B-29 | (1-6) N-(4'-chloro-1,1'-biphenyl-2-yl)-4-(difluoromethyl)-2-methyl-1,3-thiazole-5-carboxamide | (3-17) tebuconazole |
| B-30 | (1-6) N-(4'-chloro-1,1'-biphenyl-2-yl)-4-(difluoromethyl)-2-methyl-1,3-thiazole-5-carboxamide | (3-21) bitertanol |
| B-31 | (1-7) N-(4'-bromo-1,1'-biphenyl-2-yl)-4-(difluoromethyl)-2-methyl-1,3-thiazole-5-carboxamide | (3-3) propiconazole |
| B-32 | (1-7) N-(4'-bromo-1,1'-biphenyl-2-yl)-4-(difluoromethyl)-2-methyl-1,3-thiazole-5-carboxamide | (3-6) cyproconazole |
| B-33 | (1-7) N-(4'-bromo-1,1'-biphenyl-2-yl)-4-(difluoromethyl)-2-methyl-1,3-thiazole-5-carboxamide | (3-15) prothioconazole |
| B-34 | (1-7) N-(4'-bromo-1,1'-biphenyl-2-yl)-4-(difluoromethyl)-2-methyl-1,3-thiazole-5-carboxamide | (3-17) tebuconazole |
| B-35 | (1-7) N-(4'-bromo-1,1'-biphenyl-2-yl)-4-(difluoromethyl)-2-methyl-1,3-thiazole-5-carboxamide | (3-21) bitertanol |
| B-36 | (1-8) 4-(difluoromethyl)-2-methyl-N-[4'-(trifluoromethyl)-1,1'-biphenyl-2-yl]-1,3-thiazole-5-carboxamide | (3-3) propiconazole |
| B-37 | (1-8) 4-(difluoromethyl)-2-methyl-N-[4'-(trifluoromethyl)-1,1'-biphenyl-2-yl]-1,3-thiazole-5-carboxamide | (3-6) cyproconazole |
| B-38 | (1-8) 4-(difluoromethyl)-2-methyl-N-[4'-(trifluoromethyl)-1,1'-biphenyl-2-yl]-1,3-thiazole-5-carboxamide | (3-15) prothioconazole |
| B-39 | (1-8) 4-(difluoromethyl)-2-methyl-N-[4'-(trifluoromethyl)-1,1'-biphenyl-2-yl]-1,3-thiazole-5-carboxamide | (3-17) tebuconazole |
| B-40 | (1-8) 4-(difluoromethyl)-2-methyl-N-[4'-(trifluoromethyl)-1,1'-biphenyl-2-yl]-1,3-thiazole-5-carboxamide | (3-21) bitertanol |
| B-41 | (1-1) N-(3',4'-dichloro-5-fluoro-1,1'-biphenyl-2-yl)-3-(difluoromethyl)-1-methyl-1H-pyrazole-4-carboxamide | (3-4) difenoconazole |
| B-42 | (1-1) N-(3',4'-dichloro-5-fluoro-1,1'-biphenyl-2-yl)-3-(difluoromethyl)-1-methyl-1H-pyrazole-4-carboxamide | (3-7) hexaconazole |
| B-43 | (1-1) N-(3',4'-dichloro-5-fluoro-1,1'-biphenyl-2-yl)-3-(difluoromethyl)-1-methyl-1H-pyrazole-4-carboxamide | (3-19) metconazole |
| B-44 | (1-1) N-(3',4'-dichloro-5-fluoro-1,1'-biphenyl-2-yl)-3-(difluoromethyl)-1-methyl-1H-pyrazole-4-carboxamide | (3-22) triadimenol |
| B-45 | (1-1) N-(3',4'-dichloro-5-fluoro-1,1'-biphenyl-2-yl)-3-(difluoromethyl)-1-methyl-1H-pyrazole-4-carboxamide | (3-24) fluquinconazole |
| B-46 | (1-7) N-(4'-bromo-1,1'-biphenyl-2-yl)-4-(difluoromethyl)-2-methyl-1,3-thiazole-5-carboxamide | (3-4) difenoconazole |
| B-47 | (1-7) N-(4'-bromo-1,1'-biphenyl-2-yl)-4-(difluoromethyl)-2-methyl-1,3-thiazole-5-carboxamide | (3-7) hexaconazole |
| B-48 | (1-7) N-(4'-bromo-1,1'-biphenyl-2-yl)-4-(difluoromethyl)-2-methyl-1,3-thiazole-5-carboxamide | (3-19) metconazole |
| B-49 | (1-7) N-(4'-bromo-1,1'-biphenyl-2-yl)-4-(difluoromethyl)-2-methyl-1,3-thiazole-5-carboxamide | (3-22) triadimenol |

TABLE 2-continued

Active compound combinations B

| No. | Carboxamide of the formula (I) | Triazole of the formula (III) |
|---|---|---|
| B-50 | (1-7) N-(4'-bromo-1,1'-biphenyl-2-yl)-4-(difluoromethyl)-2-methyl-1,3-thiazole-5-carboxamide | (3-24) fluquinconazole |
| B-51 | (1-8) 4-(difluoromethyl)-2-methyl-N-[4'-(trifluoromethyl)-1,1'-biphenyl-2-yl]-1,3-thiazole-5-carboxamide | (3-4) difenoconazole |
| B-52 | (1-8) 4-(difluoromethyl)-2-methyl-N-[4'-(trifluoromethyl)-1,1'-biphenyl-2-yl]-1,3-thiazole-5-carboxamide | (3-7) hexaconazole |
| B-53 | (1-8) 4-(difluoromethyl)-2-methyl-N-[4'-(trifluoromethyl)-1,1'-biphenyl-2-yl]-1,3-thiazole-5-carboxamide | (3-19) metconazole |
| B-54 | (1-8) 4-(difluoromethyl)-2-methyl-N-[4'-(trifluoromethyl)-1,1'-biphenyl-2-yl]-1,3-thiazole-5-carboxamide | (3-22) triadimenol |
| B-55 | (1-8) 4-(difluoromethyl)-2-methyl-N-[4'-(trifluoromethyl)-1,1'-biphenyl-2-yl]-1,3-thiazole-5-carboxamide | (3-24) fluquinconazole |
| B-56 | (1-9) N-(4'-chloro-3'-fluoro-1,1'-biphenyl-2-yl)-4-(difluoromethyl)-2-methyl-1,3-thiazole-5-carboxamide | (3-4) difenoconazole |
| B-57 | (1-9) N-(4'-chloro-3'-fluoro-1,1'-biphenyl-2-yl)-4-(difluoromethyl)-2-methyl-1,3-thiazole-5-carboxamide | (3-7) hexaconazole |
| B-58 | (1-9) N-(4'-chloro-3'-fluoro-1,1'-biphenyl-2-yl)-4-(difluoromethyl)-2-methyl-1,3-thiazole-5-carboxamide | (3-19) metconazole |
| B-59 | (1-9) N-(4'-chloro-3'-fluoro-1,1'-biphenyl-2-yl)-4-(difluoromethyl)-2-methyl-1,3-thiazole-5-carboxamide | (3-22) triadimenol |
| B-60 | (1-9) N-(4'-chloro-3'-fluoro-1,1'-biphenyl-2-yl)-4-(difluoromethyl)-2-methyl-1,3-thiazole-5-carboxamide | (3-24) fluquinconazole |
| B-61 | (1-9) N-(4'-chloro-3'-fluoro-1,1'-biphenyl-2-yl)-4-(difluoromethyl)-2-methyl-1,3-thiazole-5-carboxamide | (3-3) propiconazole |
| B-62 | (1-9) N-(4'-chloro-3'-fluoro-1,1'-biphenyl-2-yl)-4-(difluoromethyl)-2-methyl-1,3-thiazole-5-carboxamide | (3-6) cyproconazole |
| B-63 | (1-9) N-(4'-chloro-3'-fluoro-1,1'-biphenyl-2-yl)-4-(difluoromethyl)-2-methyl-1,3-thiazole-5-carboxamide | (3-15) prothioconazole |
| B-64 | (1-9) N-(4'-chloro-3'-fluoro-1,1'-biphenyl-2-yl)-4-(difluoromethyl)-2-methyl-1,3-thiazole-5-carboxamide | (3-17) tebuconazole |
| B-65 | (1-9) N-(4'-chloro-3'-fluoro-1,1'-biphenyl-2-yl)-4-(difluoromethyl)-2-methyl-1,3-thiazole-5-carboxamide | (3-21) bitertanol |

In addition to a carboxamide of the formula (I) (group 1), the active compound combinations C also comprise a sulphonamide of the formula (IV) (group 4)

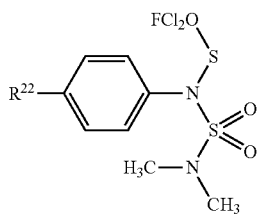

(IV)

in which $R^{22}$ is as defined above.

Preference is given to active compound combinations C in which the sulphonamide of the formula (IV) (group 4) is selected from the following list:
(4-1) dichlofluanid
(4-2) tolylfluanid Emphasis is given to the active compound combinations C listed in Table 3 below:

TABLE 3

Active compound combinations C

| No. | Carboxamide of the formula (I) | Sulphenamide of the formula (IV) |
|---|---|---|
| C-1 | (1-1) N-(3',4'-dichloro-5-fluoro-1,1'-biphenyl-2-yl)-3-(difluoromethyl)-1-methyl-1H-pyrazole-4-carboxamide | (4-1) dichlofluanid |
| C-2 | (1-1) N-(3',4'-dichloro-5-fluoro-1,1'-biphenyl-2-yl)-3-(difluoromethyl)-1-methyl-1H-pyrazole-4-carboxamide | (4-2) tolylfluanid |
| C-3 | (1-7) N-(4'-bromo-1,1'-biphenyl-2-yl)-4-(difluoromethyl)-2-methyl-1,3-thiazole-5-carboxamide | (4-1) dichlofluanid |
| C-4 | (1-7) N-(4'-bromo-1,1'-biphenyl-2-yl)-4-(difluoromethyl)-2-methyl-1,3-thiazole-5-carboxamide | (4-2) tolylfluanid |
| C-5 | (1-8) 4-(difluoromethyl)-2-methyl-N-[4'-(trifluoromethyl)-1,1'-biphenyl-2-yl]-1,3-thiazole-5-carboxamide | (4-1) dichlofluanid |
| C-6 | (1-8) 4-(difluoromethyl)-2-methyl-N-[4'-(trifluoromethyl)-1,1'-biphenyl-2-yl]-1,3-thiazole-5-carboxamide | (4-2) tolylfluanid |
| C-7 | (1-9) N-(4'-chloro-3'-fluoro-1,1'-biphenyl-2-yl)-4-(difluoromethyl)-2-methyl-1,3-thiazole-5-carboxamide | (4-1) dichlofluanid |
| C-8 | (1-9) N-(4'-chloro-3'-fluoro-1,1'-biphenyl-2-yl)-4-(difluoromethyl)-2-methyl-1,3-thiazole-5-carboxamide | (4-2) tolylfluanid |

In addition to a carboxamide of the formula (I) (group 1), the active compound combinations D also comprise a valinamide (group 5) selected from
(5-1) iprovalicarb
(5-2) N'-[2-(4-{[3-(4-chlorophenyl)-2-propynyl]oxy}-3-methoxyphenyl)ethyl]-N²-(methyl-sulphonyl)-D-valinamide (5-3) benthiavalicarb Preference is given to active compound combinations D in which the valinamide (group 5) is selected from the following list:
(5-1) iprovalicarb
(5-3) benthiavalicarb Emphasis is given to the active compound combinations D listed in Table 4 below:

TABLE 4

Active compound combinations D

| No. | Carboxamide of the formula (I) | Valinamide |
|---|---|---|
| D-1 | (1-1) N-(3',4'-dichloro-5-fluoro-1,1'-biphenyl-2-yl)-3-(difluoromethyl)-1-methyl-1H-pyrazole-4-carboxamide | (5-1) iprovalicarb |
| D-2 | (1-1) N-(3',4'-dichloro-5-fluoro-1,1'-biphenyl-2-yl)-3-(difluoromethyl)-1-methyl-1H-pyrazole-4-carboxamide | (5-2) benthiavalicarb |
| D-3 | (1-7) N-(4'-bromo-1,1'-biphenyl-2-yl)-4-(difluoromethyl)-2-methyl-1,3-thiazole-5-carboxamide | (5-1) iprovalicarb |
| D-4 | (1-7) N-(4'-bromo-1,1'-biphenyl-2-yl)-4-(difluoromethyl)-2-methyl-1,3-thiazole-5-carboxamide | (5-2) benthiavalicarb |
| D-5 | (1-8) 4-(difluoromethyl)-2-methyl-N-[4'-(trifluoromethyl)-1,1'-biphenyl-2-yl]-1,3-thiazole-5-carboxamide | (5-1) iprovalicarb |
| D-6 | (1-8) 4-(difluoromethyl)-2-methyl-N-[4'-(trifluoromethyl)-1,1'-biphenyl-2-yl]-1,3-thiazole-5-carboxamide | (5-2) benthiavalicarb |
| D-7 | (1-9) N-(4'-chloro-3'-fluoro-1,1'-biphenyl-2-yl)-4-(difluoromethyl)-2-methyl-1,3-thiazole-5-carboxamide | (5-1) iprovalicarb |
| D-8 | (1-9) N-(4'-chloro-3'-fluoro-1,1'-biphenyl-2-yl)-4-(difluoromethyl)-2-methyl-1,3-thiazole-5-carboxamide | (5-2) benthiavalicarb |

In addition to a carboxamide of the formula (I) (group 1), the active compound combinations E also comprise a carboxamide of the formula (V) (group 6)

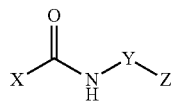

in which X, Y and Z are as defined above.

Preference is given to active compound combinations E in which the carboxamide of the formula (V) (group 6) is selected from the list below:
(6-1) 2-chloro-N-(1,1,3-trimethylindan-4-yl)nicotinamide
(6-2) boscalid
(6-3) furametpyr
(6-4) N-(3-p-tolylthiophen-2-yl)-1-methyl-3-trifluoromethyl-1H-pyrazole-4-carboxamide
(6-5) ethaboxam
(6-6) fenhexamid
(6-7) carpropamid
(6-8) 2-chloro-4-(2-fluoro-2-methylpropionylamino)-N,N-dimethylbenzamide
(6-9) picobenzamid
(6-10) zoxamide
(6-11) 3,4-dichloro-N-(2-cyanophenyl)isothiazole-5-carboxamide
(6-12) carboxin
(6-13) tiadinil
(6-14) penthiopyrad
(6-15) silthiofam
(6-16) N-[2-(1,3-dimethylbutyl)phenyl]-1-methyl-4-(trifluoromethyl)-1H-pyrrole-3-carboxamide Particular preference is given to active compound combinations E in which the carboxamide of the formula (V) (group 6) is selected from the list below:
(6-2) boscalid
(6-5) ethaboxam
(6-6) fenhexamid
(6-7) carpropamid
(6-8) 2-chloro-4-(2-fluoro-2-methylpropionylamino)-N,N-dimethylbenzamide
(6-9) picobenzamid
(6-10) zoxamide
(6-11) 3,4-dichloro-N-(2-cyanophenyl)isothiazole-5-carboxamide
(6-14) penthiopyrad
(6-16) N-[2-(1,3-dimethylbutyl)phenyl]-1-methyl-4-(trifluoromethyl)-1H-pyrrole-3-carboxamide Very particular preference is given to active compound combinations E in which the carboxamide of the formula (V) (group 6) is selected from the list below:
(6-2) boscalid
(6-6) fenhexamid
(6-7) carpropamid
(6-9) picobenzamid
(6-14) penthiopyrad Emphasis is given to the active compound combinations E listed in Table 5 below:

TABLE 5

Active compound combinations E

| No. | Carboxamide of the formula (I) | Carboxamide of the formula (V) |
|---|---|---|
| E-1 | (1-1) N-(3',4'-dichloro-5-fluoro-1,1'-biphenyl-2-yl)-3-(difluoromethyl)-1-methyl-1H-pyrazole-4-carboxamide | (6-2) boscalid |
| E-2 | (1-1) N-(3',4'-dichloro-5-fluoro-1,1'-biphenyl-2-yl)-3-(difluoromethyl)-1-methyl-1H-pyrazole-4-carboxamide | (6-6) fenhexamid |

TABLE 5-continued

Active compound combinations E

| No. | Carboxamide of the formula (I) | Carboxamide of the formula (V) |
|---|---|---|
| E-3 | (1-1) N-(3',4'-dichloro-5-fluoro-1,1'-biphenyl-2-yl)-3-(difluoromethyl)-1-methyl-1H-pyrazole-4-carboxamide | (6-7) carpropamid |
| E-4 | (1-1) N-(3',4'-dichloro-5-fluoro-1,1'-biphenyl-2-yl)-3-(difluoromethyl)-1-methyl-1H-pyrazole-4-carboxamide | (6-9) picobenzamid |
| E-5 | (1-1) N-(3',4'-dichloro-5-fluoro-1,1'-biphenyl-2-yl)-3-(difluoromethyl)-1-methyl-1H-pyrazole-4-carboxamide | (6-14) penthiopyrad |
| E-6 | (1-7) N-(4'-bromo-1,1'-biphenyl-2-yl)-4-(difluoromethyl)-2-methyl-1,3-thiazole-5-carboxamide | (6-2) boscalid |
| E-7 | (1-7) N-(4'-bromo-1,1'-biphenyl-2-yl)-4-(difluoromethyl)-2-methyl-1,3-thiazole-5-carboxamide | (6-6) fenhexamid |
| E-8 | (1-7) N-(4'-bromo-1,1'-biphenyl-2-yl)-4-(difluoromethyl)-2-methyl-1,3-thiazole-5-carboxamide | (6-7) carpropamid |
| E-9 | (1-7) N-(4'-bromo-1,1'-biphenyl-2-yl)-4-(difluoromethyl)-2-methyl-1,3-thiazole-5-carboxamide | (6-9) picobenzamid |
| E-10 | (1-7) N-(4'-bromo-1,1'-biphenyl-2-yl)-4-(difluoromethyl)-2-methyl-1,3-thiazole-5-carboxamide | (6-14) penthiopyrad |
| E-11 | (1-8) 4-(difluoromethyl)-2-methyl-N-[4'-(trifluoromethyl)-1,1'-biphenyl-2-yl]-1,3-thiazole-5-carboxamide | (6-2) boscalid |
| E-12 | (1-8) 4-(difluoromethyl)-2-methyl-N-[4'-(trifluoromethyl)-1,1'-biphenyl-2-yl]-1,3-thiazole-5-carboxamide | (6-6) fenhexamid |
| E-13 | (1-8) 4-(difluoromethyl)-2-methyl-N-[4'-(trifluoromethyl)-1,1'-biphenyl-2-yl]-1,3-thiazole-5-carboxamide | (6-7) carpropamid |
| E-14 | (1-8) 4-(difluoromethyl)-2-methyl-N-[4'-(trifluoromethyl)-1,1'-biphenyl-2-yl]-1,3-thiazole-5-carboxamide | (6-9) picobenzamid |
| E-15 | (1-8) 4-(difluoromethyl)-2-methyl-N-[4'-(trifluoromethyl)-1,1'-biphenyl-2-yl]-1,3-thiazole-5-carboxamide | (6-14) penthiopyrad |
| E-16 | (1-9) N-(4'-chloro-3'-fluoro-1,1'-biphenyl-2-yl)-4-(difluoromethyl)-2-methyl-1,3-thiazole-5-carboxamide | (6-2) boscalid |
| E-17 | (1-9) N-(4'-chloro-3'-fluoro-1,1'-biphenyl-2-yl)-4-(difluoromethyl)-2-methyl-1,3-thiazole-5-carboxamide | (6-6) fenhexamid |
| E-18 | (1-9) N-(4'-chloro-3'-fluoro-1,1'-biphenyl-2-yl)-4-(difluoromethyl)-2-methyl-1,3-thiazole-5-carboxamide | (6-7) carpropamid |
| E-19 | (1-9) N-(4'-chloro-3'-fluoro-1,1'-biphenyl-2-yl)-4-(difluoromethyl)-2-methyl-1,3-thiazole-5-carboxamide | (6-9) picobenzamid |
| E-20 | (1-9) N-(4'-chloro-3'-fluoro-1,1'-biphenyl-2-yl)-4-(difluoromethyl)-2-methyl-1,3-thiazole-5-carboxamide | (6-14) penthiopyrad |

In addition to a carboxamide of the formula (I) (group 1), the active compound combinations F also comprise a dithiocarbamate (group 7) selected from
(7-1) mancozeb
(7-2) maneb
(7-3) metiram
(7-4) propineb
(7-5) thiram
(7-6) zineb
(7-7) ziram Preference is given to active compound combinations F in which the dithiocarbamate (group 7) is selected from the following list:
(7-1) mancozeb
(7-2) maneb
(7-4) propineb
(7-5) thiram
(7-6) zineb Particular preference is given to active compound combinations F in which the dithiocarbamate (group 7) is selected from the following list:

(7-1) mancozeb
(7-4) propineb

Emphasis is given to the active compound combinations F listed in Table 6 below:

TABLE 6

Active compound combinations F

| No. | Carboxamide of the formula (I) | Dithiocarbamate |
|---|---|---|
| F-1 | (1-1) N-(3',4'-dichloro-5-fluoro-1,1'-biphenyl-2-yl)-3-(difluoromethyl)-1-methyl-1H-pyrazole-4-carboxamide | (7-1) mancozeb |
| F-2 | (1-1) N-(3',4'-dichloro-5-fluoro-1,1'-biphenyl-2-yl)-3-(difluoromethyl)-1-methyl-1H-pyrazole-4-carboxamide | (7-4) propineb |
| F-3 | (1-7) N-(4'-bromo-1,1'-biphenyl-2-yl)-4-(difluoromethyl)-2-methyl-1,3-thiazole-5-carboxamide | (7-1) mancozeb |
| F-4 | (1-7) N-(4'-bromo-1,1'-biphenyl-2-yl)-4-(difluoromethyl)-2-methyl-1,3-thiazole-5-carboxamide | (7-4) propineb |
| F-5 | (1-8) 4-(difluoromethyl)-2-methyl-N-[4'-(trifluoromethyl)-1,1'-biphenyl-2-yl]-1,3-thiazole-5-carboxamide | (7-1) mancozeb |

TABLE 6-continued

Active compound combinations F

| No. | Carboxamide of the formula (I) | Dithiocarbamate |
|---|---|---|
| F-6 | (1-8) 4-(difluoromethyl)-2-methyl-N-[4'-(trifluoromethyl)-1,1'-biphenyl-2-yl]-1,3-thiazole-5-carboxamide | (7-4) propineb |
| F-7 | (1-9) N-(4'-chloro-3'-fluoro-1,1'-biphenyl-2-yl)-4-(difluoromethyl)-2-methyl-1,3-thiazole-5-carboxamide | (7-1) mancozeb |
| F-8 | (1-9) N-(4'-chloro-3'-fluoro-1,1'-biphenyl-2-yl)-4-(difluoromethyl)-2-methyl-1,3-thiazole-5-carboxamide | (7-4) propineb |

In addition to a carboxamide of the formula (I) (group 1), the active compound combinations G also comprise an acylalanine of the formula (VI) (group 8)

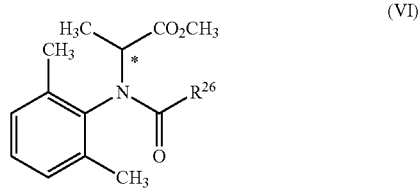

(VI)

in which * and $R^{26}$ are as defined above.

Preference is given to active compound combinations G in which the acylalanine of the formula (VI) (group 8) is selected from the following list:
(8-1) benalaxyl
(8-2) furalaxyl
(8-3) metalaxyl
(8-4) metalaxyl-M
(8-5) benalaxyl-M Particular preference is given to active compound combinations G in which the acylalanine of the formula (VI) (group 8) is selected from the following list:
(8-3) metalaxyl
(8-4) metalaxyl-M
(8-5) benalaxyl-M Emphasis is given to the active compound combinations G listed in Table 7 below:

TABLE 7

Active compound combinations G

| No. | Carboxamide of the formula (I) | Acylalanine of the formula (VI) |
|---|---|---|
| G-1 | (1-1) N-(3',4'-dichloro-5-fluoro-1,1'-biphenyl-2-yl)-3-(difluoromethyl)-1-methyl-1H-pyrazole-4-carboxamide | (8-3) metalaxyl |
| G-2 | (1-1) N-(3',4'-dichloro-5-fluoro-1,1'-biphenyl-2-yl)-3-(difluoromethyl)-1-methyl-1H-pyrazole-4-carboxamide | (8-4) metalaxyl-M |
| G-3 | (1-1) N-(3',4'-dichloro-5-fluoro-1,1'-biphenyl-2-yl)-3-(difluoromethyl)-1-methyl-1H-pyrazole-4-carboxamide | (8-5) benalaxyl-M |
| G-4 | (1-7) N-(4'-bromo-1,1'-biphenyl-2-yl)-4-(difluoromethyl)-2-methyl-1,3-thiazole-5-carboxamide | (8-3) metalaxyl |
| G-5 | (1-7) N-(4'-bromo-1,1'-biphenyl-2-yl)-4-(difluoromethyl)-2-methyl-1,3-thiazole-5-carboxamide | (8-4) metalaxyl-M |
| G-6 | (1-7) N-(4'-bromo-1,1'-biphenyl-2-yl)-4-(difluoromethyl)-2-methyl-1,3-thiazole-5-carboxamide | (8-5) benalaxyl-M |
| G-7 | (1-8) 4-(difluoromethyl)-2-methyl-N-[4'-(trifluoromethyl)-1,1'-biphenyl-2-yl]-1,3-thiazole-5-carboxamide | (8-3) metalaxyl |
| G-8 | (1-8) 4-(difluoromethyl)-2-methyl-N-[4'-(trifluoromethyl)-1,1'-biphenyl-2-yl]-1,3-thiazole-5-carboxamide | (8-4) metalaxyl-M |
| G-9 | (1-8) 4-(difluoromethyl)-2-methyl-N-[4'-(trifluoromethyl)-1,1'-biphenyl-2-yl]-1,3-thiazole-5-carboxamide | (8-5) benalaxyl-M |
| G-10 | (1-9) N-(4'-chloro-3'-fluoro-1,1'-biphenyl-2-yl)-4-(difluoromethyl)-2-methyl-1,3-thiazole-5-carboxamide | (8-3) metalaxyl |
| G-11 | (1-9) N-(4'-chloro-3'-fluoro-1,1'-biphenyl-2-yl)-4-(difluoromethyl)-2-methyl-1,3-thiazole-5-carboxamide | (8-4) metalaxyl-M |
| G-12 | (1-9) N-(4'-chloro-3'-fluoro-1,1'-biphenyl-2-yl)-4-(difluoromethyl)-2-methyl-1,3-thiazole-5-carboxamide | (8-5) benalaxyl-M |

In addition to a carboxamide of the formula (I) (group 1), the active compound combinations H also comprise an anilinopyrimidine (group 9) selected from
(9-1) cyprodinil
(9-2) mepanipyrim
(9-3) pyrimethanil Emphasis is given to the active compound combinations H listed in Table 8 below:

TABLE 8

Active compound combinations H

| No. | Carboxamide of the formula (I) | Anilinopyrimidine |
|---|---|---|
| H-1 | (1-1) N-(3',4'-dichloro-5-fluoro-1,1'-biphenyl-2-yl)-3-(difluoromethyl)-1-methyl-1H-pyrazole-4-carboxamide | (9-1) cyprodinil |
| H-2 | (1-1) N-(3',4'-dichloro-5-fluoro-1,1'-biphenyl-2-yl)-3-(difluoromethyl)-1-methyl-1H-pyrazole-4-carboxamide | (9-2) mepanipyrim |
| H-3 | (1-1) N-(3',4'-dichloro-5-fluoro-1,1'-biphenyl-2-yl)-3-(difluoromethyl)-1-methyl-1H-pyrazole-4-carboxamide | (9-3) pyrimethanil |
| H-4 | (1-7) N-(4'-bromo-1,1'-biphenyl-2-yl)-4-(difluoromethyl)-2-methyl-1,3-thiazole-5-carboxamide | (9-1) cyprodinil |
| H-5 | (1-7) N-(4'-bromo-1,1'-biphenyl-2-yl)-4-(difluoromethyl)-2-methyl-1,3-thiazole-5-carboxamide | (9-2) mepanipyrim |
| H-6 | (1-7) N-(4'-bromo-1,1'-biphenyl-2-yl)-4-(difluoromethyl)-2-methyl-1,3-thiazole-5-carboxamide | (9-3) pyrimethanil |
| H-7 | (1-8) 4-(difluoromethyl)-2-methyl-N-[4'-(trifluoromethyl)-1,1'-biphenyl-2-yl]-1,3-thiazole-5-carboxamide | (9-1) cyprodinil |
| H-8 | (1-8) 4-(difluoromethyl)-2-methyl-N-[4'-(trifluoromethyl)-1,1'-biphenyl-2-yl]-1,3-thiazole-5-carboxamide | (9-2) mepanipyrim |
| H-9 | (1-8) 4-(difluoromethyl)-2-methyl-N-[4'-(trifluoromethyl)-1,1'-biphenyl-2-yl]-1,3-thiazole-5-carboxamide | (9-3) pyrimethanil |

TABLE 8-continued

Active compound combinations H

| No. | Carboxamide of the formula (I) | Anilinopyrimidine |
|---|---|---|
| H-10 | (1-9) N-(4'-chloro-3'-fluoro-1,1'-biphenyl-2-yl)-4-(difluoromethyl)-2-methyl-1,3-thiazole-5-carboxamide | (9-1) cyprodinil |
| H-11 | (1-9) N-(4'-chloro-3'-fluoro-1,1'-biphenyl-2-yl)-4-(difluoromethyl)-2-methyl-1,3-thiazole-5-carboxamide | (9-2) mepanipyrim |
| H-12 | (1-9) N-(4'-chloro-3'-fluoro-1,1'-biphenyl-2-yl)-4-(difluoromethyl)-2-methyl-1,3-thiazole-5-carboxamide | (9-3) pyrimethanil |

In addition to a carboxamide of the formula (I) (group 1), the active compound combinations I also comprise a benzimidazole of the formula (VIII) (group 10)

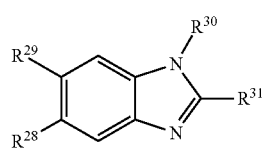

in which $R^{28}$, $R^{29}$, $R^{30}$ and $R^{31}$ are as defined above.

Preference is given to active compound combinations I in which the benzimidazole of the formula (VIII) (group 10) is selected form the following list:
(10-1) 6-chloro-5-[(3,5-dimethylisoxazol-4-yl)sulphonyl]-2,2-difluoro-5H-[1,3]dioxolo[4,5-f]-benzimidazole
(10-2) benomyl
(10-3) carbendazim
(10-4) chlorfenazole
(10-5) fuberidazole
(10-6) thiabendazole Particular preference is given to active compound combinations I in which the benzimidazole of the formula (VIII) (group 10) is:
(10-3) carbendazim Emphasis is given to the active compound combinations I listed in Table 9 below:

TABLE 9

Active compound combinations I

| No. | Carboxamide of the formula (I) | Benzimidazole of the formula (VIII) |
|---|---|---|
| I-1 | (1-1) N-(3',4'-dichloro-5-fluoro-1,1'-biphenyl-2-yl)-3-(difluoromethyl)-1-methyl-1H-pyrazole-4-carboxamide | (10-3) carbendazim |
| I-2 | (1-7) N-(4'-bromo-1,1'-biphenyl-2-yl)-4-(difluoromethyl)-2-methyl-1,3-thiazole-5-carboxamide | (10-3) carbendazim |
| I-3 | (1-8) 4-(difluoromethyl)-2-methyl-N-[4'-(trifluoromethyl)-1,1'-biphenyl-2-yl]-1,3-thiazole-5-carboxamide | (10-3) carbendazim |
| I-4 | (1-9) N-(4'-chloro-3'-fluoro-1,1'-biphenyl-2-yl)-4-(difluoromethyl)-2-methyl-1,3-thiazole-5-carboxamide | (10-3) carbendazim |

In addition to a carboxamide of the formula (I) (group 1), the active compound combinations J also comprise a carbamate (group 11) of the formula (IX)

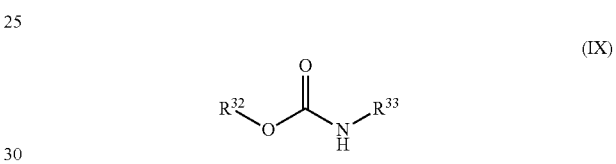

in which $R^{32}$ and $R^{33}$ are as defined above.

Preference is given to active compound combinations J in which the carbamate (group 11) is selected from the following list:
(11-1) diethofencarb
(11-2) propamocarb
(11-3) propamocarb-hydrochloride
(11-4) propamocarb-fosetyl Emphasis is given to the active compound combinations J listed in Table 10 below:

TABLE 10

Active compound combinations J

| No. | Carboxamide of the formula (I) | Carbamate of the formula (IX) |
|---|---|---|
| J-1 | (1-1) N-(3',4'-dichloro-5-fluoro-1,1'-biphenyl-2-yl)-3-(difluoromethyl)-1-methyl-1H-pyrazole-4-carboxamide | (11-2) propamocarb |
| J-2 | (1-1) N-(3',4'-dichloro-5-fluoro-1,1'-biphenyl-2-yl)-3-(difluoromethyl)-1-methyl-1H-pyrazole-4-carboxamide | (11-3) propamocarb-hydrochloride |
| J-3 | (1-1) N-(3',4'-dichloro-5-fluoro-1,1'-biphenyl-2-yl)-3-(difluoromethyl)-1-methyl-1H-pyrazole-4-carboxamide | (11-4) propamocarb-fosetyl |
| J-4 | (1-7) N-(4'-bromo-1,1'-biphenyl-2-yl)-4-(difluoromethyl)-2-methyl-1,3-thiazole-5-carboxamide | (11-2) propamocarb |
| J-5 | (1-7) N-(4'-bromo-1,1'-biphenyl-2-yl)-4-(difluoromethyl)-2-methyl-1,3-thiazole-5-carboxamide | (11-3) propamocarb-hydrochloride |
| J-6 | (1-7) N-(4'-bromo-1,1'-biphenyl-2-yl)-4-(difluoromethyl)-2-methyl-1,3-thiazole-5-carboxamide | (11-4) propamocarb-fosetyl |
| J-7 | (1-8) 4-(difluoromethyl)-2-methyl-N-[4'-(trifluoromethyl)-1,1'-biphenyl-2-yl]-1,3-thiazole-5-carboxamide | (11-2) propamocarb |
| J-8 | (1-8) 4-(difluoromethyl)-2-methyl-N-[4'-(trifluoromethyl)-1,11-biphenyl-2-yl]-1,3-thiazole-5-carboxamide | (11-3) propamocarb-hydrochloride |
| J-9 | (1-8) 4-(difluoromethyl)-2-methyl-N-[4'-(trifluoromethyl)-1,1'-biphenyl-2-yl]-1,3-thiazole-5-carboxamide | (11-4) propamocarb-fosetyl |
| J-10 | (1-9) N-(4'-chloro-3'-fluoro-1,1'-biphenyl-2-yl)-4-(difluoromethyl)-2-methyl-1,3-thiazole-5-carboxamide | (11-2) propamocarb |
| J-11 | (1-9) N-(4'-chloro-3'-fluoro-1,1'-biphenyl-2-yl)-4-(difluoromethyl)-2-methyl-1,3-thiazole-5-carboxamide | (11-3) propamocarb-hydrochloride |

TABLE 10-continued

Active compound combinations J

| No. | Carboxamide of the formula (I) | Carbamate of the formula (IX) |
|---|---|---|
| J-12 | (1-9) N-(4'-chloro-3'-fluoro-1,1'-biphenyl-2-yl)-4-(difluoromethyl)-2-methyl-1,3-thiazole-5-carboxamide | (11-4) propamocarb-fosetyl |

In addition to a carboxamide of the formula (I) (group 1), the active compound combinations K also comprise a dicarboximide (group 12) selected from
(12-1) captafol
(12-2) captan
(12-3) folpet
(12-4) iprodione
(12-5) procymidone
(12-6) vinclozolin Preference is given to active compound combinations K in which the dicarboximide (group 12) is selected from the following list:
(12-2) captan
(12-3) folpet
(12-4) iprodione Emphasis is given to the active compound combinations K listed in Table 11 below:

TABLE 11

Active compound combinations K

| No. | Carboxamide of the formula (I) | Dicarboximide |
|---|---|---|
| K-1 | (1-1) N-(3',4'-dichloro-5-fluoro-1,1'-biphenyl-2-yl)-3-(difluoromethyl)-1-methyl-1H-pyrazole-4-carboxamide | (12-2) captan |
| K-2 | (1-1) N-(3',4'-dichloro-5-fluoro-1,1'-biphenyl-2-yl)-3-(difluoromethyl)-1-methyl-1H-pyrazole-4-carboxamide | (12-3) folpet |
| K-3 | (1-1) N-(3',4'-dichloro-5-fluoro-1,1'-biphenyl-2-yl)-3-(difluoromethyl)-1-methyl-1H-pyrazole-4-carboxamide | (12-4) iprodione |
| K-4 | (1-7) N-(4'-bromo-1,1'-biphenyl-2-yl)-4-(difluoromethyl)-2-methyl-1,3-thiazole-5-carboxamide | (12-2) captan |
| K-5 | (1-7) N-(4'-bromo-1,1'-biphenyl-2-yl)-4-(difluoromethyl)-2-methyl-1,3-thiazole-5-carboxamide | (12-3) folpet |
| K-6 | (1-7) N-(4'-bromo-1,1'-biphenyl-2-yl)-4-(difluoromethyl)-2-methyl-1,3-thiazole-5-carboxamide | (12-4) iprodione |
| K-7 | (1-8) 4-(difluoromethyl)-2-methyl-N-[4'-(trifluoromethyl)-1,1'-biphenyl-2-yl]-1,3-thiazole-5-carboxamide | (12-2) captan |
| K-8 | (1-8) 4-(difluoromethyl)-2-methyl-N-[4'-(trifluoromethyl)-1,1'-biphenyl-2-yl]-1,3-thiazole-5-carboxamide | (12-3) folpet |
| K-9 | (1-8) 4-(difluoromethyl)-2-methyl-N-[4'-(trifluoromethyl)-1,1'-biphenyl-2-y11-1,3-thiazole-5-carboxamide | (12-4) iprodione |
| K-10 | (1-9) N-(4'-chloro-3'-fluoro-1,1'-biphenyl-2-yl)-4-(difluoromethyl)-2-methyl-1,3-thiazole-5-carboxamide | (12-2) captan |
| K-11 | (1-9) N-(4'-chloro-3'-fluoro-1,1'-biphenyl-2-yl)-4-(difluoromethyl)-2-methyl-1,3-thiazole-5-carboxamide | (12-3) folpet |
| K-12 | (1-9) N-(4'-chloro-3'-fluoro-1,1'-biphenyl-2-yl)-4-(difluoromethyl)-2-methyl-1,3-thiazole-5-carboxamide | (12-4) iprodione |

In addition to a carboxamide of the formula (I) (group 1), the active compound combinations L also comprise a guanidine (group 13) selected from
(13-1) dodine
(13-2) guazatine
(13-3) iminoctadine triacetate
(13-4) iminoctadine tris(albesilate)

Preference is given to active compound combinations L in which the guanidine (group 13) is selected from the following list:
(13-1) dodine
(13-2) guazatine Emphasis is given to the active compound combinations L listed in Table 12 below:

TABLE 12

Active compound combinations L

| No. | Carboxamide of the formula (I) | Guanidine |
|---|---|---|
| L-1 | (1-1) N-(3',4'-dichloro-5-fluoro-1,1'-biphenyl-2-yl)-3-(difluoromethyl)-1-methyl-1H-pyrazole-4-carboxamide | (13-1) dodine |
| L-2 | (1-1) N-(3',4'-dichloro-5-fluoro-1,1'-biphenyl-2-yl)-3-(difluoromethyl)-1-methyl-1H-pyrazole-4-carboxamide | (13-2) guazatine |
| L-3 | (1-7) N-(4'-bromo-1,1'-biphenyl-2-yl)-4-(difluoromethyl)-2-methyl-1,3-thiazole-5-carboxamide | (13-1) dodine |
| L-4 | (1-7) N-(4'-bromo-1,1'-biphenyl-2-yl)-4-(difluoromethyl)-2-methyl-1,3-thiazole-5-carboxamide | (13-2) guazatine |
| L-5 | (1-8) 4-(difluoromethyl)-2-methyl-N-[4'-(trifluoromethyl)-1,1'-biphenyl-2-yl]-1,3-thiazole-5-carboxamide | (13-1) dodine |
| L-6 | (1-8) 4-(difluoromethyl)-2-methyl-N-[4'-(trifluoromethyl)-1,1'-biphenyl-2-yl]-1,3-thiazole-5-carboxamide | (13-2) guazatine |
| L-7 | (1-9) N-(4'-chloro-3'-fluoro-1,1'-biphenyl-2-yl)-4-(difluoromethyl)-2-methyl-1,3-thiazole-5-carboxamide | (13-1) dodine |
| L-8 | (1-9) N-(4'-chloro-3'-fluoro-1,1'-biphenyl-2-yl)-4-(difluoromethyl)-2-methyl-1,3-thiazole-5-carboxamide | (13-2) guazatine |

In addition to a carboxamide of the formula (I) (group 1), the active compound combinations M also comprise an imidazole (group 14) selected from
(14-1) cyazofamid
(14-2) prochloraz
(14-3) triazoxide
(14-4) pefurazoate Preference is given to active compound combinations M in which the imidazole (group 14) is selected from the following list:
(14-2) prochloraz
(14-3) triazoxide Emphasis is given to the active compound combinations M listed in Table 13 below:

TABLE 13

Active compound combinations M

| No. | Carboxamide of the formula (I) | Imidazole |
|---|---|---|
| M-1 | (1-1) N-(3',4'-dichloro-5-fluoro-1,1'-biphenyl-2-yl)-3-(difluoromethyl)-1-methyl-1H-pyrazole-4-carboxamide | (14-2) prochloraz |
| M-2 | (1-1) N-(3',4'-dichloro-5-fluoro-1,1'-biphenyl-2-yl)-3-(difluoromethyl)-1-methyl-1H-pyrazole-4-carboxamide | (14-3) triazoxide |
| M-3 | (1-7) N-(4'-bromo-1,1'-biphenyl-2-yl)-4-(difluoromethyl)-2-methyl-1,3-thiazole-5-carboxamide | (14-2) prochloraz |
| M-4 | (1-7) N-(4'-bromo-1,1'-biphenyl-2-yl)-4-(difluoromethyl)-2-methyl-1,3-thiazole-5-carboxamide | (14-3) triazoxide |
| M-5 | (1-8) 4-(difluoromethyl)-2-methyl-N-[4'-(trifluoromethyl)-1,1'-biphenyl-2-yl]-1,3-thiazole-5-carboxamide | (14-2) prochloraz |
| M-6 | (1-8) 4-(difluoromethyl)-2-methyl-N-[4'-(trifluoromethyl)-1,1'-biphenyl-2-yl]-1,3-thiazole-5-carboxamide | (14-3) triazoxide |
| M-7 | (1-9) N-(4'-chloro-3'-fluoro-1,1'-biphenyl-2-yl)-4-(difluoromethyl)-2-methyl-1,3-thiazole-5-carboxamide | (14-2) prochloraz |
| M-8 | (1-9) N-(4'-chloro-3'-fluoro-1,1'-biphenyl-2-yl)-4-(difluoromethyl)-2-methyl-1,3-thiazole-5-carboxamide | (14-3) triazoxide |

In addition to a carboxamide of the formula (I) (group 1), the active compound combinations N also comprise a morpholine (group 15) of the formula (X)

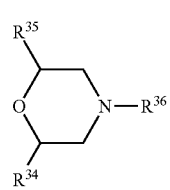

(X)

in which $R^{34}$, $R^{35}$ and $R^{36}$ are as defined above.

Preference is given to active compound combinations N in which the morpholine (group 15) of the formula (X) is selected from the following list:
(15-1) aldimorph
(15-2) tridemorph
(15-3) dodemorph
(15-4) fenpropimorph
(15-5) dimethomorph Particular preference is given to active compound combinations N in which the morpholine (group 15) of the formula (X) is selected from the following list:
(15-4) fenpropimorph
(15-5) dimethomorph Emphasis is given to the active compound combinations N listed in Table 14 below:

TABLE 14

Active compound combinations N

| No. | Carboxamide of the formula (I) | Morpholine of the formula (X) |
|---|---|---|
| N-1 | (1-1) N-(3',4'-dichloro-5-fluoro-1,1'-biphenyl-2-yl)-3-(difluoromethyl)-1-methyl-1H-pyrazole-4-carboxamide | (15-4) fenpropimorph |
| N-2 | (1-7) N-(4'-bromo-1,1'-biphenyl-2-yl)-4-(difluoromethyl)-2-methyl-1,3-thiazole-5-carboxamide | (15-4) fenpropimorph |
| N-3 | (1-8) 4-(difluoromethyl)-2-methyl-N-[4'-(trifluoromethyl)-1,1'-biphenyl-2-yl]-1,3-thiazole-5-carboxamide | (15-4) fenpropimorph |
| N-4 | (1-9) N-(4'-chloro-3'-fluoro-1,1'-biphenyl-2-yl)-4-(difluoromethyl)-2-methyl-1,3-thiazole-5-carboxamide | (15-4) fenpropimorph |

In addition to a carboxamide of the formula (I) (group 1), the active compound combinations O also comprise a pyrrole (group 16) of the formula (XI)

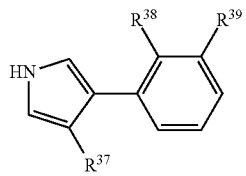

(XI)

in which $R^{37}$, $R^{38}$ and $R^{39}$ are as defined above.

Preference is given to active compound combinations O in which the pyrrole (group 16) of the formula (XI) is selected from the following list:
(16-1) fenpiclonil
(16-2) fludioxonil
(16-3) pyrrolnitrin Particular preference is given to active compound combinations O in which the pyrrole (group 16) of the formula (XI) is selected from the following list:
(16-2) fludioxonil Emphasis is given to the active compound combinations O listed in Table 15 below:

TABLE 15

Active compound combinations O

| No. | Carboxamide of the formula (I) | Pyrrole of the formula (XI) |
|---|---|---|
| O-1 | (1-1) N-(3',4'-dichloro-5-fluoro-1,1'-biphenyl-2-yl)-3-(difluoromethyl)-1-methyl-1H-pyrazole-4-carboxamide | (16-2) fludioxonil |
| O-2 | (1-7) N-(4'-bromo-1,1'-biphenyl-2-yl)-4-(difluoromethyl)-2-methyl-1,3-thiazole-5-carboxamide | (16-2) fludioxonil |
| O-3 | (1-8) 4-(difluoromethyl)-2-methyl-N-[4'-(trifluoromethyl)-1,1'-biphenyl-2-yl]-1,3-thiazole-5-carboxamide | (16-2) fludioxonil |
| O-4 | (1-9) N-(4'-chloro-3'-fluoro-1,1'-biphenyl-2-yl)-4-(difluoromethyl)-2-methyl-1,3-thiazole-5-carboxamide | (16-2) fludioxonil |

In addition to a carboxamide of the formula (I) (group 1), the active compound combinations P also comprise a phosphonate (group 17) selected from
(17-1) fosetyl-Al
(17-2) phosphonic acid Emphasis is given to the active compound combinations P listed in Table 16 below:

TABLE 16

Active compound combinations P

| No. | Carboxamide of the formula (I) | Phosphonate |
|---|---|---|
| P-1 | (1-1) N-(3',4'-dichloro-5-fluoro-1,1'-biphenyl-2-yl)-3-(difluoromethyl)-1-methyl-1H-pyrazole-4-carboxamide | (17-1) fosetyl-Al |
| P-2 | (1-7) N-(4'-bromo-1,1'-biphenyl-2-yl)-4-(difluoromethyl)-2-methyl-1,3-thiazole-5-carboxamide | (17-1) fosetyl-Al |
| P-3 | (1-8) 4-(difluoromethyl)-2-methyl-N-[4'-(trifluoromethyl)-1,1'-biphenyl-2-yl]-1,3-thiazole-5-carboxamide | (17-1) fosetyl-Al |
| P-4 | (1-9) N-(4'-chloro-3'-fluoro-1,1'-biphenyl-2-yl)-4-(difluoromethyl)-2-methyl-1,3-thiazole-5-carboxamide | (17-1) fosetyl-Al |

In addition to a carboxamide of the formula (I) (group 1), the active compound combinations Q also comprise a fungicide (group 19) selected from
(19-1) acibenzolar-S-methyl
(19-2) chlorothalonil
(19-3) cymoxanil
(19-4) edifenphos
(19-5) famoxadone
(19-6) fluazinam
(19-7) copper oxychloride
(19-8) copper hydroxide
(19-9) oxadixyl
(19-10) spiroxamine
(19-11) dithianon
(19-12) metrafenone
(19-13) fenamidone
(19-14) 2,3-dibutyl-6-chlorothieno[2,3-d]pyrimidin-4(3H)one
(19-15) probenazole
(19-16) isoprothiolane
(19-17) kasugamycin
(19-18) phthalide
(19-19) ferimzone
(19-20) tricyclazole
(19-21) N-({4-[(cyclopropylamino)carbonyl]phenyl}sulphonyl)-2-methoxybenzamide
(19-22) 2-(4-chlorophenyl)-N-{2-[3-methoxy-4-(prop-2-yn-1-yloxy)phenyl]ethyl}-2-(prop-2-yn-1-yloxy)acetamide Preference is given to active compound combinations Q in which the fungicide (group 19) is selected from the following list:
(19-1) acibenzolar-S-methyl
(19-2) chlorothalonil
(19-3) cymoxanil (19-5) famoxadone
(19-6) fluazinam
(19-7) copper oxychloride
(19-9) oxadixyl
(19-10) spiroxamine
(19-13) fenamidone
(19-21) N-({4-[(cyclopropylamino)carbonyl]phenyl}sulphonyl)-2-methoxybenzamide
(19-22) 2-(4-chlorophenyl)-N-{2-[3-methoxy-4-(prop-2-yn-1-yloxy)phenyl]ethyl}-2-(prop-2-yn-1-yloxy)acetamide Particular preference is given to active compound combinations Q in which the fungicide (group 19) is selected from the following list:
(19-2) chlorothalonil
(19-7) copper oxychloride
(19-10) spiroxamine
(19-21) N-({4-[(cyclopropylamino)carbonyl]phenyl}sulphonyl)-2-methoxybenzamide
(19-22) 2-(4-chlorophenyl)-N-{2-[3-methoxy-4-(prop-2-yn-1-yloxy)phenyl]ethyl}-2-(prop-2-yn-1-yloxy)acetamide Emphasis is given to the active compound combinations Q listed in Table 17 below:

In addition to a carboxamide of the formula (I) (group 1), the active compound combinations R also comprise a (thio)urea derivative (group 20) selected from
(20-1) pencycuron
(20-2) thiophanate-methyl
(20-3) thiophanate-ethyl Preference is given to active compound combinations R in which the (thio)urea derivative (group 20) is selected from the following list:
(20-1) pencycuron
(20-2) thiophanate-methyl Emphasis is given to the active compound combinations R listed in Table 18 below:

TABLE 18

Active compound combinations R

| No. | Carboxamide of the formula (I) | (Thio)urea derivative |
|---|---|---|
| R-1 | (1-1) N-(3',4'-dichloro-5-fluoro-1,1'-biphenyl-2-yl)-3-(difluoromethyl)-1-methyl-1H-pyrazole-4-carboxamide | (20-1) pencycuron |

TABLE 17

Active compound combinations Q

| No. | Carboxamide of the formula (I) | Fungicide |
|---|---|---|
| Q-1 | (1-1) N-(3',4'-dichloro-5-fluoro-1,1'-biphenyl-2-yl)-3-(difluoromethyl)-1-methyl-1H-pyrazole-4-carboxamide | (19-2) chlorothalonil |
| Q-2 | (1-1) N-(3',4'-dichloro-5-fluoro-1,1'-biphenyl-2-yl)-3-(difluoromethyl)-1-methyl-1H-pyrazole-4-carboxamide | (19-7) copper oxychloride |
| Q-3 | (1-1) N-(3',4'-dichloro-5-fluoro-1,1'-biphenyl-2-yl)-3-(difluoromethyl)-1-methyl-1H-pyrazole-4-carboxamide | (19-10) spiroxamine |
| Q-4 | (1-1) N-(3',4'-dichloro-5-fluoro-1,1'-biphenyl-2-yl)-3-(difluoromethyl)-1-methyl-1H-pyrazole-4-carboxamide | (19-21) N-({4-[(cyclopropylamino)carbonyl]phenyl}sulphonyl)-2-methoxybenzamide |
| Q-5 | (1-1) N-(3',4'-dichloro-5-fluoro-1,1'-biphenyl-2-yl)-3-(difluoromethyl)-1-methyl-1H-pyrazole-4-carboxamide | (19-22) 2-(4-chlorophenyl)-N-{2-[3-methoxy-4-(prop-2-yn-1-yloxy)phenyl]ethyl}-2-(prop-2-yn-1-yloxy)acetamide |
| Q-6 | (1-7) N-(4'-bromo-1,1'-biphenyl-2-yl)-4-(difluoromethyl)-2-methyl-1,3-thiazole-5-carboxamide | (19-2) chlorothalonil |
| Q-7 | (1-7) N-(4'-bromo-1,1'-biphenyl-2-yl)-4-(difluoromethyl)-2-methyl-1,3-thiazole-5-carboxamide | (19-7) copper oxychloride |
| Q-8 | (1-7) N-(4'-bromo-1,1'-biphenyl-2-yl)-4-(difluoromethyl)-2-methyl-1,3-thiazole-5-carboxamide | (19-10) spiroxamine |
| Q-9 | (1-7) N-(4'-bromo-1,1'-biphenyl-2-yl)-4-(difluoromethyl)-2-methyl-1,3-thiazole-5-carboxamide | (19-21) N-({4-[(cyclopropylamino)carbonyl]phenyl}sulphonyl)-2- |
| Q-10 | (1-7) N-(4'-bromo-1,1'-biphenyl-2-yl)-4-(difluoromethyl)-2-methyl-1,3-thiazole-5-carboxamide | (19-22) 2-(4-chlorophenyl)-N-{2-[3 methoxy-4-(prop-2-yn-1-yloxy)phenyl]-ethyl}-2-(prop-2-yn-1-yloxy)acetamide |
| Q-11 | (1-8) 4-(difluoromethyl)-2-methyl-N-[4'-(trifluoromethyl)-1,1'-biphenyl-2-yl]-1,3-thiazole-5-carboxamide | (19-2) chlorothalonil |
| Q-12 | (1-8) 4-(difluoromethyl)-2-methyl-N-[4'-(trifluoromethyl)-1,1'-biphenyl-2-yl]-1,3-thiazole-5-carboxamide | (19-7) copper oxychloride |
| Q-13 | (1-8) 4-(difluoromethyl)-2-methyl-N-[4'-(trifluoromethyl)-1,1'-biphenyl-2-yl]-1,3-thiazole-5-carboxamide | (19-10) spiroxamine |
| Q-14 | (1-8) 4-(difluoromethyl)-2-methyl-N-[4'-(trifluoromethyl)-1,1'-biphenyl-2-yl]-1,3-thiazole-5-carboxamide | (19-21) N-({4-(cyclopropylamino)carbonyl]phenyl}sulphonyl)-2-methoxybenzamide |
| Q-15 | (1-8) 4-(difluoromethyl)-2-methyl-N-[4'-(trifluoromethyl)-1,1'-biphenyl-2-yl]-1,3-thiazole-5-carboxamide | (19-22) 2-(4-chlorophenyl)-N-{2-[3-methoxy-4-(prop-2-yn-1-yloxy)phenyl]-ethyl}-2-(prop-2-yn-1-yloxy)acetamide |
| Q-16 | (1-9) N-(4'-chloro-3'-fluoro-1,1'-biphenyl-2-yl)-4-(difluoromethyl)-2-methyl-1,3-thiazole-5-carboxamide | (19-2) chlorothalonil |
| Q-17 | (1-9) N-(4'-chloro-3'-fluoro-1,1'-biphenyl-2-yl)-4-(difluoromethyl)-2-methyl-1,3-thiazole-5-carboxamide | (19-7) copper oxychloride |
| Q-18 | (1-9) N-(4'-chloro-3'-fluoro-1,1'-biphenyl-2-yl)-4-(difluoromethyl)-2-methyl-1,3-thiazole-5-carboxamide | (19-10) spiroxamine |
| Q-19 | (1-9) N-(4'-chloro-3'-fluoro-1,1'-biphenyl-2-yl)-4-(difluoromethyl)-2-methyl-1,3-thiazole-5-carboxamide | (19-21) N-({4-[(cyclopropylamino)carbonyl]phenyl}sulphonyl)-2-methoxybenzamide |
| Q-20 | (1-9) N-(4'-chloro-3'-fluoro-1,1'-biphenyl-2-yl)-4-(difluoromethyl)-2-methyl-1,3-thiazole-5-carboxamide | (19-22) 2-(4-chlorophenyl)-N-{2-[3-methoxy-4-(prop-2-yn-1-yloxy)phenyl]-ethyl}-2-(prop-2-yn-1-yloxy)acetamide |

TABLE 18-continued

Active compound combinations R

| No. | Carboxamide of the formula (I) | (Thio)urea derivative |
|---|---|---|
| R-2 | (1-7) N-(4'-bromo-1,1'-biphenyl-2-yl)-4-(difluoromethyl)-2-methyl-1,3-thiazole-5-carboxamide | (20-1) pencycuron |
| R-3 | (1-8) 4-(difluoromethyl)-2-methyl-N-[4'-(trifluoromethyl)-1,1'-biphenyl-2-yl]-1,3-thiazole-5-carboxamide | (20-1) pencycuron |
| R-4 | (1-9) N-(4'-chloro-3'-fluoro-1,1'-biphenyl-2-yl)-4-(difluoromethyl)-2-methyl-1,3-thiazole-5-carboxamide | (20-1) pencycuron |

In addition to a carboxamide of the formula (I) (group 1), the active compound combinations S also comprise a triazolopyrimidine (group 22) of the formula (XIV)

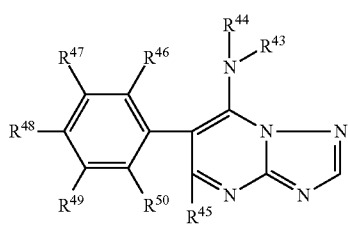

(XIV)

in which $R^{43}$, $R^{44}$, $R^{45}$, $R^{46}$, $R^{47}$, $R^{48}$, $R^{49}$ and $R^{50}$ are as defined above.

Preference is given to active compound combinations S in which the triazolopyrimidine (group 22) of the formula (XIV) is selected from the list below:

(22-1) 5-chloro-N-[(1S)-2,2,2-trifluoro-1-methylethyl]-6-(2,4,6-trifluorophenyl)[1,2,4]triazolo-[1,5-a]pyrimidine-7-amine (22-2) 5-chloro-N-[(1R)-1,2-dimethylpropyl]-6-(2,4,6-trifluorophenyl)[1,2,4]triazolo[1,5-a]-pyrimidine-7-amine (22-3) 5-chloro-6-(2-chloro-6-fluorophenyl)-7-(4-methylpiperidin-1-yl)[1,2,4]triazolo[1,5-a]-pyrimidine (22-4) 5-chloro-6-(2,4,6-trifluorophenyl)-7-(4-methylpiperidin-1-yl)[1,2,4]triazolo[1,5-a]pyrimidine Particular preference is given to active compound combinations S in which the triazolopyrimidine (group 22) of the formula (XIV) is selected from the list below:

(22-1) 5-chloro-N-[(1S)-2,2,2-trifluoro-1-methylethyl]-6-(2,4,6-trifluorophenyl)[1,2,4]triazolo-[1,5-a]pyrimidine-7-amine (22-2) 5-chloro-N—[(R)-1,2-dimethylpropyl]-6-(2,4,6-trifluorophenyl)[1,2,4]triazolo[1,5-a]-pyrimidine-7-amine (22-4) 5-chloro-6-(2,4,6-trifluorophenyl)-7-(4-methylpiperidin-1-yl)[1,2,4]triazolo[1,5-a]pyrimidine Emphasis is given to the active compound combinations S listed in Table 19 below:

TABLE 19

Active compound combinations S

| No. | Carboxamide of the formula (I) | Triazolopyrimidine of the formula (XIV) |
|---|---|---|
| S-1 | (1-1) N-(3',4'-dichloro-5-fluoro-1,1'-biphenyl-2-yl)-3-(difluoromethyl)-1-methyl-1H-pyrazole-4-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |
| S-2 | (1-1) N-(3',4'-dichloro-5-fluoro-1,1'-biphenyl-2-yl)-3-(difluoromethyl)-1-methyl-1H-pyrazole-4-carboxamide | (22-2) 5-chloro-N-[(1R)-1,2-dimethylpropyl]-6-(2,4,6-trifluorophenyl)[1,2,4]triazolo[1,5-a]-pyrimidine-7-amine |
| S-3 | (1-1) N-(3',4'-dichloro-5-fluoro-1,1'-biphenyl-2-yl)-3-(difluoromethyl)-1-methyl-1H-pyrazole-4-carboxamide | (22-4) 5-chloro-6-(2,4,6-trifluorophenyl)-7-(4-methylpiperidin-1-yl)[1,2,4]triazolo[1,5-a]pyrimidine |
| S-4 | (1-7) N-(4'-bromo-1,1'-biphenyl-2-yl)-4-(difluoromethyl)-2-methyl-1,3-thiazole-5-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |
| S-5 | (1-7) N-(4'-bromo-1,1'-biphenyl-2-yl)-4-(difluoromethyl)-2-methyl-1,3-thiazole-5-carboxamide | (22-2) 5-chloro-N-[(1R)-1,2-dimethylpropyl]-6-(2,4,6-trifluorophenyl)[1,2,4]triazolo[1,5-a]-pyrimidine-7-amine |
| S-6 | (1-7) N-(4'-bromo-1,1'-biphenyl-2-yl)-4-(difluoromethyl)-2-methyl-1,3-thiazole-5-carboxamide | (22-4) 5-chloro-6-(2,4,6-trifluorophenyl)-7-(4-methylpiperidin-1-yl)[1,2,4]triazolo[1,5-a]pyrimidine |
| S-7 | (1-8) 4-(difluoromethyl)-2-methyl-N[4'-(trifluoromethyl)-1,1'-biphenyl-2-yl]-1,3-thiazole-5-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |
| S-8 | (1-8) 4-(difluoromethyl)-2-methyl-N[4'-(trifluoromethyl)-1,1'-biphenyl-2-yl]-1,3-thiazole-5-carboxamide | (22-2) 5-chloro-N-[(1R)-1,2-dimethylpropyl]-6-(2,4,6-trifluorophenyl)[1,2,4]triazolo[1,5-a]-pyrimidine-7-amine |
| S-9 | (1-8) 4-(difluoromethyl)-2-methyl-N[4'-(trifluoromethyl)-1,1'-biphenyl-2-yl]-1,3-thiazole-5-carboxamide | (22-4) 5-chloro-6-(2,4,6-trifluorophenyl)-7-(4-methylpiperidin-1-yl)[1,2,4]triazolo[1,5-a]pyrimidine |
| S-10 | (1-9) N-(4'-chloro-3'-fluoro-1,1'-biphenyl-2-yl)-4-(difluoromethyl)-2-methyl-1,3-thiazole-5-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |

TABLE 19-continued

Active compound combinations S

| No. | Carboxamide of the formula (I) | Triazolopyrimidine of the formula (XIV) |
|---|---|---|
| S-11 | (1-9) N-(4'-chloro-3'-fluoro-1,1'-biphenyl-2-yl)-4-(difluoromethyl)-2-methyl-1,3-thiazole-5-carboxamide | (22-2) 5-chloro-N-[(1R)-1,2-dimethylpropyl]-6-(2,4,6-trifluorophenyl)[1,2,4]triazolo[1,5-a]-pyrimidine-7-amine |
| S-12 | (1-9) N-(4'-chloro-3'-fluoro-1,1'-biphenyl-2-yl)-4-(difluoromethyl)-2-methyl-1,3-thiazole-5-carboxamide | (22-4) 5-chloro-6-(2,4,6-trifluorophenyl)-7-(4-methylpiperidin-1-yl)[1,2,4]triazolo[1,5-a]pyrimidine |

In addition to a carboxamide of the formula (I) (group 1), the active compound combinations T also comprise an iodochromone (group 23) of the formula (XV)

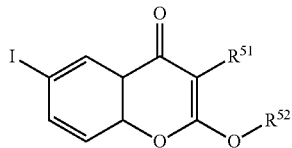

in which $R^{51}$ and $R^{52}$ are as defined above.

Preference is given to active compound combinations T in which the iodochromone (group 23) of the formula (XV) is selected from the following list:
(23-1) 2-butoxy-6-iodo-3-propylbenzopyran-4-one
(23-2) 2-ethoxy-6-iodo-3-propylbenzopyran-4-one
(23-3) 6-iodo-2-propoxy-3-propylbenzopyran-4-one
(23-4) 2-but-2-ynyloxy-6-iodo-3-propylbenzopyran-4-one
(23-5) 6-iodo-2-(1-methylbutoxy)-3-propylbenzopyran-4-one
(23-6) 2-but-3-enyloxy-6-iodobenzopyran-4-one
(23-7) 3-butyl-6-iodo-2-isopropoxybenzopyran-4-one Particular preference is given to active compound combinations T in which the iodochromone (group 23) of the formula (XV) is selected from the following list:
(23-1) 2-butoxy-6-iodo-3-propylbenzopyran-4-one
(23-2) 2-ethoxy-6-iodo-3-propylbenzopyran-4-one Emphasis is given to the active compound combinations T listed in Table 20 below:

TABLE 20

Active compound combinations T

| No. | Carboxamide of the formula (I) | Iodochromone of the formula (XV) |
|---|---|---|
| T-1 | (1-1) N-(3',4'-dichloro-5-fluoro-1,1'-biphenyl-2-yl)-3-(difluoromethyl)-1-methyl-1H-pyrazole-4-carboxamide | (23-1) 2-butoxy-6-iodo-3-propylbenzopyran-4-one |
| T-2 | (1-1) N-(3',4'-dichloro-5-fluoro-1,1'-biphenyl-2-yl)-3-(difluoromethyl)-1-methyl-1H-pyrazole-4-carboxamide | (23-2) 2-ethoxy-6-iodo-3-propylbenzopyran-4-one |
| T-3 | (1-7) N-(4'-bromo-1,1'-biphenyl-2-yl)-4-(difluoromethyl)-2-methyl-1,3-thiazole-5-carboxamide | (23-1) 2-butoxy-6-iodo-3-propylbenzopyran-4-one |
| T-4 | (1-7) N-(4'-bromo-1,1'-biphenyl-2-yl)-4-(difluoromethyl)-2-methyl-1,3-thiazole-5-carboxamide | (23-2) 2-ethoxy-6-iodo-3-propylbenzopyran-4-one |
| T-5 | (1-8) 4-(difluoromethyl)-2-methyl-N[4'-(trifluoromethyl)-1,1'-biphenyl-2-yl]-1,3-thiazole-5-carboxamide | (23-1) 2-butoxy-6-iodo-3-propylbenzopyran-4-one |
| T-6 | (1-8) 4-(difluoromethyl)-2-methyl-N-[4'-(trifluoromethyl)-1,1'-biphenyl-2-yl]-1,3-thiazole-5-carboxamide | (23-2) 2-ethoxy-6-iodo-3-propylbenzopyran-4-one |
| T-7 | (1-9) N-(4'-chloro-3'-fluoro-1,1'-biphenyl-2-yl)-4-(difluoromethyl)-2-methyl-1,3-thiazole-5-carboxamide | (23-1) 2-butoxy-6-iodo-3-propylbenzopyran-4-one |
| T-8 | (1-9) N-(4'-chloro-3'-fluoro-1,1'-biphenyl-2-yl)-4-(difluoromethyl)-2-methyl-1,3-thiazole-5-carboxamide | (23-2) 2-ethoxy-6-iodo-3-propylbenzopyran-4-one |

In addition to an active compound of the formula (I), the active compound combinations according to the invention comprise at least one active compound from the compounds of groups (2) to (23). In addition, they may also comprise further fungicidally active additives.

If the active compounds in the active compound combinations according to the invention are present in certain weight ratios, the synergistic effect is particularly pronounced. However, the weight ratios of the active compounds in the active compound combinations can be varied within a relatively wide range. In general, the combinations according to the invention comprise active compounds of the formula (I) and a mixing partner from one of the groups (2) to (23) in the mixing ratios listed in an exemplary manner in Table 21 below.

The mixing ratios are based on ratios by weight. The ratio is to be understood as active compound of the formula (I): mixing partner.

TABLE 21

Mixing ratios

| Mixing partner | Preferred mixing ratio | Particularly preferred mixing ratio |
|---|---|---|
| Group (2): strobilurins | 50:1 to 1:50 | 10:1 to 1:20 |
| Group (3): triazoles except for (3-15) | 50:1 to 1:50 | 20:1 to 1:20 |
| (3-15): prothioconazole | 50:1 to 1:50 | 10:1 to 1:20 |
| Group (4): sulphenamides | 1:1 to 1:150 | 1:1 to 1:100 |
| Group (5): valinamides | 50:1 to 1:50 | 10:1 to 1:20 |
| Group (6): carboxamides | 50:1 to 1:50 | 20:1 to 1:20 |
| Group (7): dithiocarbamates | 1:1 to 1:150 | 1:1 to 1:100 |

TABLE 21-continued

Mixing ratios

| Mixing partner | Preferred mixing ratio | Particularly preferred mixing ratio |
|---|---|---|
| Group (8): acylalanines | 10:1 to 1:150 | 5:1 to 1:100 |
| Group (9): anilinopyrimidines | 5:1 to 1:50 | 1:1 to 1:20 |
| Group (10): benzimidazoles | 10:1 to 1:50 | 5:1 to 1:20 |
| Group (11): carbamates except for (11-1) | 1:1 to 1:150 | 1:1 to 1:100 |
| (11-1): diethofencarb | 50:1 to 1:50 | 10:1 to 1:20 |
| Group (12): (12-1)/(12-2)/(12-3) | 1:1 to 1:150 | 1:5 to 1:100 |
| Group (12): (12-4)/(12-5)/(12-6) | 5:1 to 1:50 | 1:1 to 1:20 |
| Group (13): guanidines | 100:1 to 1:150 | 20:1 to 1:100 |
| Group (14): imidazoles | 50:1 to 1:50 | 10:1 to 1:20 |
| Group (15): morpholines | 50:1 to 1:50 | 10:1 to 1:20 |
| Group (16): pyrroles | 50:1 to 1:50 | 10:1 to 1:20 |
| Group (17): phosphonates | 10:1 to 1:150 | 1:1 to 1:100 |
| Group (18): phenylethanamides | 50:1 to 1:50 | 10:1 to 1:20 |
| (19-1): acibenzolar-S-methyl | 50:1 to 1:50 | 20:1 to 1:20 |
| (19-2): chlorothalonil | 1:1 to 1:150 | 1:1 to 1:100 |
| (19-3): cymoxanil | 10:1 to 1:50 | 5:1 to 1:20 |
| (19-4): edifenphos | 10:1 to 1:50 | 5:1 to 1:20 |
| (19-5): famoxadone | 50:1 to 1:50 | 10:1 to 1:20 |
| (19-6): fluazinam | 50:1 to 1:50 | 10:1 to 1:20 |
| (19-7): copper oxychloride | 1:1 to 1:150 | 1:5 to 1:100 |
| (19-8): copper hydroxide | 1:1 to 1:150 | 1:5 to 1:100 |
| (19-9): oxadixyl | 10:1 to 1:150 | 5:1 to 1:100 |
| (19-10): spiroxamine | 50:1 to 1:50 | 10:1 to 1:20 |
| (19-11) dithianon | 50:1 to 1:50 | 10:1 to 1:20 |
| (19-12) metrafenone | 50:1 to 1:50 | 10:1 to 1:20 |
| (19-13) fenamidone | 50:1 to 1:50 | 10:1 to 1:20 |
| (19-14): 2,3-dibutyl-6-chlorothieno-[2,3-d]pyrimidin-4(3H)one | 50:1 to 1:50 | 10:1 to 1:20 |
| (19-15): probenazole | 10:1 to 1:150 | 5:1 to 1:100 |
| (19-16): isoprothiolane | 10:1 to 1:150 | 5:1 to 1:100 |
| (19-17): kasugamycin | 50:1 to 1:50 | 10:1 to 1:20 |
| (19-18): phthalide | 10:1 to 1:150 | 5:1 to 1:100 |
| (19-19): ferimzone | 50:1 to 1:50 | 10:1 to 1:20 |
| (19-20): tricyclazole | 50:1 to 1:50 | 10:1 to 1:20 |
| (19-21): N-({4-[(cyclopropylamino)-carbonyl]phenyl}sulphonyl)-2-methoxybenzamide | 10:1 to 1:150 | 5:1 to 1:100 |
| (19-22) 2-(4-chlorophenyl)-N-{2-[3-methoxy-4-(prop-2-yn-1-yloxy)-phenyl]ethyl}-2-(prop-2-yn-1-yloxy)acetamide | 50:1 to 1:50 | 10:1 to 1:20 |
| Group (20): (thio)urea derivatives | 50:1 to 1:50 | 10:1 to 1:20 |
| Group (21): amides | 50:1 to 1:50 | 10:1 to 1:20 |
| Group (22): triazolopyrimidines | 50:1 to 1:50 | 10:1 to 1:20 |
| Group (23): iodochromones | 50:1 to 1:50 | 10:1 to 1:20 |

In each case, the mixing ratio is to be chosen such that a synergistic mixture is obtained. The mixing ratios between the compound of the formula (I) and a compound of one of the groups (2) to (23) may also vary between the individual compounds of a group.

The active compound combinations according to the invention have very good fungicidal properties and are suitable for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling *Erysiphe graminis, Pyrenophora teres* and *Leptosphaeria nodorum*.

Some pathogens causing fungal diseases which come under the generic names listed above may be mentioned by way of example, but not by way of limitation:

*Pythium* species, such as, for example, *Pythium ultimum; Phytophthora* species, such as, for example, *Phytophthora infestans; Pseudoperonospora* species, such as, for example, *Pseudoperonospora humuli* or *Pseudoperonospora cubensis; Plasmopara* species, such as, for example, *Plasmopara viticola; Bremia* species, such as, for example, *Bremia lactucae; Peronospora* species, such as, for example, *Peronospora pisi* or *P. brassicae; Erysiphe* species, such as, for example, *Erysiphe graminis; Sphaerotheca* species, such as, for example, *Sphaerotheca fuliginea; Podosphaera* species, such as, for example, *Podosphaera leucotricha; Venturia* species, such as, for example, *Venturia inaequalis; Pyrenophora* species, such as, for example, *Pyrenophora teres* or *P. graminea* (conidia form: *Drechslera*, syn: *Helminthosporium*); *Cochliobolus* species, such as, for example, *Cochliobolus sativus* (conidia form: *Drechslera*, syn: *Helminthosporium*); *Uromyces* species, such as, for example, *Uromyces appendiculatus; Puccinia* species, such as, for example, *Puccinia recondita; Sclerotinia* species, such as, for example, *Sclerotinia sclerotiorum; Tilletia* species, such as, for example, *Tilletia caries; Ustilago* species, such as, for example, *Ustilago nuda* or *Ustilago avenae; Pellicularia* species, such as, for example, *Pellicularia sasakii; Pyricularia* species, such as, for example, *Pyricularia oryzae; Fusarium* species, such as, for example, *Fusarium culmorum; Botrytis* species, such as, for example, *Botrytis cinerea; Septoria* species, such as, for example, *Septoria nodorum; Leptosphaeria* species, such as, for example, *Leptosphaeria nodorum; Cercospora* species, such as, for example, *Cercospora canescens; Alternaria* species, such as, for example, *Alternaria brassicae; Pseudocercosporella* species, such as, for example, *Pseudocercosporella herpotrichoides, Rhizoctonia* species, such as, for example, *Rhizoctonia solani*.

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application or else as seed dressings.

The active compound combinations according to the invention are also suitable for increasing the yield of crops. In addition, they show reduced toxicity and are well tolerated by plants.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (genetically modified organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized in particular are increased defense of the plants against insects, by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosates or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya bean), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

Depending on their particular physical and/or chemical properties, the active compound combinations according to the invention can be converted into the customary formulations, such as solutions, emulsions, suspensions, powders, dusts, foams, pastes, soluble powders, granules, aerosols, suspoemulsion concentrates, natural and synthetic substances impregnated with active compound and microencapsulations in polymeric substances and in coating compositions for seeds, and ULV cool and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloro-ethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts, ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The active compound content of the use forms prepared from the commercial formulations may be varied within wide ranges. The concentration of active compound of the use forms for controlling animal pests, such as insects and acarids, may be from 0.0000001 to 95% by weight of active compound and is preferably from 0.0001 to 1% by weight. Application is in a customary manner adapted to the use forms.

The formulations for controlling unwanted phytopathogenic fungi generally comprise between 0.1 and 95% by weight of active compounds, preferably between 0.5 and 90%.

The active compound combinations according to the invention can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting.

The active compound combinations according to the invention can, in commercial formulations and in the use forms prepared from these formulations, be present as a mixture with other active compounds, such as insecticides, attractants, sterilants, bactericides, acaricides, nematicides, fungicides, growth regulators or herbicides.

When using the active compound combinations according to the invention, the application rates can be varied within a relatively wide range, depending on the kind of application. In the treatment of parts of plants, the application rates of active compound combinations are generally between 0.1 and 10 000 g/ha, preferably between 10 and 1000 g/ha. In the treatment of seeds, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The active compound combinations can be used as such, in the form of concentrates or in the form of generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and, if desired, colorants and pigments and other processing auxiliaries.

The good fungicidal action of the active compound combinations according to the invention is demonstrated by the examples below. While the individual active compounds show weaknesses in their fungicidal action, the combinations show an action which exceeds a simple sum of actions.

A synergistic effect in fungicides is always present when the fungicidal action of the active compound combinations exceeds the total of the action of the active compounds when applied individually.

The expected fungicidal action for a given combination of two active compounds can be calculated as follows, according to S. R. Colby ("Calculating Synergistic and Antagonistic Responses of Herbicide Combinations", Weeds 1967, 15, 20-22):

If

X is the efficacy when employing active compound A at an application rate of $\underline{m}$ g/ha, Y is the efficacy when employing active compound B at an application rate of $\underline{n}$ g/ha and E is the efficacy when employing active compounds A and B at application rates of $\underline{m}$ and $\underline{n}$ g/ha, then $$E = X + Y - \frac{X \times Y}{100}$$

Here, the efficacy is determined in %. 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

The invention is illustrated by the examples below. However, the invention is not limited to the examples.

USE EXAMPLES

In the use examples shown below, in each case mixtures of the carboxamides of the general formula (I) (group 1) below with the mixing partners given in each case (structural formulae see above) were tested.

Carboxamides of the formula (I) used:

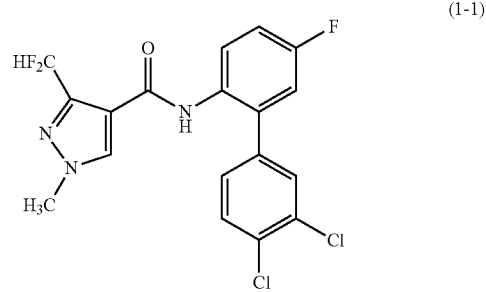

(1-1)

(1-7)

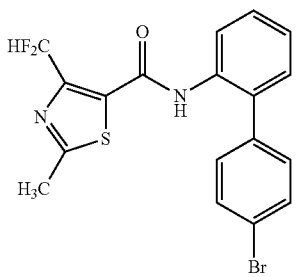

Example A

*Pyrenophora teres* Test (Barley)/Curative
Solvent: 50 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a conidia suspension of *Pyrenophora teres*. The plants remain in an incubation cabinet at 20° C. and 100% relative atmospheric humidity for 48 hours. The plants are then sprayed with the preparation of active compound at the stated application rate.

The plants are placed in a greenhouse at a temperature of about 20° C. and a relative atmospheric humidity of about 80%.

Evaluation is carried out 12 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE A

*Pyrenophora teres* test (barley)/curative

| Active compounds | Application rate of active compound in g/ha | Efficacy in % found* | Efficacy in % calc.** |
|---|---|---|---|
| (1-1) | 25 | 43 | |
| (2-2) fluoxastrobin | 25 | 0 | |
| (3-17) tebuconazole | 25 | 29 | |
| (1-1) + (2-2) fluoxastrobin (1:1) | 25 + 25 | 71 | 43 |
| (1-1) + (3-17) tebuconazole (1:1) | 25 + 25 | 71 | 60 |

*found = activity found
**calc. = activity calculated using Colby's formula

Example B

*Erysiphe* Test (Barley)/Protective
Solvent: 50 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of *Erysiphe graminis* f.sp. *hordei*.

Plants are placed in a greenhouse at a temperature of about 20° C. and a relative atmospheric humidity of about 80% to promote the development of mildew pustules.

Evaluation is carried out 6 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE B

*Erysiphe* test (barley)/protective

| Active compounds | Application rate of active compound in g/ha | Efficacy in % found* | Efficacy in % calc.** |
|---|---|---|---|
| (1-1) | 12.5 | 0 | |
| (2-4) trifloxystrobin | 12.5 | 78 | |
| (3-15) prothioconazole | 12.5 | 67 | |
| (1-1) + (2-4) trifloxystrobin (1:1) | 12.5 + 12.5 | 94 | 78 |
| (1-1) + (3-15) prothioconazole (1:1) | 12.5 + 12.5 | 89 | 67 |

*found = activity found
**calc. = activity calculated using Colby's formula

Example C

*Puccinia* Test (Wheat)/Curative
Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Puccinia recondita*. The plants remain in an incubation cabinet at 20° C. and 100% relative atmospheric humidity for 48 hours.

The plants are then sprayed with the preparation of active compound at the stated application rate.

The plants are placed in a greenhouse at a temperature of about 20° C. and a relative atmospheric humidity of about 80% to promote the development of rust pustules.

Evaluation is carried out 8 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE C

Puccinia test (wheat)/curative

| Active compounds | Application rate of active compound in g/ha | Efficacy in % found* | calc.** |
|---|---|---|---|
| (1-1) | 62.5 | 22 | |
| (19-10) spiroxamine | 62.5 | 0 | |
| (6-14) | 62.5 | 44 | |
| (6-11) | 62.5 | 0 | |
| (2-11) picoxystrobin | 62.5 | 78 | |
| (1-1) + (19-10) spiroxamine (1:1) | 62.5 + 62.5 | 100 | 22 |
| (1-1) + (6-14) (1:1) | 62.5 + 62.5 | 67 | 57 |
| (1-1) + (6-11) (1:1) | 62.5 + 62.5 | 44 | 22 |
| (1-1) + (2-11) picoxystrobin (1:1) | 62.5 + 62.5 | 89 | 83 |

*found = activity found
**calc. = activity calculated using Colby's formula

Example D

*Gibberella zeae* Test (Barley)/Curative
Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Gibberella zeae*. The plants remain in an incubation cabinet at 22° C. and 100% relative atmospheric humidity for 24 hours. The plants are then sprayed with the preparation of active compound at the stated application rate. After the spray coating has dried on, the plants remain in a greenhouse under translucent incubation hoods at a temperature of about 22° C. and a relative atmospheric humidity of about 100%.

Evaluation is carried out 6 days after the inoculation. 0% means an efficacy which corresponds to that of the control, whereas an efficacy of 100% means that no infection is observed.

The table below shows clearly that the activity found for the active compound combination according to the invention is higher than the calculated activity, i.e. that a synergistic effect is present.

TABLE D

Gibberella zeae test (barley)/curative

| Active compounds | Application rate of active compound in g/ha | Efficacy in % found* | calc.** |
|---|---|---|---|
| (1-1) | 62.5 | 40 | |
| (2-12) pyraclostrobin | 62.5 | 80 | |
| (3-12) epoxyconazole | 62.5 | 0 | |
| (1-1) + (2-12) pyraclostrobin (1:1) | 62.5 + 62.5 | 90 | 88 |
| (1-1) + (3-12) epoxyconazole (1:1) | 62.5 + 62.5 | 60 | 40 |

*found = activity found
**calc. = activity calculated using Colby's formula

Example E

*Sphaerotheca fuliginea* Test (Cucumber)/Protective
Solvents: 24.5 parts by weight of acetone
  24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*.

The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE E

Sphaerotheca fuliginea test (cucumber)/protective

| Active compounds | Application rate of active compound in g/ha | Efficacy in % found* | calc.** |
|---|---|---|---|
| (1-1) | 4 | 30 | |
| | 2 | 36 | |
| | 1 | 16 | |
| | 0.5 | 0 | |
| (1-7) | 2 | 0 | |
| | 1 | 0 | |
| | 0.5 | 0 | |
| (2-1) azoxystrobin | 0.5 | 20 | |
| (2-2) fluoxastrobin | 1 | 0 | |
| (2-4) trifloxystrobin | 2 | 10 | |
| (2-12) pyraclostrobin | 2 | 0 | |
| (3-15) prothioconazole | 1 | 43 | |
| (3-17) tebuconazole | 1 | 10 | |
| (3-21) bitertanol | 1 | 0 | |
| (4-2) tolylfluanid | 20 | 0 | |
| (6-6) fenhexamid | 20 | 0 | |
| (6-14) penthiopyrad | 4 | 0 | |
| (7-1) mancozeb | 20 | 0 | |
| (7-4) propineb | 20 | 11 | |
| (9-3) pyrimethanil | 20 | 0 | |
| (12-4) iprodione | 20 | 0 | |
| (19-2) chlorothalonil | 20 | 0 | |
| (19-10) spiroxamine | 20 | 0 | |
| (22-1) | 2 | 11 | |
| (22-2) | 1 | 22 | |
| (1-1) + (2-1) azoxystrobin (1:1) | 0.5 + 0.5 | 87 | 20 |
| (1-7) + (2-1) azoxystrobin (1:1) | 0.5 + 0.5 | 63 | 20 |
| (1-1) + (2-2) fluoxastrobin (1:1) | 1 + 1 | 95 | 16 |
| (1-7) + (2-2) fluoxastrobin (1:1) | 1 + 1 | 92 | 0 |
| (1-1) + (2-4) trifloxystrobin (1:1) | 2 + 2 | 57 | 42 |
| (1-7) + (2-4) trifloxystrobin (1:1) | 2 + 2 | 93 | 10 |
| (1-1) + (2-12) pyraclostrobin (1:1) | 2 + 2 | 53 | 36 |
| (1-1) + (3-15) prothioconazole (1:1) | 1 + 1 | 70 | 52 |
| (1-1) + (3-17) tebuconazole (1:1) | 1 + 1 | 90 | 24 |
| (1-1) + (3-21) bitertanol (1:1) | 1 + 1 | 50 | 16 |
| (1-1) + (4-2) tolylfluanid (1:10) | 2 + 20 | 98 | 36 |
| (1-1) + (6-6) fenhexamid (1:10) | 2 + 20 | 85 | 36 |
| (1-1) + (6-14) penthiopyrad (1:1) | 4 + 4 | 82 | 30 |
| (1-1) + (7-1) mancozeb (1:10) | 2 + 20 | 93 | 36 |
| (1-1) + (7-4) propineb (1:10) | 2 + 20 | 65 | 43 |
| (1-1) + (9-3) pyrimethanil (1:10) | 2 + 20 | 96 | 36 |
| (1-1) + (12-4) iprodione (1:10) | 2 + 20 | 74 | 36 |
| (1-1) + (19-2) chlorothalonil (1:10) | 2 + 20 | 91 | 36 |
| (1-1) + (19-10) spiroxamine (1:10) | 2 + 20 | 100 | 36 |
| (1-1) + (22-1) (1:1) | 2 + 2 | 67 | 43 |
| (1-1) + (22-2) (1:1) | 1 + 1 | 94 | 34 |

*found = activity found
**calc. = activity calculated using Colby's formula

Example F

*Alternaria solani* Test (Tomato)/Protective
Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Alternaria solani*.

The plants are then placed in an incubation cabinet at about 20° C. and 100% relative atmospheric humidity.

Evaluation is carried out 3 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE F

*Alternaria solani* test (tomato)/protective

| Active compounds | Application rate of active compound in g/ha | Efficacy in % found* | calc.** |
|---|---|---|---|
| (1-1) | 1 | 61 | |
| | 0.5 | 42 | |
| (1-7) | 1 | 63 | |
| | 0.5 | 28 | |
| (2-3) | 0.5 | 22 | |
| (3-3) propiconazole | 0.5 | 3 | |
| (5-3) benthiavalicarb | 1 | 5 | |
| (8-4) metalaxyl-M | 0.5 | 7 | |
| (8-5) benalaxyl-M | 0.5 | 14 | |
| (1-7) + (2-3) (1:1) | 0.5 + 0.5 | 67 | 44 |
| (1-7) + (3-3) propiconazole (1:1) | 0.5 + 0.5 | 56 | 30 |
| (1-1) + (5-3) benthiavalicarb (1:1) | 1 + 1 | 77 | 63 |
| (1-1) + (8-4) metalaxyl-M (1:1) | 0.5 + 0.5 | 62 | 46 |
| (1-1) + (8-5) benalaxyl-M (1:1) | 0.5 + 0.5 | 67 | 50 |

*found = activity found
**calc. = activity calculated using Colby's formula

Example G

*Phytophthora infestans* Test (Tomato)/Protective
Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Phytophthora infestans*. The plants are then placed in an incubation cabinet at about 20° C. and 100% relative atmospheric humidity.

Evaluation is carried out 3 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE G

*Phytophthora infestans* test (tomato)/protective

| Active compounds | Application rate of active compound in g/ha | Efficacy in % found* | calc.** |
|---|---|---|---|
| (1-1) | 10 | 0 | |
| | 5 | 0 | |
| | 1 | 0 | |
| | 0.5 | 0 | |
| (4-2) tolylfluanid | 10 | 0 | |
| (5-1) iprovalicarb | 10 | 64 | |
| | 5 | 61 | |
| (5-3) benthiavalicarb | 0.5 | 56 | |
| (19-13) fenamidone | 0.5 | 41 | |
| (1-1) + (4-2) tolylfluanid (1:10) | 1 + 10 | 51 | 0 |
| (1-1) + (5-1) iprovalicarb (1:1) | 10 + 10 | 88 | 64 |
| | 5 + 5 | 77 | 61 |
| (1-1) + (5-3) benthiavalicarb (1:1) | 0.5 + 0.5 | 73 | 56 |
| (1-1) + (19-13) fenamidone (1:1) | 0.5 + 0.5 | 51 | 41 |

*found = activity found
**calc. = activity calculated using Colby's formula

Example H

*Botrytis cinerea* Test (Bean)/Protective
Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a darkened chamber at about 20° C. and 100% relative atmospheric humidity.

The size of the infected areas on the leaves is evaluated 2 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE H

*Botrytis cinerea* test (bean)/protective

| Active compounds | Application rate of active compound in g/ha | Efficacy in % found* | calc.** |
|---|---|---|---|
| (1-1) | 5 | 54 | |
| (9-3) pyrimethanil | 5 | 4 | |

TABLE H-continued

Botrytis cinerea test (bean)/protective

| Active compounds | Application rate of active compound in g/ha | Efficacy in % found* | calc.** |
|---|---|---|---|
| (12-4) iprodione | 5 | 13 | |
| (1-1) + (9-3) pyrimethanil (1:1) | 5 + 5 | 92 | 56 |
| (1-1) + (12-4) iprodione (1:1) | 5 + 5 | 100 | 60 |

*found = activity found
**calc. = activity calculated using Colby's formula

Example I

*Alternaria mali* Test (In Vitro)/Microtitre Plates

The microtest is carried out in microtitre plates using potato dextrose broth (PDB) as liquid test medium. The active compounds are used as technical grade a.i., dissolved in acetone.

For inoculation, a spore suspension of *Alternaria mali* is used. After 5 days of incubation in the dark and with shaking (10 Hz), for each filled cavity of the microtitre plates, the light transmittance is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is higher than the calculated activity, i.e. that a synergistic effect is present.

TABLE I

*Alternaria mali* test (in vitro)/microtitre plates

| Active compounds | Application rate of active compound in ppm | Efficacy in % found* | calc.** |
|---|---|---|---|
| (1-1) | 0.03 | 51 | |
| | 0.003 | 25 | |
| (10-3) carbendazim | 0.03 | 15 | |
| (19-3) fenamidone | 0.003 | 2 | |
| (20-1) pencycuron | 0.003 | 11 | |
| (1-1) + (10-3) carbendazim (1:1) | 0.03 + 0.03 | 79 | 59 |
| (1-1) + (19-3) fenamidone (1:1) | 0.003 + 0.003 | 35 | 27 |
| (1-1) + (20-1) pencycuron (1:1) | 0.003 + 0.003 | 67 | 33 |

*found = activity found
**calc. = activity calculated using Colby's formula

Example J

*Rhizoctonia solani* Test (In Vitro)/Microtitre Plates

The microtest is carried out in microtitre plates using potato dextrose broth (PDB) as liquid test medium. The active compounds are used as technical grade a.i., dissolved in acetone.

For inoculation, a mycelium suspension of *Rhizoctonia solani* is used. After 5 days of incubation in the dark and with shaking (10 Hz), for each filled cavity of the microtitre plates, the light transmittance is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is higher than the calculated activity, i.e. that a synergistic effect is present.

TABLE J

*Rhizoctonia solani* test (in vitro)/microtitre plates

| Active compounds | Application rate of active compound in ppm | Efficacy in % found* | calc.** |
|---|---|---|---|
| (1-1) | 0.3 | 80 | |
| | 0.1 | 40 | |
| (17-1) fosetyl-Al | 0.3 | 24 | |
| (11-2) propamocarb | 0.1 | 25 | |
| (1-1) + (17-1) fosetyl-Al (1:1) | 0.3 + 0.3 | 98 | 85 |
| (1-1) + (11-2) propamocarb (1:1) | 0.1 + 0.1 | 88 | 55 |

*found = activity found
**calc. = activity calculated using Colby's formula

Example K

*Septoria tritici* Test (In Vitro)/Microtitre Plates

The microtest is carried out in microtitre plates using potato dextrose broth (PDB) as liquid test medium. The active compounds are used as technical grade a.i., dissolved in acetone.

For inoculation, a spore suspension of *Septoria tritici* is used. After 7 days of incubation in the dark and with shaking (10 Hz), for each filled cavity of the microtitre plates, the light transmittance is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is higher than the calculated activity, i.e. that a synergistic effect is present.

TABLE K

*Septoria tritici* test (in vitro)/microtitre plates

| Active compounds | Application rate of active compound in ppm | Efficacy in % found* | calc.** |
|---|---|---|---|
| (1-1) | 0.01 | 15 | |
| (14-3) triazoxide | 0.01 | 29 | |
| (1-1) + (14-3) triazoxide (1:1) | 0.01 + 0.01 | 69 | 40 |

*found = activity found
**calc. = activity calculated using Colby's formula

Example L

*Sphaerotheca fuliginea* Test (Gherkin)/Protective

To produce a suitable preparation of active compound, the substance to be tested is homogenized in a mixture of acetone/Tween/water. The suspension is then diluted with water to the desired concentration.

Gherkin plants (Vert petit de Paris cultivar) are sown in starter cups on 50/50 peat soil/pozzolana soil substrate and cultivated at 20° C./23° C. At the 2-leaf stage, the plants are sprayed with the preparation of active compound at the stated application rate.

To test for protective activity, the plants are, after 24 h, sprayed with an aqueous spore suspension of *Sphaerotheca fuliginea* (100 000 spores/ml). The plants then remain at 20° C./25° C. and 60/70% relative atmospheric humidity.

Evaluation is carried out 21 days after the inoculation. 0% means an efficacy which corresponds to that of the control, whereas an efficacy of 100% means that no infection is observed.

The table below shows clearly that the activity found for the active compound combination according to the invention is higher than the calculated activity, i.e. that a synergistic effect is present.

TABLE L

*Sphaerotheca fuliginea* test (gherkin)/protective

| Active compounds | Application rate of active compound in ppm | Efficacy in % found* | calc.** |
|---|---|---|---|
| (1-1) | 8 | 60 | |
| (6-2) boscalid | 8 | 50 | |
| (1-1) + (6-2) boscalid (1:1) | 8 + 8 | 98 | 80 |

*found = activity found
**calc. = activity calculated using Colby's formula

The invention claimed is:

1. A composition comprising (1-1) N-(3',4'-dichloro-5-fluoro-1,1'-biphenyl-2-yl)-3-(difluoromethyl)-1-methyl-1H-pyrazole-4-carboxamide and at least one fungicidal compound selected from the group consisting of: (19-2) chlorothalonil; (19-10) spiroxamine; and (19-13) fenamidone wherein the weight ratio of (1-1) to (19-2), (19-10) or (19-13) is from 1:1 to 1:20, and wherein if the fungicidal compound is spiroxamine, then spiroxamine and N-(3',4'-dichloro-5-fluoro-1,1'-biphenyl-2-yl)-3-(difluoromethyl)-1-methyl-1H-pyrazole-4-carboxamide are the only fungicidal compounds in the composition.

2. A method for controlling unwanted phytopathogenic fungi, comprising applying a composition according to claim 1 to the unwanted phytopathogenic fungi, their habitat, or a combination thereof.

3. A process for preparing a fungicidal composition, comprising mixing a composition according to claim 1 with an extender, a surfactant, or a combination thereof.

4. The composition of claim 1 wherein the active compound is spiroxamine.

5. The composition of claim 1, which comprises (1-1) N-(3',4'-dichloro-5-fluoro-1,1'-biphenyl-2-yl)-3-(difluoromethyl)-1-methyl-1H-pyrazole-4-carboxamide and (19-2) chlorothalonil.

6. The composition of claim 1, which comprises (1-1) N-(3',4'-dichloro-5-fluoro-1,1'-biphenyl-2-yl)-3-(difluoromethyl)-1-methyl-1H-pyrazole-4-carboxamide and (19-13) fenamidone.

* * * * *